(12) United States Patent
Bonanomi et al.

(10) Patent No.: US 11,174,262 B2
(45) Date of Patent: Nov. 16, 2021

(54) COMPOUNDS, COMPOSITIONS AND METHODS

(71) Applicant: Denali Therapeutics Inc., South San Francisco, CA (US)

(72) Inventors: Giorgio Bonanomi, Verona (IT); Anthony A. Estrada, South San Franscisco, CA (US); Jianwen A. Feng, South San Francisco, CA (US); Brian Fox, South San Francisco, CA (US); Cinzia Maria Francini, Verona (IT); Cheng Hu, South San Francisco, CA (US); Colin Philip Leslie, Verona (IT); Maksim Osipov, South San Franscisco, CA (US); Anantha Sudhakar, South San Francisco, CA (US); Zachary K. Sweeney, South San Francisco, CA (US); Javier De Vicente Fidalgo, South San Francisco, CA (US)

(73) Assignee: Denali Therapeutics Inc., South San Francisco, CA (US)

( * ) Notice: Subject to any disclaimer, the term of this patent is extended or adjusted under 35 U.S.C. 154(b) by 0 days.

(21) Appl. No.: 16/683,970

(22) Filed: Nov. 14, 2019

(65) Prior Publication Data
US 2020/0079784 A1 Mar. 12, 2020

Related U.S. Application Data

(63) Continuation of application No. PCT/US2018/033269, filed on May 17, 2018.

(60) Provisional application No. 62/507,682, filed on May 17, 2017.

(51) Int. Cl.
| | | |
|---|---|---|
| *C07D 487/10* | (2006.01) |
| *C07D 495/14* | (2006.01) |
| *C07D 495/20* | (2006.01) |
| *A61K 31/55* | (2006.01) |
| *A61K 31/551* | (2006.01) |
| *A61K 31/553* | (2006.01) |
| *A61K 31/554* | (2006.01) |
| *A61P 25/00* | (2006.01) |
| *A61P 25/16* | (2006.01) |
| *A61P 25/28* | (2006.01) |
| *C07D 487/04* | (2006.01) |
| *C07D 498/04* | (2006.01) |

(52) U.S. Cl.
CPC .......... *C07D 487/04* (2013.01); *C07D 498/04* (2013.01)

(58) Field of Classification Search
CPC ............... C07D 487/10; C07D 495/14; C07D 495/20; A61K 31/55; A61K 31/551; A61K 31/553; A61K 31/554; A61P 25/00; A61P 25/16; A61P 25/28
See application file for complete search history.

(56) References Cited

U.S. PATENT DOCUMENTS

| 4,290,952 A | 9/1981 | Freed et al. |
| 2010/0190688 A1 | 7/2010 | Chao et al. |
| 2011/0305777 A1 | 12/2011 | Condon et al. |

FOREIGN PATENT DOCUMENTS

| WO | 2016094846 A1 | 6/2016 |
| WO | 2016101887 A1 | 6/2016 |

OTHER PUBLICATIONS

Compound Summary for CID 73441087, PubChem (downloaded on Jul. 18, 2018, from https://pubchem.ncbi.nlm.nih.gov/compound/73441087), 10 pages.

International Search Report and Written Opinion of International Application No. PCT/US2018/033269, dated Sep. 24, 2018 (8 pages).

Extended European Search Report issued in corresponding European Patent Application No. 18803112.4 dated Feb. 8, 2021 (6 pages).

*Primary Examiner* — Bruck Kifle
(74) *Attorney, Agent, or Firm* — McNeill Baur PLLC

(57) ABSTRACT

The present disclosure relates generally to methods and compositions for preventing or arresting cell death and/or inflammation.

16 Claims, No Drawings

COMPOUNDS, COMPOSITIONS AND METHODS

CROSS-REFERENCE TO RELATED APPLICATIONS

This application is a United States non-provisional continuation application filed under 35 U.S.C. § 111(a) of International Patent Application No. PCT/US2018/033269, filed on May 17, 2018, which claims priority under 35 U.S.C. § 119(e) of U.S. Provisional Application No. 62/507,682, filed May 17, 2017. The entire contents of each of these applications are incorporated by reference in their entirety into this application.

FIELD

The present disclosure relates generally to compounds, methods and compositions for preventing or arresting cell death and/or inflammation.

BACKGROUND

Programmed necrotic cell death, also called necroptosis, is a form of cell death in which various stimuli such as TNFα, certain toll-like receptor (TLR) agonists and ischemia can induce cellular necrosis. Necroptosis is a highly inflammatory form of cell death and is thought to be an important contributor to pathology in multiple degenerative and inflammatory diseases. These diseases include neurodegenerative diseases, stroke, coronary heart disease and myocardial infarction, retinal degenerative diseases, inflammatory bowel disease, kidney disease, liver disease and others.

Necrosis is characterized by cell membrane and organelle disruption, cell swelling and mitochondrial impairment, followed by cell lysis. Also, cell lyses typically are accompanied by an inflammatory response. Some of the underlying biochemical events in this process are now understood and the activity of receptor interacting protein kinase 1 has been shown to be important for cells to undergo necroptosis. Furthermore, this activity is also known to promote the release of inflammatory mediators such as TNF alpha from cells which can induce inflammation and also promote further necroptosis. Therefore, identifying and preparing low molecular weight molecules that prevent necrotic cell death and/or inflammation by inhibiting this or by other mechanisms can provide useful compounds for therapeutic intervention in diseases characterized by necrotic cell death and/or inflammation.

While progress has been made, there remains a need in the art for improved compounds for preventing and treating diseases involving cell death and/or inflammation. The present disclosure provides this and related benefits.

SUMMARY

Provided herein are compounds that are useful as inhibitors of receptor interacting protein kinase 1. The disclosure also provides compositions, including pharmaceutical compositions, kits that include the compounds, and methods of using (or administering) and making the compounds. The disclosure further provides compounds or compositions thereof for use in a method of treating a disease, disorder, or condition that is mediated by receptor interacting protein kinase 1. Moreover, the disclosure provides uses of the compounds or compositions thereof in the manufacture of a medicament for the treatment of a disease, disorder or condition that is mediated by (or mediated, at least in part, by) receptor interacting protein kinase 1.

In certain aspects, provided is a compound of Formula I or a pharmaceutically acceptable salt, deuterated analog, stereoisomer, mixture of stereoisomers, tautomer, or prodrug thereof. In certain aspects, provided is a compound as shown in Table 1 or a pharmaceutically acceptable salt, deuterated analog, stereoisomer, mixture of stereoisomers, tautomer, or prodrug thereof. In certain aspects, provided is a compound as shown in Table 2 or a pharmaceutically acceptable salt, deuterated analog, stereoisomer, mixture of stereoisomers, tautomer, or prodrug thereof. Also provided herein is a pharmaceutical composition comprising a compound as described herein, or a pharmaceutically acceptable salt, deuterated analog, stereoisomer, mixture of stereoisomers, tautomer, or prodrug thereof, and an excipient.

Provided herein are compounds and compositions for use in medicine. In certain embodiments, the compounds and compositions are for use in the treatment of a receptor interacting protein kinase 1-mediated disease or disorder.

Provided herein is a method of treating a receptor interacting protein kinase 1-mediated disease or disorder comprising administering a therapeutically effective amount of a compound or pharmaceutical composition disclosed herein to a subject in need thereof.

In certain embodiments, the disease or disorder is inflammatory bowel disease, Crohn's disease, ulcerative colitis, psoriasis, retinal detachment, retinitis pigmentosa, macular degeneration, pancreatitis (e.g., acute pancreatitis), atopic dermatitis, rheumatoid arthritis, spondyloarthritis, gout, SoJIA, systemic lupus erythematosus, Sjogren's syndrome, systemic scleroderma, anti-phospholipid syndrome, vasculitis, osteoarthritis, non-alcohol steatohepatitis, alcohol steatohepatitis, autoimmune hepatitis autoimmune hepatobiliary diseases, primary sclerosing cholangitis, nephritis, Celiac disease, autoimmune ITP, transplant rejection, ischemia reperfusion injury of solid organs, sepsis, systemic inflammatory response syndrome, cerebrovascular accident, myocardial infarction, Huntington's disease, Alzheimer's disease, Parkinson's disease, allergic diseases, asthma, atopic dermatitis, multiple sclerosis, type I diabetes, Wegener's granulomatosis, pulmonary sarcoidosis, Behcet's disease, interleukin-1 converting enzyme associated fever syndrome, chronic obstructive pulmonary disease, tumor necrosis factor receptor-associated periodic syndrome, atherosclerosis, Guillain-Barre syndrome, chronic inflammatory demyelinating polyneuropathy, necrotizing enterocolitis, tuberous sclerosis, Tangier's Disease, Wohlman's Syndrome, burns, hypoxia, encephalopathy, major depressive disorder, bipolar disorder, delirium, post-operative cognitive impairment, autism, schizophrenia, hidradenitis suppurativa, or peridontitis. In certain embodiments, the disease or disorder is trauma, ischemia, stroke, cardiac infarction, infection, Gaucher's disease, Krabbe disease, sepsis, Parkinson's disease, Alzheimer's disease, amyotrophic lateral sclerosis, Huntington's disease, HIV-associated dementia, retinal degenerative disease, glaucoma, age-related macular degeneration, rheumatoid arthritis, psoriasis, psoriatic arthritis or inflammatory bowel disease. In certain embodiments, the disease or disorder is Alzheimer's disease, amyotrophic lateral sclerosis (ALS/Lou Gehrig's Disease), Friedreich's ataxia, Huntington's disease, Lewy body disease, Parkinson's disease, or spinal muscular atrophy. In certain embodiments, the disease or disorder is brain injury, spinal cord injury, dementia, stroke, Alzheimer's disease, amyotrophic lateral sclerosis (ALS/Lou Gehrig's Disease), Parkinson's disease, Huntington's disease, multiple sclerosis, diabetic neuropathy, polyglutamine (polyQ) diseases, stroke, Fahr disease, Menke's disease, Wilson's disease, cerebral ischemia, or a prion disorder.

DETAILED DESCRIPTION

The following description sets forth exemplary embodiments of the present technology. It should be recognized, however, that such description is not intended as a limitation on the scope of the present disclosure but is instead provided as a description of exemplary embodiments.

1. Definitions

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line or a dashed line drawn through a line in a Formula indicates a specified point of attachment of a group. Unless chemically or structurally required, no directionality or stereochemistry is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In certain embodiments, the term "about" includes the indicated amount ±5%. In certain embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 12 carbon atoms (i.e., $C_{1-12}$ alkyl), 1 to 8 carbon atoms (i.e., $C_{1-8}$ alkyl), 1 to 6 carbon atoms (i.e., $C_{1-6}$ alkyl) or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl and 3-methylpentyl. When an alkyl residue having a specific number of carbons is named by chemical name or identified by molecular formula, all positional isomers having that number of carbons may be encompassed; thus, for example, "butyl" includes n-butyl (i.e., —(CH$_2$)$_3$CH$_3$), sec-butyl (i.e., —CH(CH$_3$)CH$_2$CH$_3$), isobutyl (i.e., —CH$_2$CH (CH$_3$)$_2$) and tert-butyl (i.e., —C(CH$_3$)$_3$); and "propyl" includes n-propyl (i.e., —(CH$_2$)$_2$CH$_3$) and isopropyl (i.e., —CH(CH$_3$)$_2$).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl or aralkyl, the last mentioned group contains the atom by which the moiety is attached to the rest of the molecule.

"Alkenyl" refers to an alkyl group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl) or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl) or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, isopropoxy, n-butoxy, tert-butoxy, sec-butoxy, n-pentoxy, n-hexoxy and 1,2-dimethylbutoxy.

"Alkoxyalkyl" refers to the group "alkyl-O-alkyl".

"Alkylthio" refers to the group "alkyl-S—".

"Acyl" refers to a group —C(O)R, wherein R is hydrogen, alkyl, alkenyl, alkynyl, cycloalkyl, heterocyclyl, aryl, heteroalkyl or heteroaryl; each of which may be optionally substituted, as defined herein. Examples of acyl include formyl, acetyl, cyclohexylcarbonyl, cyclohexylmethyl-carbonyl and benzoyl.

"Amido" refers to both a "C-amido" group which refers to the group —C(O)NR$^y$R$^z$ and an "N-amido" group which refers to the group —NR$^y$C(O)R$^z$, wherein R$^y$ and R$^z$ are independently hydrogen, alkyl, alkenyl, alkynyl, cycloalkyl, heterocyclyl, aryl, heteroalkyl or heteroaryl; each of which may be optionally substituted, as defined herein.

"Amino" refers to the group —NR$^y$R$^z$ wherein R$^y$ and R$^z$ are independently hydrogen, alkyl, alkenyl, alkynyl, cycloalkyl, heterocyclyl, aryl, heteroalkyl or heteroaryl; each of which may be optionally substituted, as defined herein.

"Amidino" refers to —C(NR)(NR$_2$), wherein each R is independently hydrogen, alkyl, alkenyl, alkynyl, cycloalkyl, heterocyclyl, aryl, heteroalkyl or heteroaryl; each of which may be optionally substituted, as defined herein.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_{6-20}$ aryl), 6 to 18 carbon ring atoms (i.e., $C_{6-18}$ aryl), 6 to 12 carbon ring atoms (i.e., $C_{6-12}$ aryl) or 6 to 10 carbon ring atoms (i.e., $C_{6-10}$ aryl). Examples of aryl groups include phenyl, naphthyl, fluorenyl and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Arylalkyl" or "Aralkyl" refers to the group "aryl-alkyl-".

"Carbamoyl" refers to both an "O-carbamoyl" group which refers to the group —O—C(O)NR$^y$R$^z$ and an "N-carbamoyl" group which refers to the group —NR$^y$C(O)OR$^z$, wherein R$^y$ and R$^z$ are independently hydrogen, alkyl, alkenyl, alkynyl, cycloalkyl, heterocyclyl, aryl, heteroalkyl or heteroaryl; each of which may be optionally substituted, as defined herein.

"Carboxyl ester" or "ester" refer to both —OC(O)R and —C(O)OR, wherein R is alkyl, alkenyl, alkynyl, cycloalkyl, heterocyclyl, aryl, heteroalkyl or heteroaryl; each of which may be optionally substituted, as defined herein.

"Cycloalkyl" refers to a saturated or partially unsaturated cyclic alkyl group having a single ring or multiple rings including fused, bridged and spiro ring systems. The term "cycloalkyl" includes cycloalkenyl groups (i.e., the cyclic group having at least one double bond). As used herein, cycloalkyl has from 3 to 20 ring carbon atoms (i.e., $C_{3-20}$ cycloalkyl), 3 to 15 ring carbon atoms (i.e., $C_{3-15}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl) or 3 to 6 ring carbon atoms (i.e., $C_{3-6}$ cycloalkyl). Cycloalkyl also includes "spiro cycloalkyl" when there are two positions for substitution on the same carbon atom. Monocyclic radicals include, for example, cyclopropyl, cyclobutyl, cyclopentyl, cyclohexyl, cycloheptyl and cyclooctyl. Polycyclic radicals include, for example, adamantyl, norbornyl, decalinyl, 7,7-dimethyl-bicyclo[2.2.1]heptanyl and the like. Further, the term cycloalkyl is intended to encompass any non-aromatic ring which may be fused to an aryl ring, regardless of the attachment to the remainder of the molecule.

"Cycloalkylalkyl" refers to the group "cycloalkyl-alkyl-".

"Guanidino" refers to —NRC(NR)(NR$_2$). wherein each R is hydrogen, alkyl, alkenyl, alkynyl, cycloalkyl, heterocyclyl, aryl, heteroalkyl or heteroaryl; each of which may be optionally substituted, as defined herein.

"Imino" refers to a group —C(NR)R, wherein each R is independently hydrogen, alkyl, alkenyl, alkynyl, cycloalkyl, heterocyclyl, aryl, heteroalkyl or heteroaryl; each of which may be optionally substituted, as defined herein.

"Imido" refers to a group —C(O)NRC(O)R, wherein each R is independently hydrogen, alkyl, alkenyl, alkynyl, cycloalkyl, heterocyclyl, aryl, heteroalkyl or heteroaryl; each of which may be optionally substituted, as defined herein.

"Halogen" or "halo" includes fluoro, chloro, bromo and iodo.

"Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include trifluoromethyl, difluoromethyl, trichloromethyl, 2,2,2-trifluoroethyl, 1,2-difluoroethyl, 3-bromo-2-fluoropropyl, 1,2-dibromoethyl and the like.

"Haloalkoxy" refers to an alkoxy group as defined above, wherein one or more hydrogen atoms are replaced by a halogen.

"Hydroxyalkyl" refers to an alkyl group as defined above, wherein one or more hydrogen atoms are replaced by a hydroxy group.

"Heteroalkyl" refers to an alkyl group in which one or more of the carbon atoms (and any associated hydrogen atoms) are each independently replaced with the same or different heteroatomic group, provided the point of attachment to the remainder of the molecule is through a carbon atom. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —S(O)$_2$—, and the like, where R is hydrogen, alkyl, alkenyl, alkynyl, cycloalkyl, heterocyclyl, aryl, heteroalkyl, or heteroaryl; each of which may be optionally substituted, as defined herein. Examples of heteroalkyl groups include —CH$_2$OCH$_3$, —CH$_2$SCH$_3$, and —CH$_2$NRCH$_3$, where R is hydrogen, alkyl, alkenyl, alkynyl, cycloalkyl, heterocyclyl, aryl, heteroalkyl, or heteroaryl; each of which may be optionally substituted, as defined herein. As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group (e.g., a 5-14 membered ring system) having a single ring, multiple rings or multiple fused rings, with one or more ring heteroatoms independently selected from nitrogen, oxygen and sulfur. As used herein, heteroaryl includes 1 to 20 ring carbon atoms (i.e., $C_{1-20}$ heteroaryl), 1 to 13 ring carbon atoms (i.e., $C_{3-12}$ heteroaryl), 3 to 12 ring carbon atoms (i.e., $C_{3-12}$ heteroaryl) or 3 to 8 carbon ring atoms (i.e., $C_{3-8}$ heteroaryl); and 1 to 6 heteroatoms, 1 to 5 heteroatoms, 1 to 4 heteroatoms, 1 to 3 ring heteroatoms, 1 to 2 ring heteroatoms or 1 ring heteroatom independently selected from nitrogen, oxygen and sulfur. Examples of heteroaryl groups include azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl and thiophenyl (i.e., thienyl). Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heteroarylalkyl" refers to the group "heteroaryl-alkyl-".

"Heterocyclyl" refers to a saturated or unsaturated cyclic alkyl group, with one or more ring heteroatoms independently selected from nitrogen, oxygen and sulfur. The term "heterocyclyl" includes heterocycloalkenyl groups (i.e., the heterocyclyl group having at least one double bond), bridged-heterocyclyl groups, fused-heterocyclyl groups and spiro-heterocyclyl groups. A heterocyclyl may be a single ring or multiple rings wherein the multiple rings may be fused, bridged or spiro, and may comprise one or more oxo (C═O) or N-oxide (N—O—) moieties. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms
(i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl) or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms or 1 ring heteroatom independently selected from nitrogen, sulfur or oxygen. Examples of heterocyclyl groups include dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl and 1,1-dioxo-thiomorpholinyl. Examples of the spiro-heterocyclyl rings include bicyclic and tricyclic ring systems, such as 2-oxa-7-azaspiro[3.5]nonanyl, 2-oxa-6-azaspiro[3.4]octanyl and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl and isoindolinyl, where the heterocyclyl can be bound via either ring of the fused system.

"Heterocyclylalkyl" refers to the group "heterocyclyl-alkyl-".

"Oxime" refers to the group —CR(=NOH) wherein R is hydrogen, alkyl, alkenyl, alkynyl, cycloalkyl, heterocyclyl, aryl, heteroalkyl or heteroaryl; each of which may be optionally substituted, as defined herein.

"Sulfonyl" refers to the group —S(O)$_2$R, where R is hydrogen, alkyl, alkenyl, alkynyl, cycloalkyl, heterocyclyl, aryl, heteroalkyl or heteroaryl; each of which may be optionally substituted, as defined herein. Examples of sulfonyl are methylsulfonyl, ethylsulfonyl, phenylsulfonyl and toluenesulfonyl.

"Sulfinyl" refers to the group —S(O)R, where R is hydrogen, alkyl, alkenyl, alkynyl, cycloalkyl, heterocyclyl, aryl, heteroalkyl or heteroaryl; each of which may be optionally substituted, as defined herein. Examples of sulfinyl are methylsulfinyl, ethylsulfinyl, phenylsulfinyl and toluenesulfinyl.

"Sulfonamido" refers to the groups —SO$_2$NRR and —NRSO$_2$R, where each R is independently hydrogen, alkyl, alkenyl, alkynyl, cycloalkyl, heterocyclyl, aryl, heteroalkyl or heteroaryl; each of which may be optionally substituted, as defined herein.

"Alkylsulfonyl" refers to the group —S(O)$_2$R, where R is alkyl.

"Alkylsulfinyl" refers to the group —S(O)R, where R is alkyl.

The terms "optional" or "optionally" means that the subsequently described event or circumstance may or may not occur and that the description includes instances where said event or circumstance occurs and instances in which it does not. Also, the term "optionally substituted" refers to any one or more hydrogen atoms on the designated atom or group may or may not be replaced by a moiety other than hydrogen.

The term "substituted" used herein means any of the above groups (i.e., alkyl, alkenyl, alkynyl, alkylene, alkoxy, haloalkyl, haloalkoxy, cycloalkyl, aryl, heterocyclyl, heteroaryl, and/or heteroalkyl) wherein at least one hydrogen atom is replaced by a bond to a non-hydrogen atom such as, but not limited to alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanadino, halo, haloalkyl, haloalkoxy, hydroxyalkyl, heteroalkyl, heteroaryl, heteroarylalkyl, heterocyclyl, heterocyclylalkyl, hydrazine, hydrazone, imino, imido, hydroxy, oxo, oxime, nitro, sulfonyl, sulfinyl, alkylsulfonyl, alkylsulfinyl, thiocyanate, sulfinic acid, sulfonic acid, sulfonamido, thiol, thioxo, N-oxide, or —Si(R$^{100}$)$_3$ wherein each R$^{100}$ is independently hydrogen, alkyl, alkenyl, alkynyl, heteroalkyl, cycloalkyl, aryl, heteroaryl or heterocyclyl.

The term "substituted" used herein means any of the above groups (i.e., alkyl, alkylene, alkoxy, haloalkoxy, aryl, cycloalkyl, haloalkyl, heterocyclyl, heteroaryl, hydroxylalkyl and/or alkoxyalkyl) wherein at least one hydrogen atom is replaced by a bond to a non-hydrogen atom such as, but not limited to: an alkyl group, a haloalkyl group, a halogen atom such as F, Cl, Br, and I; an alkenyl, a haloalkenyl group, an alkynyl group, a haloalkynyl group, a cyclic group such as an aryl, heteroaryl, cycloalkyl, or heterocyclyl group, an oxygen atom in groups such as hydroxyl groups, alkoxy groups, and ester groups; a sulfur atom in groups such as thiol groups, thioalkyl groups, thiohaloalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, formyl, carboxyl, carbonate, and ester groups; and nitrogen in groups such as imines, oximes, hydrazones, and nitriles.

In certain embodiments, "substituted" includes any of the above alkyl, alkenyl, alkynyl, cycloalkyl, heterocyclyl, aryl or heteroaryl groups in which one or more hydrogen atoms are independently replaced with deuterium, halo, cyano, nitro, azido, oxo, alkyl, alkenyl, alkynyl, haloalkyl, cycloalkyl, heterocyclyl, aryl, heteroaryl, —NR$^g$R$^h$, —NR$^g$C(=O)R$^h$, —NR$^g$C(=O)NR$^g$R$^h$, —NR$^g$C(=O)OR$^h$, —NR$^g$S(=O)$_{1-2}$R$^h$, —C(=O)R$^g$, —C(=O)OR$^g$, —OC(=O)OR$^g$, —OC(=O)R$^g$, —C(=O)NR$^g$R$^h$, —OC(=O)NR$^g$R$^h$, —OR$^g$, —SR$^g$, —S(=O)R$^g$, —S(=O)$_2$R$^g$, —OS(=O)$_{1-2}$R$^g$, —S(=O)$_{1-20}$R$^g$, —NR$^g$S(=O)$_{1-2}$NR$^g$R$^h$, =NSO$_2$R$^g$, =NOR$^g$, —S(=O)$_{1-2}$NR$^g$R$^h$, —SF$_5$, —SCF$_3$ or —OCF$_3$. "Substituted" also means any of the above groups in which one or more hydrogen atoms are replaced with —C(=O)R$^g$, —C(=O)OR$^g$, —C(=O)NR$^g$R$^h$, —CH$_2$SO$_2$R$^g$, —CH$_2$SO$_2$NR$^g$R$^h$. "Substituted" further means any of the above groups in which one or more hydrogen atoms are replaced by —NR$^g$S(=O)$_{1-2}$NR$^g$R$^h$, —CH$_2$S(=O)R$^g$, —CH$_2$S(=O)NR$^g$R$^h$, —OC(=O)OR$^g$, —SF$_5$, —SCF$_3$ or —OCF$_3$. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, and/or heteroarylalkyl group. In the foregoing, $R^g$ and $R^h$ and $R^i$ are the same or different and independently hydrogen, halo, alkyl, alkenyl, alkynyl, alkoxy, thioalkyl, aryl, aralkyl, cycloalkyl, cycloalkylalkyl, haloalkyl, heterocyclyl, heterocyclylalkyl, heteroaryl, and/or heteroarylalkyl, or two of $R^g$ and $R^h$ and $R^i$ are taken together with the atoms to which they are attached to form a heterocyclyl ring optionally substituted with oxo, halo or alkyl optionally substituted with oxo, halo, amino, hydroxyl or alkoxy. In an embodiment, each of said hydrogen, alkyl, alkenyl, alkynyl, alkoxy, thioalkyl, aryl, aralkyl, cycloalkyl, cycloalkylalkyl, haloalkyl, heterocyclyl, heterocyclylalkyl, heteroaryl, and/or heteroarylalkyl are independently optionally substituted with one or more oxo, alkyl, halo, amino, hydroxyl or alkoxy. In addition, each of the foregoing substituents may also be optionally substituted with one or more of the above substituents. In some embodiments, "substituted" means that any one or more hydrogen atoms on a designated atom or group is replaced with one or more substituents other than hydrogen, provided that the designated atom's or group's normal valence is not exceeded.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in certain embodiments, the term "substituted alkyl" refers to an alkyl group having one or more substituents including hydroxy, halo, alkoxy, acyl, oxo, amino, cycloalkyl, heterocyclyl, aryl and heteroaryl. In certain embodiments, the one or more substituents may be further substituted with halo, alkyl, haloalkyl, hydroxy, alkoxy, cycloalkyl, heterocyclyl, aryl or heteroaryl, each of which is substituted. In certain embodiments, the substituents may be further substituted with halo, alkyl, haloalkyl, alkoxy, hydroxy, cycloalkyl, heterocyclyl, aryl or heteroaryl, each of which is unsubstituted.

Any compound or Formula given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$ and $^{125}I$, respectively. Various isotopically labeled compounds of the present disclosure, for example those into which radioactive isotopes such as $^3H$, $^{13}C$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogs" of compounds described herein in which from 1 to n hydrogens attached to a carbon atom is/are replaced by deuterium, in which n is the number of hydrogens in the molecule. Such compounds exhibit increased resistance to metabolism and are thus useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$, $^3H$, $^{11}C$ labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound described herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided are also pharmaceutically acceptable salts, hydrates, solvates, tautomeric forms, stereoisomers and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., HN(alkyl)$_2$), trialkyl amines (i.e., N(alkyl)$_3$), substituted alkyl amines (i.e., $NH_2$(substituted alkyl)), di(substituted alkyl) amines (i.e., HN(substituted alkyl)$_2$), tri(substituted alkyl) amines (i.e., N(substituted alkyl)$_3$), alkenyl amines (i.e., $NH_2$(alkenyl)), dialkenyl amines (i.e., HN(alkenyl)$_2$), trialkenyl amines (i.e., N(alkenyl)$_3$), substituted alkenyl amines (i.e., $NH_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., $NH_2$(cycloalkyl), HN(cycloalkyl)$_2$, N(cycloalkyl)$_3$), mono-, di- or tri-arylamines (i.e., $NH_2$(aryl), HN(aryl)$_2$, N(aryl)$_3$) or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine and the like.

The term "hydrate" refers to the complex formed by the combining of a compound described herein and water.

A "solvate" refers to an association or complex of one or more solvent molecules and a compound of the disclosure. Examples of solvents that form solvates include, but are not limited to, water, isopropanol, ethanol, methanol, dimethylsulfoxide, ethylacetate, acetic acid and ethanolamine.

Some of the compounds exist as tautomers. Tautomers are in equilibrium with one another. For example, amide containing compounds may exist in equilibrium with imidic acid tautomers. Regardless of which tautomer is shown and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The compounds disclosed herein, or their pharmaceutically acceptable salts include an asymmetric center and may thus give rise to enantiomers, diastereomers, and other stereoisomeric forms that may be defined, in terms of absolute stereochemistry, as (R)- or (S)- or, as (D)- or (L)- for amino acids. The disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are nonsuperimposable mirror images of one another.

"Diastereoisomers" are stereoisomers that have at least two asymmetric atoms, but which are not mirror-images of each other.

"Prodrugs" means any compound which releases an active parent drug according to a Formula described herein in vivo when such prodrug is administered to a mammalian subject. Prodrugs of a compound described herein are prepared by modifying functional groups present in the compound described herein in such a way that the modifications may be cleaved in vivo to release the parent compound. Prodrugs may be prepared by modifying functional groups present in the compounds in such a way that the modifications are cleaved, either in routine manipulation or in vivo, to the parent compounds. Prodrugs include compounds described herein wherein a hydroxy, amino, carboxyl or sulfhydryl group in a compound described herein is bonded to any group that may be cleaved in vivo to regenerate the free hydroxy, amino or sulfhydryl group, respectively. Examples of prodrugs include, but are not limited to esters (e.g., acetate, formate and benzoate derivatives), amides, guanidines, carbamates (e.g., N,N-dimethylaminocarbonyl) of hydroxy functional groups in compounds described herein and the like. Preparation, selection and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

As used herein, "pharmaceutically acceptable carrier" or "pharmaceutically acceptable excipient" or "excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "necrotic cell disease" refers to diseases associated with or caused by cellular necrosis. Exemplary necrotic cell diseases include, but are not limited to, acute diseases such as trauma, ischemia, stroke, cardiac infarction, anthrax lethal toxin induced septic shock, sepsis, cell death induced by LPS and HIV induced T-cell death leading to immunodeficiency. The term "necrotic cell disease" also includes but is not limited to chronic neurodegenerative diseases, such as Parkinson's disease, Huntington's disease, amyotrophic lateral sclerosis, Alzheimer's disease, infectious encelopathies, dementia such as HIV associated dementia. The term "necrotic cell disease" also includes but is not limited to diseases such as inflammatory bowel disease and acute and chronic kidney disease which are characterized by inflammation and cell death.

The chemical names used herein are generated using the MarvinSketch Version 6.1.6 (ChemAxon) or the ChemDraw Ultra Version 13.0 software naming programs.

2. Compounds

Provided are compounds of Formula I:

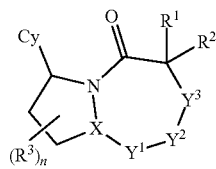

I or a pharmaceutically acceptable salt, deuterated analog, stereoisomer, mixture of stereoisomers, tautomer, or prodrug thereof, wherein:

X is N or $CR^4$, wherein $R^4$ is H or optionally substituted alkyl;

Cy is optionally substituted cycloalkyl, optionally substituted heterocyclyl, optionally substituted aryl, or optionally substituted heteroaryl;

$Y^1$, $Y^2$, and $Y^3$ are independently $CR^5R^6$, S, SO, $SO_2$, O, or $NR^7$;

$R^1$ is cyano, optionally substituted alkyl, optionally substituted alkenyl, optionally substituted alkynyl, optionally substituted alkoxy, —$SOR^8$, —$SOR^8$, —$SO_2R^8$, optionally substituted cycloalkyl, optionally substituted heterocyclyl, optionally substituted aryl, or optionally substituted heteroaryl;

or $R^1$ and $Y^3$ together form an optionally substituted heterocyclyl;

$R^2$ is cyano, hydrogen, halo, optionally substituted alkyl, optionally substituted alkenyl, optionally substituted alkynyl, optionally substituted cycloalkyl, optionally substituted heterocyclyl, optionally substituted aryl, or optionally substituted heteroaryl; or $R^1$ and $R^2$ together form an optionally substituted cycloalkyl or optionally substituted heterocyclyl;

each $R^3$ is independently halo, cyano, or optionally substituted alkyl; or two $R^3$ together form an optionally substituted cycloalkyl or an optionally substituted heterocyclyl;

$R^5$ and $R^6$ are independently cyano, halo, hydrogen, hydroxyl, optionally substituted alkyl, optionally substituted alkenyl, optionally substituted alkynyl, optionally substituted alkoxy, —SH, —$SR^8$, —$SOR^8$, —$SO_2R^8$, optionally substituted cycloalkyl, optionally substituted heterocyclyl, optionally substituted aryl, or optionally substituted heteroaryl; or $R^5$ and $R^6$ together with the carbon atom to which they are both attached form an optionally substituted cycloalkyl, optionally substituted heterocyclyl, or oxo; or any two $R^5$ groups attached to adjacent carbon atoms together form an optionally substituted cycloalkyl or optionally substituted heterocyclyl;

$R^7$ is hydrogen or optionally substituted alkyl;

$R^8$ is optionally substituted alkyl; and n is 0, 1, 2, 3, 4, or 5.

In certain embodiments, Cy is optionally substituted aryl or optionally substituted heteroaryl.

In certain embodiments, Cy is optionally substituted phenyl, optionally substituted pyridyl, optionally substituted pyrimidine, or optionally substituted pyrazine. In certain embodiments, Cy is optionally substituted phenyl, optionally substituted pyridyl, or optionally substituted pyrazine.

In certain embodiments, Cy is independently optionally substituted with one or more $R^{10}$, wherein $R^{10}$ is independently cyano, halo, nitro, oxo, —$OR^{11}$, —$SR^{11}$, —$SF_5$, —$NR^{11}R^{12}$, —$C(=O)R^{13}$, —$C(=O)OR^{11}$, —$OC(=O)OR^{11}$, —$OC(=O)R^{13}$, —$C(=O)NR^{11}R^{12}$, —$OC(=O)NR^{11}R^{12}$, —$NR^{11}C(=O)NR^{11}R^{12}$, —$S(=O)_{1-2}R^{13}$, —$S(=O)_{1-2}NR^{11}R^{12}$, —$NR^{11}S(=O)_{1-2}R^{13}$, —$NR^{11}S(=O)_{1-2}NR^{11}R^{12}$, —$NR^{11}C(=O)R^{13}$, —$NR^{11}C(=O)OR^{12}$, —C=$NOR^{11}$, $C_{1-12}$ alkyl, $C_{2-12}$ alkenyl, $C_{2-12}$ alkynyl, $C_{3-10}$ cycloalkyl, heterocyclyl, aryl, or heteroaryl; wherein the $C_{1-12}$ alkyl, $C_{2-12}$ alkenyl and $C_{2-12}$ alkynyl are optionally substituted with one or more halo; the $C_{3-10}$ cycloalkyl, heterocyclyl, aryl, heteroaryl are independently optionally substituted with one or more cyano, halo, nitro, oxo, —$OR^{14}$, —$SR^{14}$, —$SF_5$, —$NR^{14}R^{15}$, —$S(=O)_{1-2}R^{16}$, —$S(=O)_{1-2}NR^{14}R^{15}$, —$NR^{14}S(=O)_{1-2}R^{16}$, or $R^{16}$;

$R^{11}$, $R^{12}$, $R^{14}$, and $R^{15}$ are independently H or $C_{1-12}$ alkyl optionally substituted with one or more halo, or two of $R^{11}$ and $R^{12}$ or two of $R^{14}$ and $R^{15}$ together with the atoms to which they are attached form a heterocyclyl optionally substituted with one or more halo or $C_{1-12}$ alkyl optionally substituted with one or more halo; and $R^{13}$ and $R^{16}$ are independently $C_{1-12}$ alkyl optionally substituted with one or more halo.

In certain embodiments, Cy is 5-cyano-pyrid-3-yl, 5-fluoro-pyrid-3-yl, 3-fluorophenyl, 3-cyanophenyl, 3-cyano-5-fluorophenyl, 5-methylpyrazin-2-yl, 3,4-difluorophenyl, or 3,5-difluorophenyl.

In certain embodiments, provided is a compound of formula I-1:

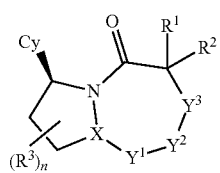

I-1 or a pharmaceutically acceptable salt, deuterated analog, stereoisomer, mixture of stereoisomers, tautomer, or prodrug thereof, where Cy, n, X, $Y^1$, $Y^2$, $Y^3$, $R^1$ and $R^2$ are as defined herein.

In certain embodiments, provided is a compound of formula Ia:

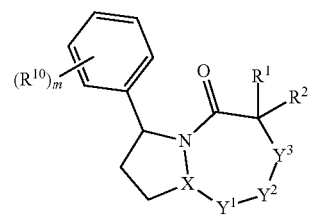

Ia or a pharmaceutically acceptable salt, deuterated analog, stereoisomer, mixture of stereoisomers, tautomer, or prodrug thereof, wherein:

X is N or $CR^4$, wherein $R^4$ is H or optionally substituted alkyl;

$Y^1$, $Y^2$, and $Y^3$ are independently $CR^5R^6$, S, SO, $SO_2$, O, or $NR^7$;

$R^1$ is cyano, optionally substituted alkyl, optionally substituted alkenyl, optionally substituted alkynyl, optionally substituted alkoxy, $-SR^8$, $-SOR^8$, $-SO_2R^8$, optionally substituted cycloalkyl, optionally substituted heterocyclyl, optionally substituted aryl, or optionally substituted heteroaryl;

$R^2$ is cyano, hydrogen, halo, optionally substituted alkyl, optionally substituted alkenyl, optionally substituted alkynyl, optionally substituted cycloalkyl, optionally substituted heterocyclyl, optionally substituted aryl, or optionally substituted heteroaryl; or $R^1$ and $R^2$ together form an optionally substituted cycloalkyl or optionally substituted heterocyclyl;

$R^3$ is independently halo, cyano, or optionally substituted alkyl;

$R^5$ and $R^6$ are independently cyano, halo, hydrogen, hydroxyl, optionally substituted alkyl, optionally substituted alkenyl, optionally substituted alkynyl, optionally substituted alkoxy, $-SH$, $-SR^8$, $-SOR^8$, $-SO_2R^8$, optionally substituted cycloalkyl, optionally substituted heterocyclyl, optionally substituted aryl, or optionally substituted heteroaryl; or $R^5$ and $R^6$ together with the carbon atom to which they are both attached form an optionally substituted cycloalkyl, optionally substituted heterocyclyl, or oxo; or $R^5$ and $R^6$ attached to adjacent carbon atoms together form an optionally substituted cycloalkyl or optionally substituted heterocyclyl;

$R^7$ is hydrogen or optionally substituted alkyl;

$R^8$ is optionally substituted alkyl;

$R^{10}$ is independently cyano, halo, nitro, $-OR^{11}$, $-SR^{11}$, $-SF_5$, $-NR^{11}R^{12}$, $-C(=O)R^{13}$, $-C(=O)OR^{11}$, $-OC(=O)OR^{11}$, $-OC(=O)R^{13}$, $-C(=O)NR^{11}R^{12}$, $-OC(=O)NR^{11}R^{12}$, $-NR^{11}C(=O)NR^{11}R^{12}$, $-S(=O)_{1-2}R^{13}$, $-S(=O)_{1-2}NR^{11}R^{12}$, $-NR^{11}S(=O)_{1-2}R^{13}$, $-NR^{11}S(=O)_{1-2}NR^{11}R^{12}$, $-NR^{11}C(=O)R^{13}$, $-NR^{11}C(=O)OR^{12}$, $-C=NOR^{11}$, $C_{1-12}$ alkyl, $C_{2-12}$ alkenyl, $C_{2-12}$ alkynyl, $C_{3-10}$ cycloalkyl, heterocyclyl, aryl, or heteroaryl; wherein the $C_{1-12}$ alkyl, $C_{2-12}$ alkenyl and $C_{2-12}$ alkynyl are optionally substituted with one or more halo; the $C_{3-10}$ cycloalkyl, heterocyclyl, aryl, heteroaryl are independently optionally substituted with one or more cyano, halo, nitro, oxo, $-OR^{14}$, $-SR^{14}$, $-SF_5$, $-NR^{14}R^{15}$, $-S(=O)_{1-2}R^{16}$, $-S(=O)_{1-2}NR^{14}R^{15}$, $-NR^{14}S(=O)_{1-2}R^{16}$, or $R^{16}$;

$R^{11}$, $R^{12}$, $R^{14}$, and $R^{15}$ are independently H or $C_{1-12}$ alkyl optionally substituted with one or more halo, or two of $R^{11}$ and $R^{12}$ or two of $R^{14}$ and $R^{15}$ together with the atoms to which they are attached form a heterocyclyl optionally substituted with one or more halo or $C_{1-12}$ alkyl optionally substituted with one or more halo;

$R^{13}$ and $R^{16}$ are independently $C_{1-12}$ alkyl optionally substituted with one or more halo; and m is 0, 1, 2, 3, 4, or 5.

In certain embodiments, provided is a compound of formula Ia-1:

Ia-1

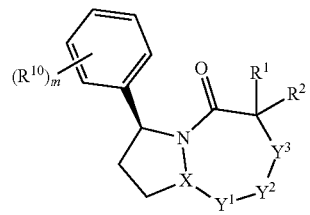

or a pharmaceutically acceptable salt, deuterated analog, stereoisomer, mixture of stereoisomers, tautomer, or prodrug thereof, where $R^{10}$, m, X, $Y^1$, $Y^2$, $Y^3$, $R^1$ and $R^2$ are as defined herein.

In certain embodiments, provided is a compound of formula Ib:

Ib

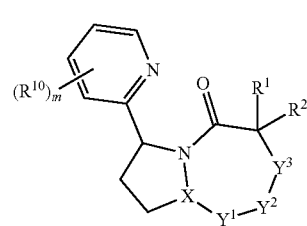

or a pharmaceutically acceptable salt, deuterated analog, stereoisomer, mixture of stereoisomers, tautomer, or prodrug thereof, wherein:

X is N or $CR^4$, wherein $R^4$ is H or optionally substituted alkyl;

$Y^1$, $Y^2$, and $Y^3$ are independently $CR^5R^6$, S, SO, $SO_2O$, or $NR^7$;

$R^1$ is cyano, optionally substituted alkyl, optionally substituted alkenyl, optionally substituted alkynyl, optionally substituted alkoxy, $-SR^8$, $-SOR^8$, $-SO_2R^8$, optionally substituted cycloalkyl, optionally substituted heterocyclyl, optionally substituted aryl, or optionally substituted heteroaryl;

$R^2$ is cyano, hydrogen, halo, optionally substituted alkyl, optionally substituted alkenyl, optionally substituted alkynyl, optionally substituted cycloalkyl, optionally substituted heterocyclyl, optionally substituted aryl, or optionally substituted heteroaryl; or $R^1$ and $R^2$ together form an optionally substituted cycloalkyl or optionally substituted heterocyclyl;

$R^3$ is independently halo, cyano, or optionally substituted alkyl;

$R^5$ and $R^6$ are independently cyano, halo, hydrogen, hydroxyl, optionally substituted alkyl, optionally substituted alkenyl, optionally substituted alkynyl, optionally substituted alkoxy, $-SH$, $-SR^8$, $-SOR^8$, $-SO_2R^8$, optionally substituted cycloalkyl, optionally substituted heterocyclyl, optionally substituted aryl, or optionally substituted heteroaryl; or $R^5$ and $R^6$ together with the carbon atom to which they are both attached form an optionally substituted cycloalkyl, optionally substituted heterocyclyl, or oxo; or $R^5$ and $R^6$ attached to adjacent carbon atoms together form an optionally substituted cycloalkyl or optionally substituted heterocyclyl;

$R^7$ is hydrogen or optionally substituted alkyl;

$R^8$ is optionally substituted alkyl;

$R^{10}$ is independently cyano, halo, nitro, —$OR^{11}$, —$SR^{11}$, —$SF_5$, —$NR^{11}R^{12}$, —$C(=O)R^{13}$, —$C(=O)OR^{11}$, —$OC(=O)OR^{11}$, $OC(=O)R^{13}$, —$C(=O)NR^{11}R^{12}$, —$OC(=O)NR^{11}R^{12}$, —$NR^{11}C(=O)NR^{11}R^{11}$, —$S(=O)_{1-2}R^{13}$, —$S(=O)_{1-2}NR^{11}R^{12}$, —$NR^{11}S(=O)_{1-2}R^{13}$, —$NR^{11}S(=O)_{1-2}NR^{11}R^{12}$, —$NR^{11}C(=O)R^{13}$, —$NR^{11}C(=O)OR^{12}$, —C=$NOR^{11}$, $C_{1-12}$ alkyl, $C_{2-12}$ alkenyl, $C_{2-12}$ alkynyl, $C_{3-10}$ cycloalkyl, heterocyclyl, aryl, or heteroaryl; wherein the $C_{1-12}$ alkyl, $C_{2-12}$ alkenyl and $C_{2-12}$ alkynyl are optionally substituted with one or more halo; the $C_{3-10}$ cycloalkyl, heterocyclyl, aryl, heteroaryl are independently optionally substituted with one or more cyano, halo, nitro, oxo, —$OR^{14}$, —$SR^{14}$, —$SF_5$, —$NR^{14}R^{15}$, —$S(=O)_{1-2}R^{16}$, —$S(=O)_{1-2}NR^{14}R^{15}$, —$NR^{14}S(=O)_{1-2}R^{16}$, or $R^{16}$;

$R^{11}$, $R^{12}$, $R^{14}$, and $R^{15}$ are independently H or $C_{1-12}$ alkyl optionally substituted with one or more halo, or two of $R^{11}$ and $R^{12}$ or two of $R^{14}$ and $R^{15}$ together with the atoms to which they are attached form a heterocyclyl optionally substituted with one or more halo or $C_{1-12}$ alkyl optionally substituted with one or more halo;

$R^{13}$ and $R^{16}$ are independently $C_{1-12}$ alkyl optionally substituted with one or more halo; and m is 0, 1, 2, 3, 4, or 5.

In certain embodiments, provided is a compound of formula Ib-1:

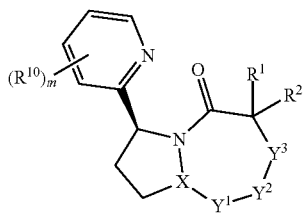

Ib-1 or a pharmaceutically acceptable salt, deuterated analog, stereoisomer, mixture of stereoisomers, tautomer, or prodrug thereof, where $R^{10}$, m, $Y^1$, $Y^2$, $Y^3$, $R^1$ and $R^2$ are as defined herein.

In certain embodiments, provided is a compound of formula Ic:

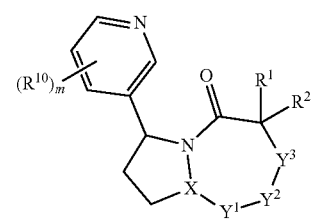

Ic or a pharmaceutically acceptable salt, deuterated analog, stereoisomer, mixture of stereoisomers, tautomer, or prodrug thereof, wherein:

X is N or $CR^4$, wherein $R^4$ is H or optionally substituted alkyl;

$Y^1$, $Y^2$, and $Y^3$ are independently $CR^5R^6$, S, SO, $SO_2$, O, or $NR^7$;

$R^1$ is cyano, optionally substituted alkyl, optionally substituted alkenyl, optionally substituted alkynyl, optionally substituted alkoxy, —$SR^8$, —$SOR^8$, —$SO_2R^8$, optionally substituted cycloalkyl, optionally substituted heterocyclyl, optionally substituted aryl, or optionally substituted heteroaryl;

$R^2$ is cyano, hydrogen, halo, optionally substituted alkyl, optionally substituted alkenyl, optionally substituted alkynyl, optionally substituted cycloalkyl, optionally substituted heterocyclyl, optionally substituted aryl, or optionally substituted heteroaryl; or $R^1$ and $R^2$ together form an optionally substituted cycloalkyl or optionally substituted heterocyclyl;

$R^3$ is independently halo, cyano, or optionally substituted alkyl;

$R^5$ and $R^6$ are independently cyano, halo, hydrogen, hydroxyl, optionally substituted alkyl, optionally substituted alkenyl, optionally substituted alkynyl, optionally substituted alkoxy, —SH, —$SR^8$, —$SOR^8$, —$SO_2R^8$, optionally substituted cycloalkyl, optionally substituted heterocyclyl, optionally substituted aryl, or optionally substituted heteroaryl; or $R^5$ and $R^6$ together with the carbon atom to which they are both attached form an optionally substituted cycloalkyl, optionally substituted heterocyclyl, or oxo; or $R^5$ and $R^6$ attached to adjacent carbon atoms together form an optionally substituted cycloalkyl or optionally substituted heterocyclyl;

$R^7$ is hydrogen or optionally substituted alkyl;

$R^8$ is optionally substituted alkyl;

$R^{10}$ is independently cyano, halo, nitro, —$OR^{11}$, —$SR^{11}$, —$SF_5$, —$NR^{11}R^{12}$, —$C(=O)R^{13}$, —$C(=O)OR^{11}$, —$OC(=O)OR^{11}$, —$OC(=O)R^{13}$, —$C(=O)NR^{11}R^{12}$, —$OC(=O)NR^{11}R^{12}$, —$NR^{11}C(=O)NR^{11}R^{12}$, —$S(=O)_{1-2}R^{13}$, —$S(=O)_{1-2}NR^{11}R^{12}$, —$NR^{11}S(=O)_{1-2}R^{13}$, —$NR^{11}S(=O)_{1-2}NR^{11}R^{12}$, —$NR^{11}C(=O)R^{13}$, —$NR^{11}C(=O)OR^{12}$, —C=$NOR^{11}$, $C_{1-12}$ alkyl, $C_{2-12}$ alkenyl, $C_{2-12}$ alkynyl, $C_{3-10}$ cycloalkyl, heterocyclyl, aryl, or heteroaryl; wherein the $C_{1-12}$ alkyl, $C_{2-12}$ alkenyl and $C_{2-12}$ alkynyl are optionally substituted with one or more halo; the $C_{3-10}$ cycloalkyl, heterocyclyl, aryl, heteroaryl are independently optionally substituted with one or more cyano, halo, nitro, oxo, —$OR^{14}$, —$SR^{14}$, —$SF_5$, —$NR^{14}R^{15}$, —$S(=O)_{1-2}R^{16}$, —$S(=O)_{1-2}NR^{14}R^{15}$, —$NR^{14}S(=O)_{1-2}R^{16}$, or $R^{16}$;

$R^{11}$, $R^{12}$, $R^{14}$, and $R^{15}$ are independently H or $C_{1-12}$ alkyl optionally substituted with one or more halo, or two of $R^{11}$ and $R^{12}$ or two of $R^{14}$ and $R^{15}$ together with the atoms to which they are attached form a heterocyclyl optionally substituted with one or more halo or $C_{1-12}$ alkyl optionally substituted with one or more halo;

$R^{13}$ and $R^{16}$ are independently $C_{1-12}$ alkyl optionally substituted with one or more halo; and m is 0, 1, 2, 3, 4, or 5.

In certain embodiments, provided is a compound of formula Ic-1:

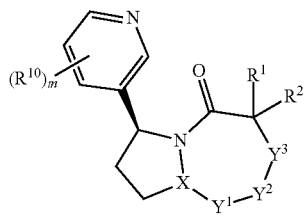

Ic-1 or a pharmaceutically acceptable salt, deuterated analog, stereoisomer, mixture of stereoisomers, tautomer, or prodrug thereof, where $R^{10}$, m, X, $Y^1$, $Y^2$, $Y^3$, $R^1$ and $R^2$ are as defined herein.

In certain embodiments, provided is a compound of formula Id:

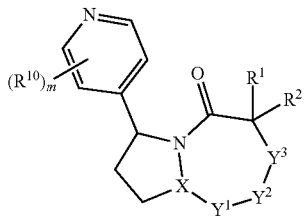

or a pharmaceutically acceptable salt, deuterated analog, stereoisomer, mixture of stereoisomers, tautomer, or prodrug thereof, wherein:

X is N or $CR^4$, wherein $R^4$ is H or optionally substituted alkyl;

$Y^1$, $Y^2$, and $Y^3$ are independently $CR^5R^6$, S, SO, $SO_2$, O, or $NR^7$;

$R^1$ is cyano, optionally substituted alkyl, optionally substituted alkenyl, optionally substituted alkynyl, optionally substituted alkoxy, —$SR^8$, —$SOR^8$, —$SO_2R^8$, optionally substituted cycloalkyl, optionally substituted heterocyclyl, optionally substituted aryl, or optionally substituted heteroaryl;

$R^2$ is cyano, hydrogen, halo, optionally substituted alkyl, optionally substituted alkenyl, optionally substituted alkynyl, optionally substituted cycloalkyl, optionally substituted heterocyclyl, optionally substituted aryl, or optionally substituted heteroaryl; or $R^1$ and $R^2$ together form an optionally substituted cycloalkyl or optionally substituted heterocyclyl;

$R^3$ is independently halo, cyano, or optionally substituted alkyl;

$R^5$ and $R^6$ are independently cyano, halo, hydrogen, hydroxyl, optionally substituted alkyl, optionally substituted alkenyl, optionally substituted alkynyl, optionally substituted alkoxy, —SH, —$SR^8$, —$SOR^8$, —$SO_2R^8$, optionally substituted cycloalkyl, optionally substituted heterocyclyl, optionally substituted aryl, or optionally substituted heteroaryl; or $R^5$ and $R^6$ together with the carbon atom to which they are both attached form an optionally substituted cycloalkyl, optionally substituted heterocyclyl, or oxo; or $R^5$ and $R^6$ attached to adjacent carbon atoms together form an optionally substituted cycloalkyl or optionally substituted heterocyclyl;

$R^7$ is hydrogen or optionally substituted alkyl;

$R^8$ is optionally substituted alkyl;

$R^{10}$ is independently cyano, halo, nitro, —$OR^{11}$, —$SR^{11}$, —$SF_5$, —$NR^{11}R^{12}$, —$(C(=O)R^{13}$, —$C(=O)OR^{11}$, —$OC(=O)OR^{11}$, —$OC(=O)R^{13}$, —$C(=O)NR^{11}R^{12}$, —$OC(=O)NR^{11}R^{12}$, —$NR^{11}C(=O)NR^{11}R^{12}$, —$S(=O)_{1-2}R^{13}$, —$S(=O)_{1-2}NR^{11}R^{12}$, —$NR^{11}S(=O)_{1-2}R^{13}$, —$NR^{11}S(=O)_{1-2}NR^{11}R^{12}$, —$NR^{11}C(=O)R^{13}$, —$NR^{11}C(=O)OR^{12}$, —$C=NOR^{11}$, $C_{1-12}$ alkyl, $C_{2-12}$ alkenyl, $C_{2-12}$ alkynyl, $C_{3-10}$ cycloalkyl, heterocyclyl, aryl, or heteroaryl; wherein the $C_{1-12}$ alkyl, $C_{2-12}$ alkenyl and $C_{2-12}$ alkynyl are optionally substituted with one or more halo; the $C_{3-10}$ cycloalkyl, heterocyclyl, aryl, heteroaryl are independently optionally substituted with one or more cyano, halo, nitro, oxo, —$OR^{14}$, —$SR^{14}$, —$SF_5$, —$NR^{14}R^{15}$, —$S(=O)_{1-2}R^{16}$, —$S(=O)^{14}R^{15}$, —$NR^{14}S(=O)_{1-2}R^{16}$, or $R^{16}$;

$R^{11}$, $R^{12}$, $R^{14}$ and $R^{15}$ are independently H or $C_{1-12}$ alkyl optionally substituted with one or more halo, or two of $R^{11}$ and $R^{12}$ or two of $R^{14}$ and $R^{15}$ together with the atoms to which they are attached form a heterocyclyl optionally substituted with one or more halo or $C_{1-12}$ alkyl optionally substituted with one or more halo;

$R^{13}$ and $R^{16}$ are independently $C_{1-12}$ alkyl optionally substituted with one or more halo; and m is 0, 1, 2, 3, 4, or 5.

In certain embodiments, provided is a compound of formula Id-1:

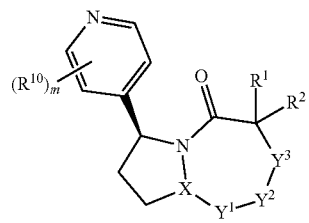

or a pharmaceutically acceptable salt, deuterated analog, stereoisomer, mixture of stereoisomers, tautomer, or prodrug thereof, where $R^{10}$, m, X, $Y^1$, $Y^2$, $Y^3$, $R^1$ and $R^2$ are as defined herein.

In certain embodiments, provided is a compound of formula Ie:

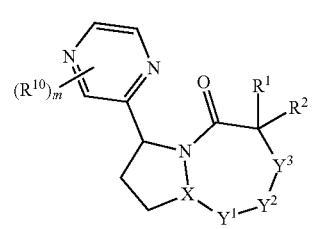

or a pharmaceutically acceptable salt, deuterated analog, stereoisomer, mixture of stereoisomers, tautomer, or prodrug thereof, wherein:

X is N or $CR^4$, wherein $R^4$ is H or optionally substituted alkyl;

$Y^1$, $Y^2$, and $Y^3$ are independently $CR^5R^6$, S, SO, $SO_2$, O, or $NR^7$;

$R^1$ is cyano, optionally substituted alkyl, optionally substituted alkenyl, optionally substituted alkynyl, optionally substituted alkoxy, —$SR^8$, —$SOR^8$, —$SO_2R^8$, optionally substituted cycloalkyl, optionally substituted heterocyclyl, optionally substituted aryl, or optionally substituted heteroaryl;

$R^2$ is cyano, hydrogen, halo, optionally substituted alkyl, optionally substituted alkenyl, optionally substituted alkynyl, optionally substituted cycloalkyl, optionally substituted heterocyclyl, optionally substituted aryl, or optionally substituted heteroaryl; or $R^1$ and $R^2$ together form an optionally substituted cycloalkyl or optionally substituted heterocyclyl;

$R^3$ is independently halo, cyano, or optionally substituted alkyl;

$R^5$ and $R^6$ are independently cyano, halo, hydrogen, hydroxyl, optionally substituted alkyl, optionally substituted alkenyl, optionally substituted alkynyl, optionally substituted alkoxy, —SH, —$SR^8$, —$SOR^8$, —$SO_2R^8$, optionally substituted cycloalkyl, optionally substituted heterocyclyl, optionally substituted aryl, or optionally substituted heteroaryl; or $R^5$ and $R^6$ together with the carbon atom to which they are both attached form an optionally substituted cycloalkyl, optionally substituted heterocyclyl, or oxo; or $R^5$ and $R^6$ attached to adjacent carbon atoms together form an optionally substituted cycloalkyl or optionally substituted heterocyclyl;

$R^7$ is hydrogen or optionally substituted alkyl;

$R^8$ is optionally substituted alkyl;

$R^{10}$ is independently cyano, halo, nitro, —$OR^{11}$, —$SR^{11}$, —$SF_5$, —$NR^{11}R^{12}$, —$C(=O)R^{13}$, —$C(=O)OR^{11}$, —$OC(=O)OR^{11}$, —$OC(=O)R^{13}$, —$C(=O)NR^{11}R^{12}$, —$OC(=O)NR^{11}R^{12}$, —$NR^{11}C(=O)NR^{11}R^{12}$, —$S(=O)_{1-2}R^{13}$, —$S(=O)_{1-2}NR^{11}R^{12}$, —$NR^{11}S(=O)_{1-2}R^{13}$, —$NR^{11}S(=O)_{1-2}NR^{11}R^{12}$, —$NR^{11}C(=O)R^{13}$, —$NR^{11}C(=O)OR^{12}$, —$C=NOR^{11}$, $C_{1-2}$ alkyl, $C_{2-12}$ alkenyl, $C_{2-12}$ alkynyl, $C_{3-10}$ cycloalkyl, heterocyclyl, aryl, or heteroaryl; wherein the $C_{1-12}$ alkyl, $C_{2-12}$ alkenyl and $C_{2-12}$ alkynyl are optionally substituted with one or more halo; the $C_{3-10}$ cycloalkyl, heterocyclyl, aryl, heteroaryl are independently optionally substituted with one or more cyano, halo, nitro, oxo, —$OR^{14}$, —$SR^{14}$, —$SF_5$, —$NR^{14}R^{15}$, —$S(=O)_{1-2}R^{16}$, —$S(=O)_{1-2}NR^{14}R^{15}$, —$NR^{14}S(=O)_{1-2}R^{16}$, or $R^{16}$;

$R^{11}$, $R^{12}$, $R^{14}$, and $R^{15}$ are independently H or $C_{1-12}$ alkyl optionally substituted with one or more halo, or two of $R^{11}$ and $R^{12}$ or two of $R^{14}$ and $R^{15}$ together with the atoms to which they are attached form a heterocyclyl optionally substituted with one or more halo or $C_{1-12}$ alkyl optionally substituted with one or more halo;

$R^{13}$ and $R^{16}$ are independently $C_{1-12}$ alkyl optionally substituted with one or more halo; and m is 0, 1, 2, 3, 4, or 5.

In certain embodiments, provided is a compound of formula Ie-1:

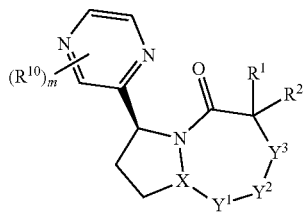

Ie-1 or a pharmaceutically acceptable salt, deuterated analog, stereoisomer, mixture of stereoisomers, tautomer, or prodrug thereof, where $R^{10}$, m, X, $Y^1$, $Y^2$, $Y^3$, $R^1$ and $R^2$ are as defined herein.

In certain embodiments, provided is a compound of formula If:

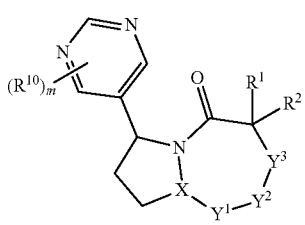

If or a pharmaceutically acceptable salt, deuterated analog, stereoisomer, mixture of stereoisomers, tautomer, or prodrug thereof, wherein:

X is N or $CR^4$, wherein $R^4$ is H or optionally substituted alkyl;

$Y^1$, $Y^2$, and $Y^3$ are independently $CR^5R^6$, S, SO, $SO_2$, O, or $NR^7$;

$R^1$ is cyano, optionally substituted alkyl, optionally substituted alkenyl, optionally substituted alkynyl, optionally substituted alkoxy, —$SR^8$, —$SOR^8$, —$SO_2R^8$, optionally substituted cycloalkyl, optionally substituted heterocyclyl, optionally substituted aryl, or optionally substituted heteroaryl;

$R^2$ is cyano, hydrogen, halo, optionally substituted alkyl, optionally substituted alkenyl, optionally substituted alkynyl, optionally substituted cycloalkyl, optionally substituted heterocyclyl, optionally substituted aryl, or optionally substituted heteroaryl; or $R^1$ and $R^2$ together form an optionally substituted cycloalkyl or optionally substituted heterocyclyl;

$R^3$ is independently halo, cyano, or optionally substituted alkyl;

$R^5$ and $R^6$ are independently cyano, halo, hydrogen, hydroxyl, optionally substituted alkyl, optionally substituted alkenyl, optionally substituted alkynyl, optionally substituted alkoxy, —SH, —$SR^8$, —$SOR^8$, —$SO_2R^8$, optionally substituted cycloalkyl, optionally substituted heterocyclyl, optionally substituted aryl, or optionally substituted heteroaryl; or $R^5$ and $R^6$ together with the carbon atom to which they are both attached form an optionally substituted cycloalkyl, optionally substituted heterocyclyl, or oxo; or $R^5$ and $R^6$ attached to adjacent carbon atoms together form an optionally substituted cycloalkyl or optionally substituted heterocyclyl;

$R^7$ is hydrogen or optionally substituted alkyl;

$R^8$ is optionally substituted alkyl;

$R^{10}$ is independently cyano, halo, nitro, —$OR^{11}$, —$SR^{11}$, —$SF_5$, —$NR^{11}R^{12}$, —$C(=O)R^{13}$, —$C(=O)OR^{11}$, —$OC(=O)OR^{11}$, —$OC(=O)R^{13}$, —$C(=O)NR^{11}R^{12}$, —$OC(=O)NR^{11}R^{12}$, —$NR^{11}C(=O)NR^{11}R^{12}$, —$S(=O)_{1-2}R^{13}$, —$S(=O)_{1-2}NR^{11}R^{12}$, —$NR^{11}S(=O)_{1-2}R^{13}$, —$NR^{11}S(=O)_{1-2}NR^{11}R^{12}$, —$NR^{11}C(=O)R^{13}$, —$NR^{11}C(=O)OR^{12}$, —$C=NOR^{11}$, $C_{1-12}$ alkyl, $C_{2-12}$ alkenyl, $C_{2-12}$ alkynyl, $C_{3-10}$ cycloalkyl, heterocyclyl, aryl, or heteroaryl; wherein the $C_{1-12}$ alkyl, $C_{2-12}$ alkenyl and $C_{2-12}$ alkynyl are optionally substituted with one or more halo; the $C_{3-10}$ cycloalkyl, heterocyclyl, aryl, heteroaryl are independently optionally substituted with one or more cyano, halo, nitro, oxo, —$OR^{14}$, —$SR^{14}$, —$SF_5$, —$NR^{14}R^{15}$, —$S(=O)_{1-2}R^{16}$, —$S(=O)_{1-2}NR^{14}R^{15}$, —$NR^{14}S(=O)_{1-2}R^{16}$, or $R^{16}$;

$R^{11}$, $R^{12}$, $R^{14}$, and $R^{15}$ are independently H or $C_{1-12}$ alkyl optionally substituted with one or more halo, or two of $R^{11}$ and $R^{12}$ or two of $R^{14}$ and $R^{15}$ together with the atoms to which they are attached form a heterocyclyl optionally substituted with one or more halo or $C_{1-12}$ alkyl optionally substituted with one or more halo;

$R^{13}$ and $R^{16}$ are independently $C_{1-12}$ alkyl optionally substituted with one or more halo; and m is 0, 1, 2, 3, 4, or 5.

In certain embodiments, provided is a compound of formula If-1:

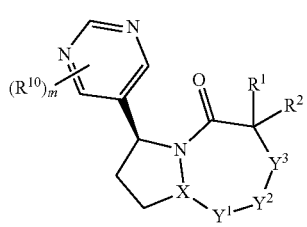

If-1 or a pharmaceutically acceptable salt, deuterated analog, stereoisomer, mixture of stereoisomers, tautomer, or prodrug thereof, where $R^{10}$, m, X, $Y^1$, $Y^2$, $Y^3$, $R^1$ and $R^2$ are as defined herein.

In certain embodiments, provided is a compound of formula Ig:

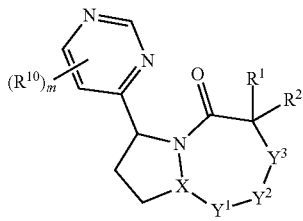

Ig or a pharmaceutically acceptable salt, deuterated analog, stereoisomer, mixture of stereoisomers, tautomer, or prodrug thereof, wherein:

X is N or $CR^4$, wherein $R^4$ is H or optionally substituted alkyl;

$Y^1$, $Y^2$, and $Y^3$ are independently $CR^5R^6$, S, SO, $SO_2$, O, or $NR^7$;

$R^1$ is cyano, optionally substituted alkyl, optionally substituted alkenyl, optionally substituted alkynyl, optionally substituted alkoxy, $-SR^8$, $-SOR^8$, $-SO_2R^8$, optionally substituted cycloalkyl, optionally substituted heterocyclyl, optionally substituted aryl, or optionally substituted heteroaryl;

$R^2$ is cyano, hydrogen, halo, optionally substituted alkyl, optionally substituted alkenyl, optionally substituted alkynyl, optionally substituted cycloalkyl, optionally substituted heterocyclyl, optionally substituted aryl, or optionally substituted heteroaryl; or $R^1$ and $R^2$ together form an optionally substituted cycloalkyl or optionally substituted heterocyclyl;

$R^3$ is independently halo, cyano, or optionally substituted alkyl;

$R^5$ and $R^6$ are independently cyano, halo, hydrogen, hydroxyl, optionally substituted alkyl, optionally substituted alkenyl, optionally substituted alkynyl, optionally substituted alkoxy, $-SH$, $-SR^8$, $-SOR^8$, $-SO_2R^8$, optionally substituted cycloalkyl, optionally substituted heterocyclyl, optionally substituted aryl, or optionally substituted heteroaryl; or $R^5$ and $R^6$ together with the carbon atom to which they are both attached form an optionally substituted cycloalkyl, optionally substituted heterocyclyl, or oxo; or $R^5$ and $R^6$ attached to adjacent carbon atoms together form an optionally substituted cycloalkyl or optionally substituted heterocyclyl;

$R^7$ is hydrogen or optionally substituted alkyl;

$R^8$ is optionally substituted alkyl;

$R^{10}$ is independently cyano, halo, nitro, $-OR^{11}$, $-SR^{11}$, $-SF_5$, $-NR^{11}R^{12}$, $-C(=O)R^{13}$, $-C(=O)OR^{11}$, $-OC(=O)OR^{11}$, $-OC(=O)R^{13}$, $-C(=O)NR^{11}R^{12}$, $-OC(=O)NR^{11}R^{12}$, $-NR^{11}C(=O)NR^{11}R^{12}$, $-S(=O)_{1-2}R^{13}$, $-S(=O)_{1-2}NR^{11}R^{12}$, $-NR^{11}S(=O)_{1-2}R^{13}$, $-NR^{11}S(=O)_{1-2}NR^{11}R^{12}$, $-NR^{11}C(=O)R^{13}$, $-NR^{11}C(=O)OR^{12}$, $-C=NOR^{11}$, $C_{1-2}$ alkyl, $C_{2-12}$ alkenyl, $C_{2-12}$ alkynyl, $C_{3-10}$ cycloalkyl, heterocyclyl, aryl, or heteroaryl; wherein the $C_{1-12}$ alkyl, $C_{2-12}$ alkenyl and $C_{2-12}$ alkynyl are optionally substituted with one or more halo; the $C_{3-10}$ cycloalkyl, heterocyclyl, aryl, heteroaryl are independently optionally substituted with one or more cyano, halo, nitro, oxo, $-OR^{14}$, $-SR^{14}$, $-SF_5$, $-NR^{14}R^{15}$, $-S(=O)_{1-2}R^{16}$, $-S(=O)_{1-2}NR^{14}R^{15}$, $-NR^{14}S(=O)_{1-2}R^{16}$, or $R^{16}$;

$R^{11}$, $R^{12}$, $R^{14}$, and $R^{15}$ are independently H or $C_{1-12}$ alkyl optionally substituted with one or more halo, or two of $R^{11}$ and $R^{12}$ or two of $R^{14}$ and $R^{15}$ together with the atoms to which they are attached form a heterocyclyl optionally substituted with one or more halo or $C_{1-12}$ alkyl optionally substituted with one or more halo;

$R^{13}$ and $R^{16}$ are independently $C_{1-12}$ alkyl optionally substituted with one or more halo; and m is 0, 1, 2, 3, 4, or 5.

In certain embodiments, provided is a compound of formula Ig-1:

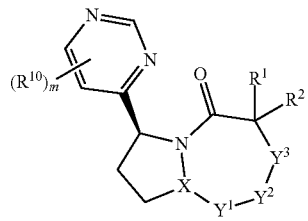

Ig-1 or a pharmaceutically acceptable salt, deuterated analog, stereoisomer, mixture of stereoisomers, tautomer, or prodrug thereof, where $R^{10}$, m, X, $Y^1$, $Y^2$, $Y^3$, $R^1$ and $R^2$ are as defined herein.

In certain embodiments, provided is a compound of formula Ih:

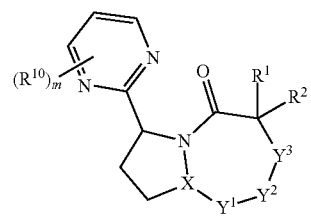

Ih or a pharmaceutically acceptable salt, deuterated analog, stereoisomer, mixture of stereoisomers, tautomer, or prodrug thereof, wherein:

X is N or $CR^4$, wherein $R^4$ is H or optionally substituted alkyl;

$Y^1$, $Y^2$, and $Y^3$ are independently $CR^5R^6$, S, SO, $SO^2$, O, or $NR^7$;

$R^1$ is cyano, optionally substituted alkyl, optionally substituted alkenyl, optionally substituted alkynyl, optionally substituted alkoxy, $-SR^8$, $-SOR^8$, $-SO_2R^8$, optionally substituted cycloalkyl, optionally substituted heterocyclyl, optionally substituted aryl, or optionally substituted heteroaryl;

$R^2$ is cyano, hydrogen, halo, optionally substituted alkyl, optionally substituted alkenyl, optionally substituted alkynyl, optionally substituted cycloalkyl, optionally substituted heterocyclyl, optionally substituted aryl, or optionally substituted heteroaryl; or $R^1$ and $R^2$ together form an optionally substituted cycloalkyl or optionally substituted heterocyclyl;

$R^3$ is independently halo, cyano, or optionally substituted alkyl;

$R^5$ and $R^6$ are independently cyano, halo, hydrogen, hydroxyl, optionally substituted alkyl, optionally substituted alkenyl, optionally substituted alkynyl, optionally substituted alkoxy, —SH, —SR$^8$, —SOR$^8$, —SO$_2$R$^8$, optionally substituted cycloalkyl, optionally substituted heterocyclyl, optionally substituted aryl, or optionally substituted heteroaryl; or R$^5$ and R$^6$ together with the carbon atom to which they are both attached form an optionally substituted cycloalkyl, optionally substituted heterocyclyl, or oxo; or R$^5$ and R$^6$ attached to adjacent carbon atoms together form an optionally substituted cycloalkyl or optionally substituted heterocyclyl;

R$^7$ is hydrogen or optionally substituted alkyl;

R$^8$ is optionally substituted alkyl;

R$^{10}$ is independently cyano, halo, nitro, —OR$^{11}$, —SR$^{11}$, —SF$_5$, —NR$^{11}$R$^{12}$, —C(=O)R$^{13}$, —C(=O)OR$^{11}$, —OC(=O)OR$^{11}$, —OC(=O)R$^{13}$, —C(=O)NR$^{11}$R$^{12}$, —OC(=O)NR$^{11}$R$^{12}$, —NR$^{11}$C(=O)NR$^{11}$R$^{12}$, —S(=O)$_{1-2}$R$^{13}$, —S(=O)$_{1-2}$NR$^{11}$R$^{12}$, —NR$^{11}$S(=O)$_{1-2}$R$^{13}$, —NR$^{11}$S(=O)$_{1-2}$NR$^{11}$R$^{12}$, —NR$^{11}$C(=O)R$^{13}$, —NR$^{11}$C(=O)OR$^{12}$, —C=NOR$^{11}$, C$_{1-2}$ alkyl, C$_{2-12}$ alkenyl, C$_{2-12}$ alkynyl, C$_{3-10}$ cycloalkyl, heterocyclyl, aryl, or heteroaryl: wherein the C$_{1-12}$ alkyl, C$_{2-12}$ alkenyl and C$_{2-12}$ alkynyl are optionally substituted with one or more halo; the C$_{3-10}$ cycloalkyl, heterocyclyl, aryl, heteroaryl are independently optionally substituted with one or more cyano, halo, nitro, oxo, —OR$^{14}$, —SR$^{14}$, —SF$_5$, —NR$^{14}$R$^{15}$, —S(=O)$_{1-2}$R$^{16}$, —S(=O)$_{1-2}$NR$^{14}$R$^{15}$, —NR$^{14}$S(=O)$_{1-2}$R$^{16}$, or R$^{16}$;

R$^{11}$, R$^{12}$, R$^{14}$, and R$^{15}$ are independently H or C$_{1-12}$ alkyl optionally substituted with one or more halo, or two of R$^{11}$ and R$^{12}$ or two of R$^{14}$ and R$^{15}$ together with the atoms to which they are attached form a heterocyclyl optionally substituted with one or more halo or C$_{1-12}$ alkyl optionally substituted with one or more halo;

R$^{13}$ and R$^{16}$ are independently C$_{1-12}$ alkyl optionally substituted with one or more halo; and m is 0, 1, 2, 3, 4, or 5.

In certain embodiments, provided is a compound of formula Ih-1:

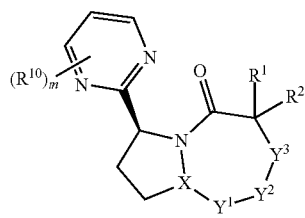

Ih-1 or a pharmaceutically acceptable salt, deuterated analog, stereoisomer, mixture of stereoisomers, tautomer, or prodrug thereof, where R$^{10}$, m, X, Y$^1$, Y$^2$, Y$^3$, R$^1$ and R$^2$ are as defined herein.

In certain embodiments, X is N.

In certain embodiments, X is CR$^4$. In certain embodiments, X is CH.

In certain embodiments, Y$^2$ is O and Y$^1$ and Y$^3$ are CR$^5$R$^6$.

In certain embodiments, Y$^3$ is O and Y$^1$ and Y$^2$ are CR$^5$R$^6$.

In certain embodiments, Y$^1$, Y$^2$, and Y$^3$ are CR$^5$R$^6$.

In certain embodiments, Y$^3$ are CF$_2$.

In certain embodiments, Y$^1$, Y$^2$, and Y$^3$ are CH$_2$.

In certain embodiments, when X is CR$^4$, then at least one of Y$^1$, Y$^2$, and Y$^3$ is other than CH$_2$.

In certain embodiments, X is N; and Y$^1$, Y$^2$, and Y$^3$ are CH$_2$.

In certain embodiments, X is CR$^4$; Y$^2$ is O; and Y$^1$ and Y$^3$ are CR$^5$R$^6$. In certain embodiments, X is CR$^4$; Y$^1$ and Y$^2$ are CR$^5$R$^6$; and Y$^3$ is O. In certain embodiments, X is CR$^4$; Y$^1$ is O; and Y$^2$ and Y$^3$ are CR$^5$R$^6$.

In certain embodiments, X is CH; Y$^2$ is O; and Y$^1$ and Y$^3$ are CH$_2$. In certain embodiments, X is CH; Y$^1$ and Y$^2$ are CH$_2$; and Y$^3$ is O. In certain embodiments, X is CH; Y$^1$ is O; and Y$^2$ and Y$^3$ are CH$_2$.

In certain embodiments, n is 1. In certain embodiments, n is 0.

In certain embodiments, R$^1$ and R$^2$ are optionally substituted alkyl.

In certain embodiments, R$^1$ and R$^2$ together form a cyclopropyl ring.

In certain embodiments, R$^1$ is haloalkyl, cyanomethyl, methyl, or ethyl.

In certain embodiments, R$^1$ is difluoromethyl, cyanomethyl, methyl, or ethyl.

In certain embodiments, R$^2$ is methyl.

In certain embodiments, R$^{10}$ is independently cyano, halo, C$_{1-12}$ alkyl, C$_{2-12}$ alkenyl, or C$_{2-12}$ alkynyl; wherein the C$_{1-12}$ alkyl, C$_{2-12}$ alkenyl and C$_{2-12}$ alkynyl are optionally substituted with one or more halo. In certain embodiments, R$^{10}$ is independently cyano, halo, or C$_{1-12}$ alkyl; wherein the C$_{1-12}$ alkyl is optionally substituted with one or more halo. In certain embodiments, R$^{10}$ is independently cyano, halo, methyl, ethyl or difluoromethyl.

In certain embodiments, m is 2. In certain embodiments, m is 1. In certain embodiments, m is 0.

In certain embodiments, the compound is a compound selected from Table 1. Also included within the disclosure are pharmaceutically acceptable salts, deuterated analogs, stereoisomers, mixtures of stereoisomers, tautomers, and/or prodrugs thereof.

TABLE 1

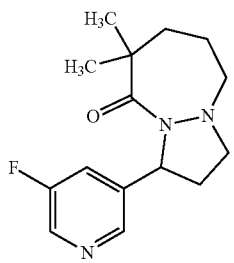 [SMILES: CC1(C)CCCN2CCC(c3cncc(F)c3)N2C1=O]

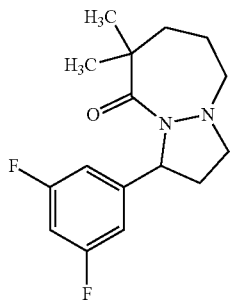 [SMILES: CC1(C)CCCN2CCC(c3cc(F)cc(C#N)c3)N2C1=O]

TABLE 1-continued
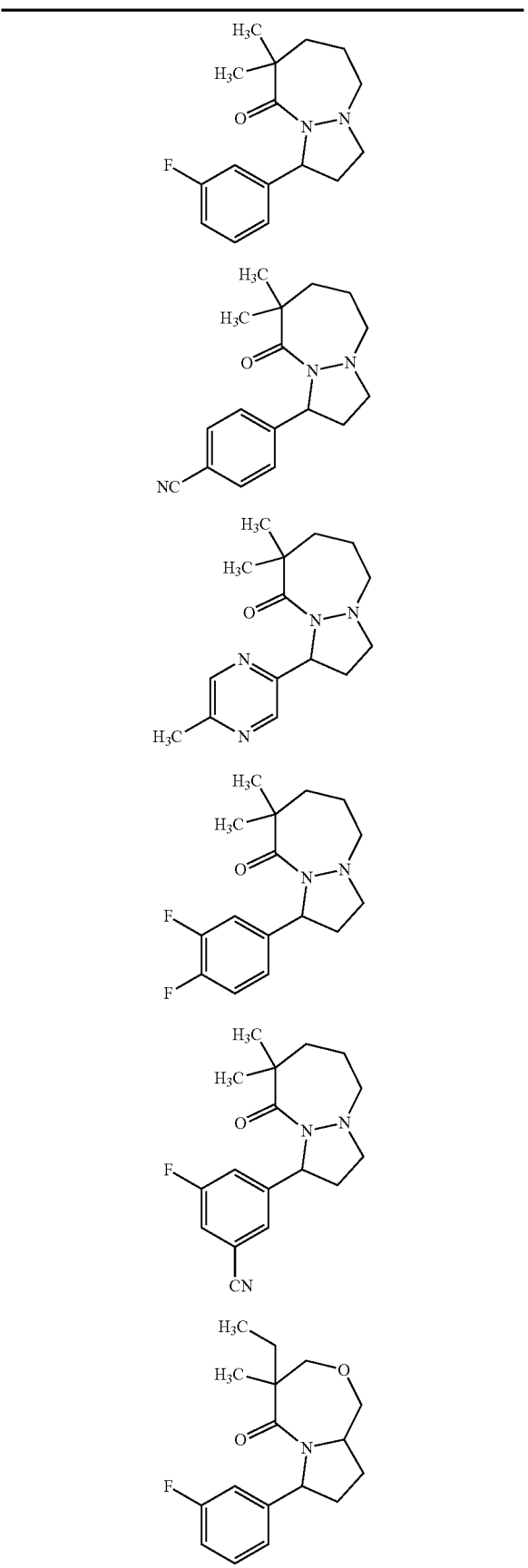
TABLE 1-continued
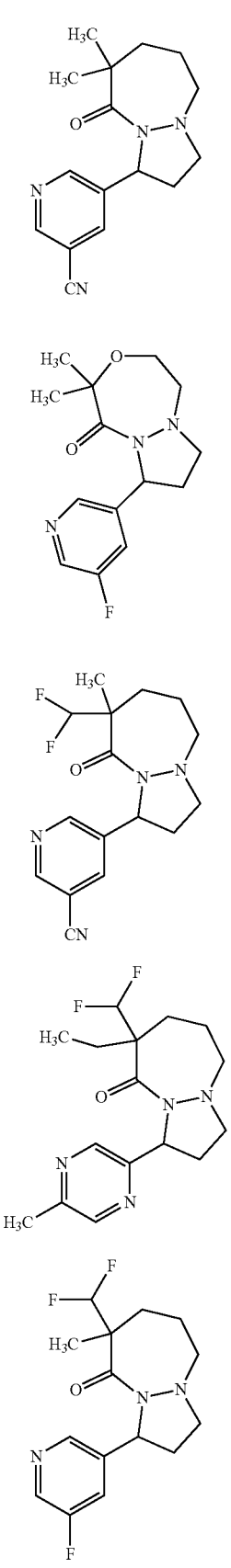

TABLE 1-continued
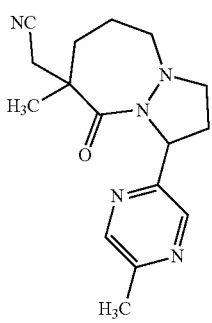 [SMILES: Cc1cnc(C2CCN3CCCC(C)(CC#N)C(=O)N23)cn1]
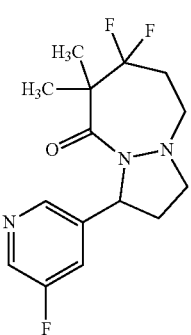 [SMILES: CC1(C)C(=O)N2C(c3cncc(F)c3)CCN2CCC1(F)F]
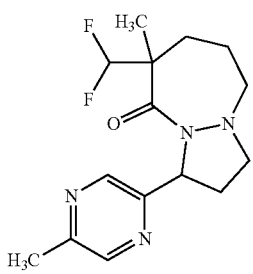 [SMILES: Cc1cnc(C2CCN3CCCC(C)(C(F)F)C(=O)N23)cn1]
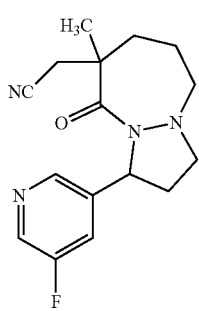 [SMILES: CC1(CC#N)CCCN2CCC(c3cncc(F)c3)N2C1=O]
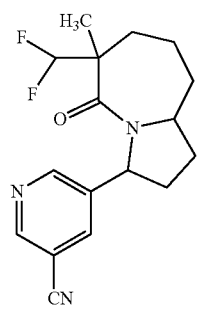 [SMILES: CC1(C(F)F)CCCC2CCC(c3cncc(C#N)c3)N2C1=O]
TABLE 1-continued
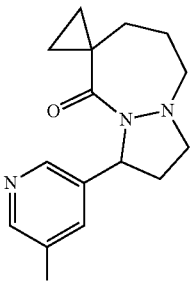
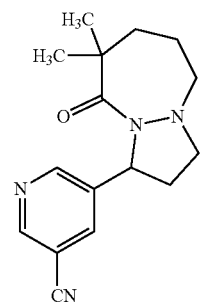 [SMILES: CC1(C)CCCN2CCC(c3cncc(C#N)c3)N2C1=O]
In certain embodiments, the compound is a compound selected from Table 2. Also included within the disclosure are pharmaceutically acceptable salts, deuterated analogs, tautomers, and/or prodrugs thereof.
TABLE 2
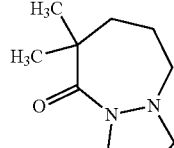
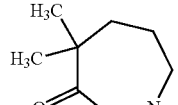
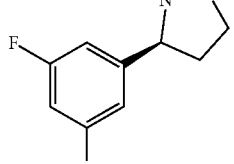

TABLE 2-continued

TABLE 2-continued
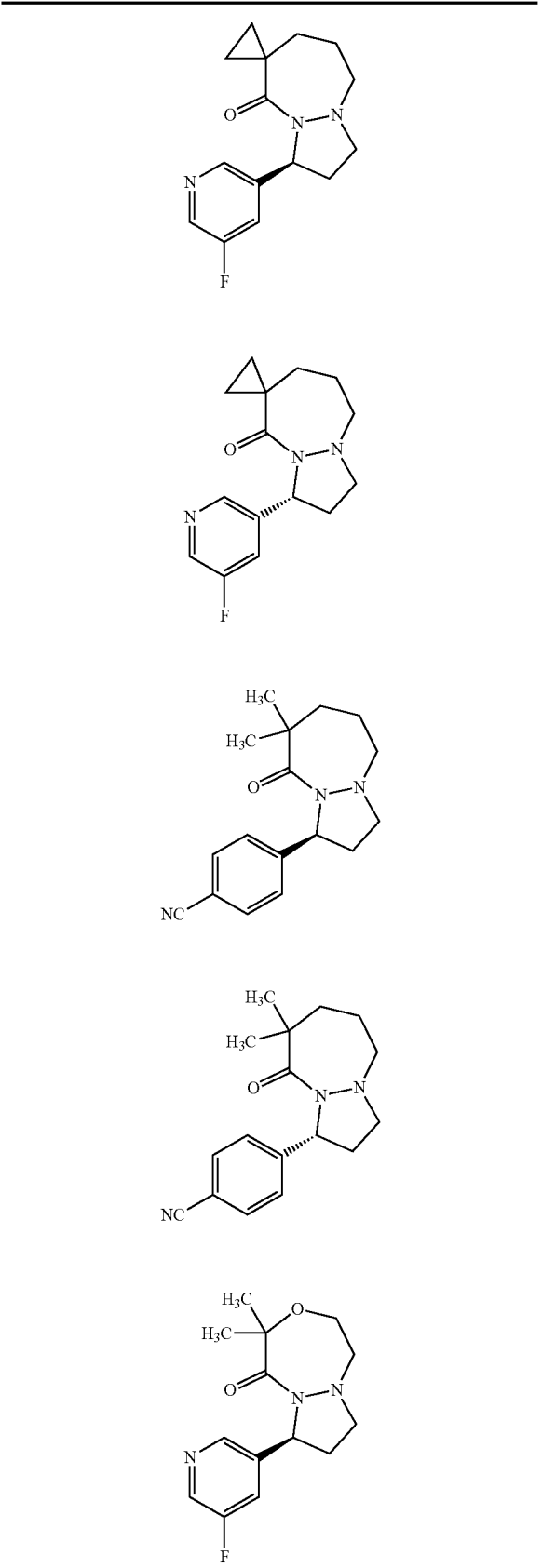
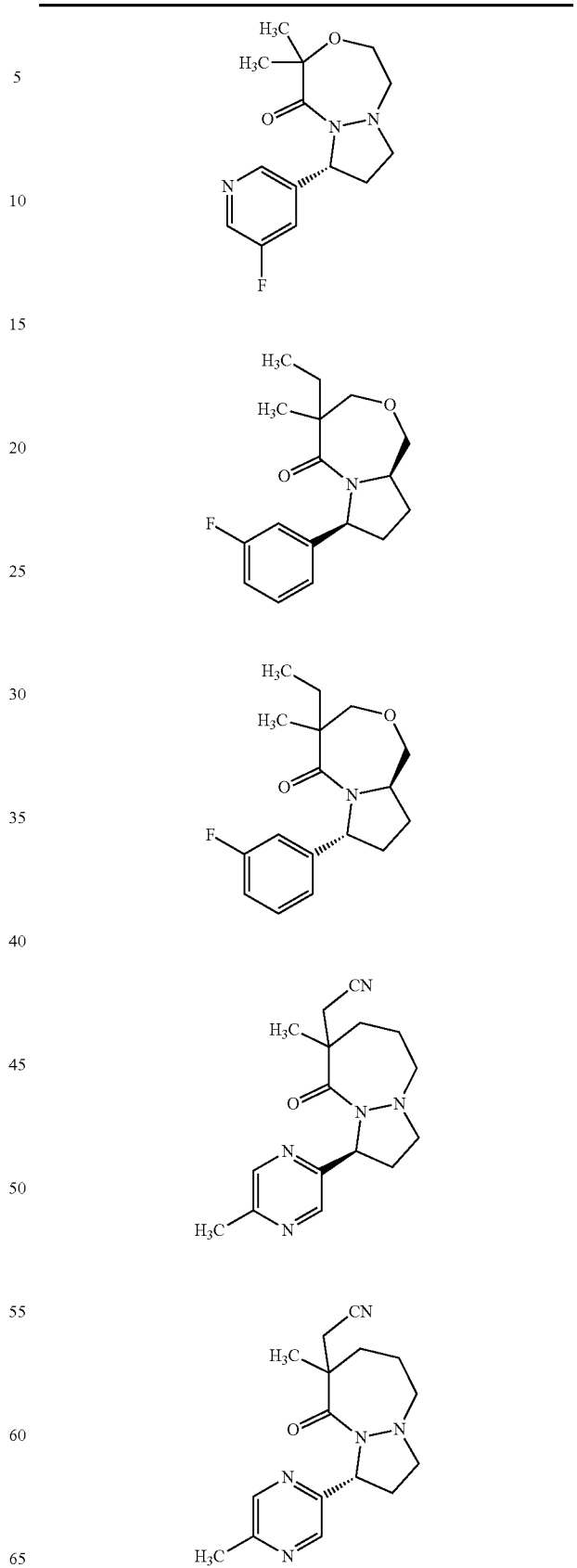

TABLE 2-continued
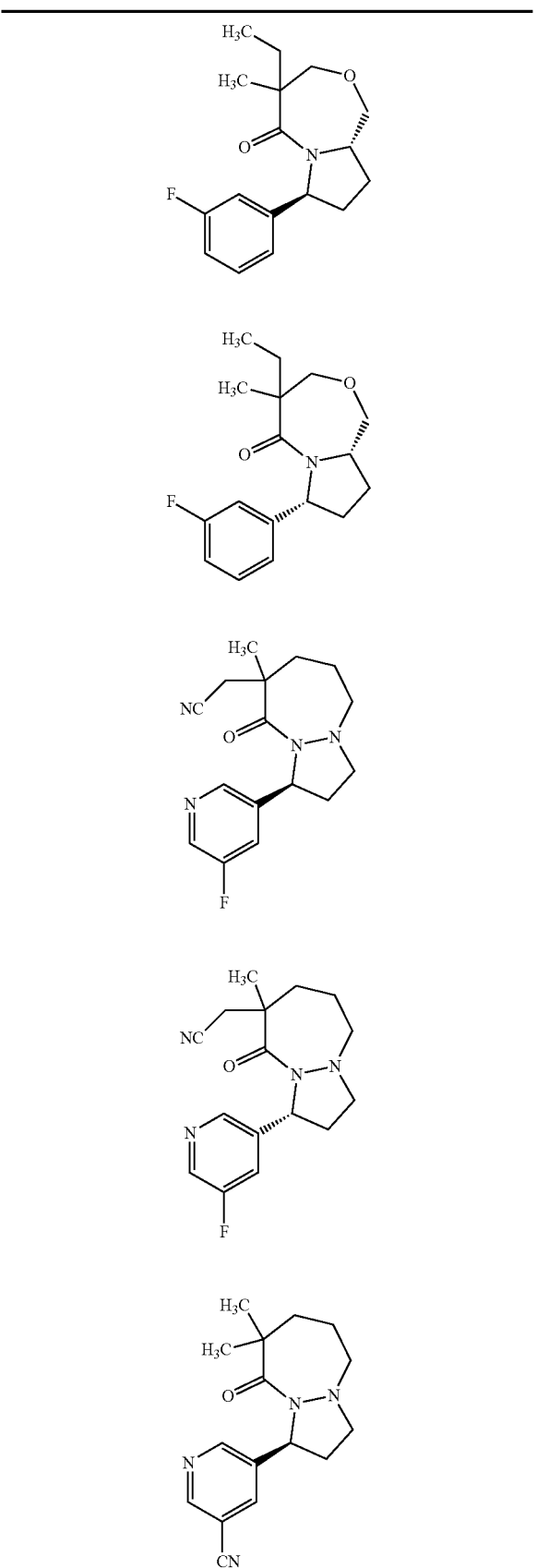
TABLE 2-continued
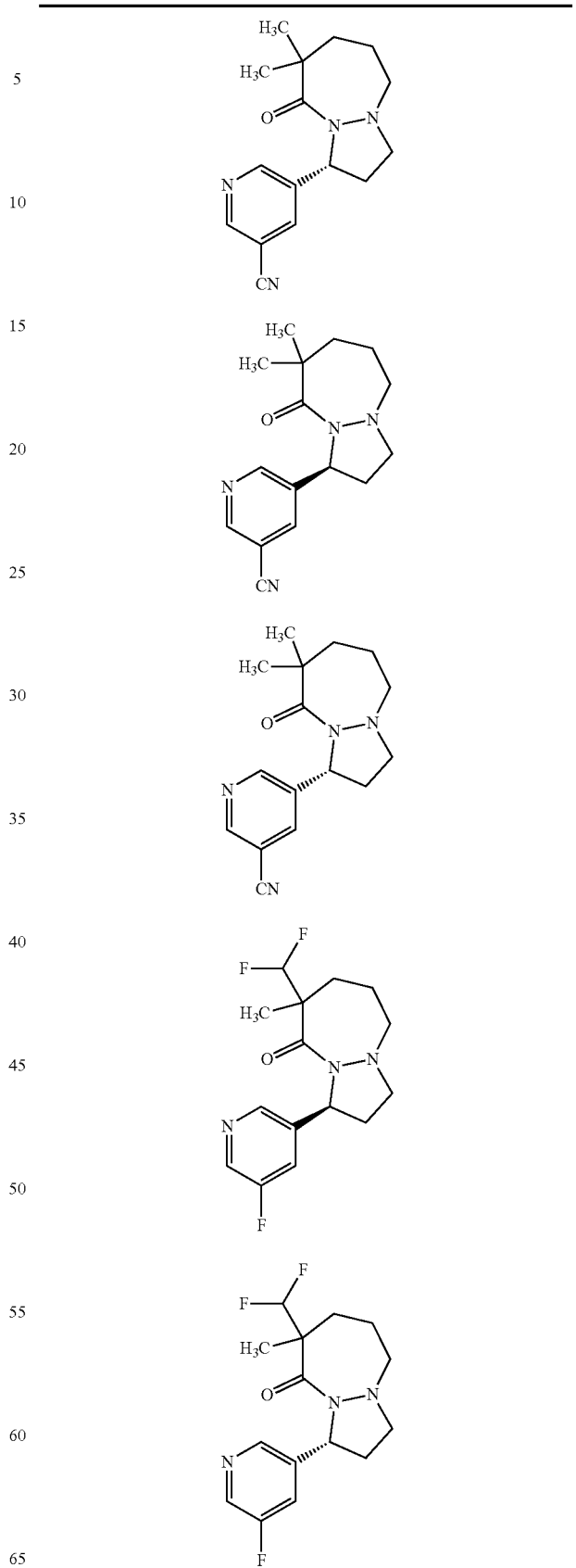

TABLE 2-continued
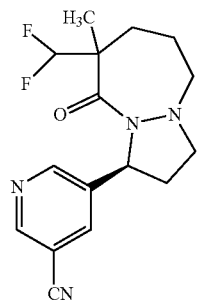 [SMILES: CC1(C(F)F)CCCN2CC[C@@H](c3cncc(C#N)c3)N2C1=O]
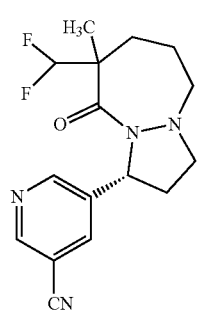 [SMILES: CC1(C(F)F)CCCN2CC[C@H](c3cncc(C#N)c3)N2C1=O]
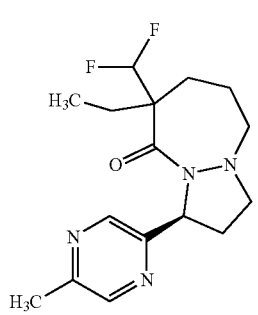 [SMILES: CCC1(C(F)F)CCCN2CC[C@@H](c3cnc(C)cn3)N2C1=O]
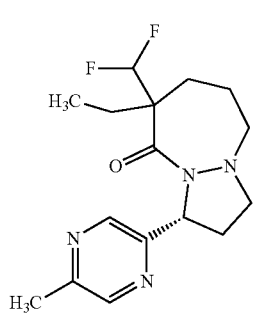 [SMILES: CCC1(C(F)F)CCCN2CC[C@H](c3cnc(C)cn3)N2C1=O]
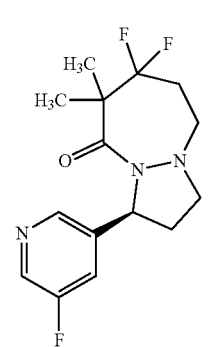 [SMILES: CC1(C)C(=O)N2[C@H](c3cncc(F)c3)CCN2CCC1(F)F]
TABLE 2-continued
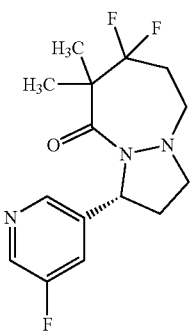 [SMILES: CC1(C)C(=O)N2[C@@H](c3cncc(F)c3)CCN2CCC1(F)F]
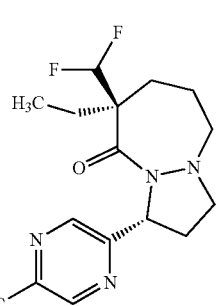
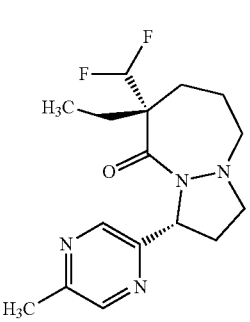 [SMILES: CC[C@@]1(C(F)F)CCCN2CC[C@H](c3cnc(C)cn3)N2C1=O]
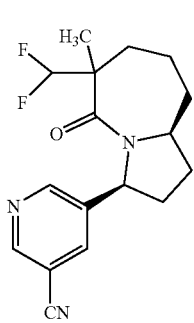
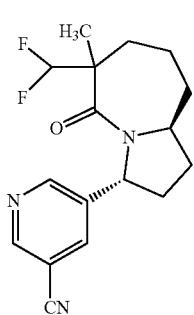

TABLE 2-continued

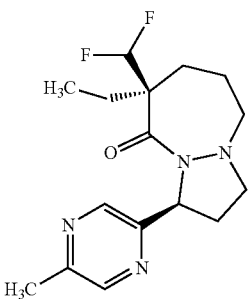 [SMILES: CC[C@]1(C(F)F)CCCN2CC[C@@H](c3cnc(C)cn3)N2C1=O]

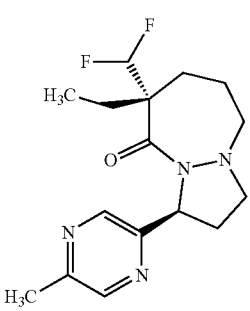 [SMILES: CC[C@@]1(C(F)F)CCCN2CC[C@@H](c3cnc(C)cn3)N2C1=O]

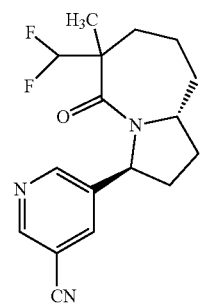

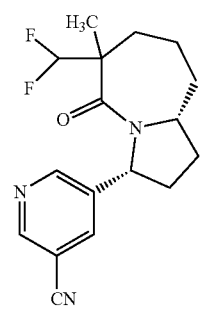

In certain embodiments, the compound of any Formula provided herein is provided in the form of a pharmaceutically acceptable salt. Exemplary salts for this purpose are described herein.

In certain embodiments, the disclosure provides a prodrug which converts to a compound of any Formula provided herein in vivo. Exemplary prodrugs for this purpose are known in the art and described herein.

Enantiomerically enriched compositions of the compounds disclosed herein are also provided. In certain embodiments, the enantiomeric ratio of the composition is greater than 50:50. In certain embodiments, the enantiomeric ratio is calculated only with respect to a single stereocenter (e.g., the optionally substituted Cy moiety) without regard to other stereocenters which may be present on the molecule. In certain embodiments, the composition comprises a single enantiomer of the compound and is substantially free (i.e., having less than or about 40%, 30%, 25%, 20%, 15%, 10%, 5%, 1%, 0.05%, or 0.01%) of the other enantiomer (or diastereomers).

3. General Synthesis

In certain embodiments, provided is a method of preparing a compound of Formula I, where X is N, comprising cyclizing a compound of Formula 1-G:

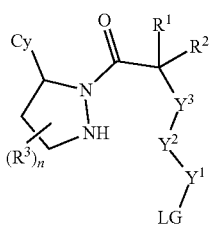

1-G under conditions to provide the compound of Formula I, wherein Cy, n, $Y^1$, $Y^2$, $Y^3$, $R^1$, $R^2$ and $R^3$ are as defined herein and LG is a leaving group.

In certain embodiments, provided is a method of preparing a compound of Formula I, comprising cyclizing a compound of Formula 2-C:

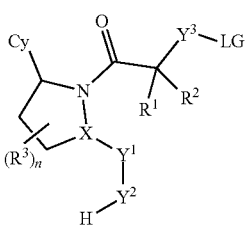

2-C under conditions to provide the compound of Formula I, wherein X, Cy, n, $Y^1$, $Y^2$, $Y^3$, $R^1$, $R^2$ and $R^3$ are as defined herein and LG is a leaving group.

The following General Reaction Schemes 1 and 2 further illustrate methods of making compounds of Formula I. Other methods for preparing compounds of Formula I and related intermediates are provided in the Examples and/or known in the art. It is understood that one skilled in the art may be able to make these compounds by similar methods or by combining other methods known to one skilled in the art. In general, starting components and reagents may be obtained from sources such as Sigma Aldrich, Lancaster Synthesis, Inc., Maybridge, Matrix Scientific, TCI and Fluorochem USA, etc. or synthesized according to sources known to those skilled in the art (see, for example, Advanced Organic Chemistry: Reactions, Mechanisms and Structure, 5th edition (Wiley, December 2000)) or prepared as described in this disclosure.

Scheme 1

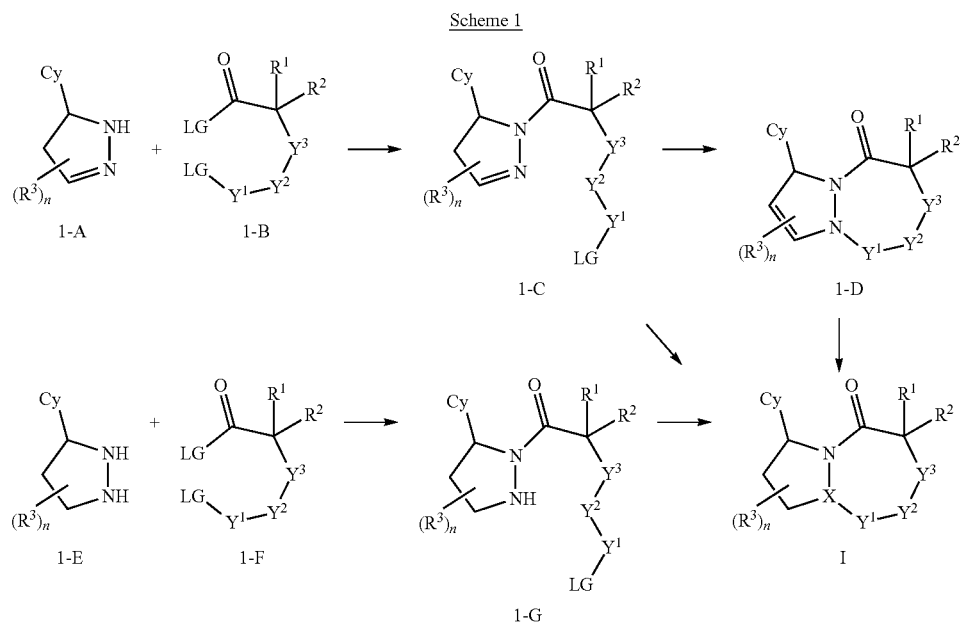

Referring to Scheme 1, compounds of Formula I, wherein Cy, n, $Y^1$, $Y^2$, $Y^3$, $R^1$, $R^2$ and $R^3$ are as defined herein, X is N, and LG is a leaving group (e.g., halo), may be prepared by reducing compound 1-D with a suitable hydride reagent (e.g., sodium cyanoborohydride, lithium triethylborohydride, etc.). Compound 1-D can be prepared by cyclizing compound 1-C under suitable reaction conditions, such as with sodium iodide, optionally in a microwave reactor. Compound 1-C can be prepared by contacting compound 1-A with compound 1-B under standard amide bond forming reaction conditions in a suitable solvent. Alternatively, contacting compound 1-E with compound 1-F under standard amide bond forming reaction conditions in a suitable solvent provides compound 1-G, which under suitable cyclization reaction conditions, may be cyclized to provide compounds of Formula I. Alternatively, compound 1-C can be hydrogenated, followed by cyclization to provide compounds of Formula I.

Appropriate compounds 1-A, 1-B, 1-E and 1-F can be prepared according to the more specific methods described in the Examples which follow or by methods known to one of skill in the art.

Scheme 2

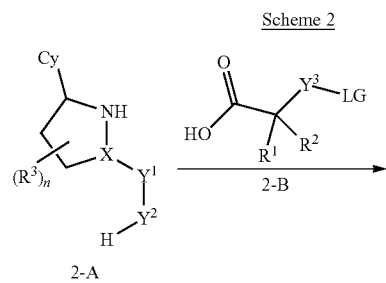

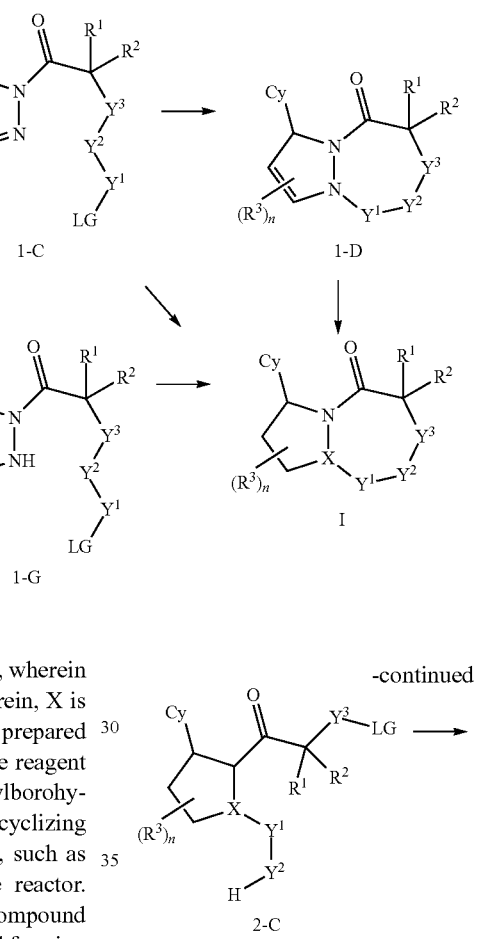

Referring to Scheme 2, compounds of Formula I, wherein Cy, n, $Y^1$, $Y^2$, $Y^3$, $R^1$, $R^2$ and $R^3$ are as defined herein, X is N, and LG is a leaving group (e.g., halo), may be prepared cyclizing compound 2-C under suitable reaction conditions, such as with sodium iodide, optionally in a microwave reactor. Compound 2-C can be prepared by contacting compound 2-A with compound 2-B under standard amide bond forming reaction conditions in a suitable solvent.

Appropriate compounds D or E can be prepared according to the more specific methods described in the Examples which follow or by methods known to one of skill in the art.

When enantiomerically pure or enriched compounds are desired, chiral chromatography and/or enantiomerically pure or enriched starting materials (e.g., compound A or D) may be used as described in the Examples. It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl and the like. Suitable protecting groups for amino, amidino and guanidino include t-butoxycarbonyl, benzyloxycarbonyl and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this disclosure may not possess pharmacological activity as such, they may be administered to a mammal and thereafter metabolized in the body to form compounds of the disclosure which are pharmacologically active. Such derivatives may therefore be described as "prodrugs." All prodrugs of compounds of this disclosure are included within the scope of the disclosure. Further, the above general scheme can be applied to any other Formula or compound as described herein.

Furthermore, all compounds of Formula I or any other Formula or compound as described herein which exist in free base or acid form can be converted to their pharmaceutically acceptable salts by treatment with the appropriate inorganic or organic base or acid by methods known to one skilled in the art. Salts of the compounds of the disclosure can be converted to their free base or acid form by standard techniques.

4. Methods of Treatment

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition and/or diminishing the extent of the disease or condition); b) slowing or arresting the development of one or more clinical symptoms associated with the disease or condition (e.g., stabilizing the disease or condition, preventing or delaying the worsening or progression of the disease or condition and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life and/or prolonging survival).

"Prevention" or "preventing" means any treatment of a disease or condition that causes the clinical symptoms of the disease or condition not to develop. Compounds may, in certain embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In certain embodiments, the subject is a mammal. In certain embodiments, the subject is a human.

The term "therapeutically effective amount" or "effective amount" of a compound described herein or a pharmaceutically acceptable salt, prodrug, stereoisomer or a mixture of stereoisomers thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition of as described herein. The therapeutically effective amount may vary depending on the subject and disease or condition being treated, the weight and age of the subject, the severity of the disease or condition and the manner of administering, which can readily be determined by one of ordinary skill in the art.

The term "trauma" as used herein refers to any physical damage to the body caused by violence, accident, fracture etc. The term "ischemia" refers to a cardiovascular disorder characterized by a low oxygen state usually due to the obstruction of the arterial blood supply or inadequate blood flow leading to hypoxia in the tissue. The term "stroke" refers to cardiovascular disorders caused by a blood clot or bleeding in the brain, most commonly caused by an interruption in the flow of blood in the brain as from clot blocking a blood vessel and in certain embodiments of the disclosure the term stroke refers to ischemic stroke or hemorrhagic stroke. The term "myocardial infarction" refers to a cardiovascular disorder characterized by localized necrosis resulting from obstruction of the blood supply.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

Experiments with knockout animal models and Necrostatin 1, a receptor interacting protein kinase 1 inhibitor, have demonstrated the effectiveness of receptor interacting protein kinase 1 inhibition in protecting tissues from inflammatory bowel diseases (e.g., ulcerative colitis and Crohn's disease), psoriasis, retinal-detachment-induced photoreceptor necrosis, retinitis pigmentosa, cerulein-induced acute pancreatits and sepsis/systemic inflammatory response syndrome (SIRS) and alleviating ischemic brain injury, retinal ischemia/reperfusion injury, Huntington's disease, renal ischemia reperfusion injury, cisplatin induced kidney injury, traumatic brain injury, hematological and solid organ malignancies, bacterial infections and viral infections (e.g., tuberculosis and influenza) and lysosomal storage diseases.

The receptor interacting protein kinase 1 inhibitors of the present disclosure are therefore useful for treating diseases and conditions mediated by receptor interacting protein kinase 1, including but not limited to inflammatory diseases or disorders, necrotic cell diseases, neurodegenerative diseases, central nerve system (CNS) diseases, ocular diseases, infections and malignancies. In certain embodiments, the receptor interacting protein kinase 1 inhibitors described herein can inhibit inflammation, protect tissue or cell from damage or undesired cell death (e.g., necrosis or apoptosis), ameliorate symptoms and improve immune response in a patient suffering from any of the prescribed diseases or conditions. Moreover, the compounds may be suitable for treatment of immune-mediated disease, such as but not limited to, allergic diseases, autoimmune diseases and prevention of transplant rejection.

Necrotic Cell Diseases

The compounds described herein may be used for the treatment of diseases/disorders caused or otherwise associated with cellular necrosis. In particular, the disclosure provides methods for preventing or treating a disorder associated with cellular necrosis in a mammal, comprising the step of administering to said mammal a therapeutically effective amount of a compound or composition described herein. The term "necrotic cell disease" refers to diseases associated with or caused by cellular necrosis, for example trauma, ischemia, stroke, cardiac infarction, infection, Gaucher's disease, Krabbe disease, sepsis, Parkinson's disease, Alzheimer's disease, amyotrophic lateral sclerosis, Huntington's disease, HIV-associated dementia, retinal degenerative disease, glaucoma, age-related macular degeneration, rheumatoid arthritis, psoriasis, psoriatic arthritis or inflammatory bowel disease.

The necrotic cell diseases can be acute diseases such as trauma, ischemia, stroke, cardiac infarction, anthrax lethal toxin induced septic shock, sepsis, cell death induced by LPS and HIV induced T-cell death leading to immunodeficiency. In certain embodiments the disorder is an ischemic disease of organs including but not limited to brain, heart, kidney and liver.

The necrotic cell diseases also include chronic neurodegenerative diseases, such as Parkinson's disease, Huntington's disease, amyotrophic lateral sclerosis, Alzheimer's disease, infectious encephalopathy, dementia such as HIV associated dementia.

In some different embodiments, the disorder is an ocular disorder such as retinal degenerative disease, glaucoma or age-related macular degeneration. In some different embodiments, the disorder is a central nervous system (CNS) disorder.

Inflammatory Diseases or Disorders

The receptor interacting protein kinase 1 inhibitors described herein may be used to treat inflammatory diseases and disorders. Inflammatory diseases and disorders typically exhibit high levels of inflammation in the connective tissues or degeneration of these tissues.

Non-limiting examples of inflammatory diseases and disorders include Alzheimer's disease, ankylosing spondylitis, arthritis including osteoarthritis, rheumatoid arthritis (RA), psoriasis, asthma, atherosclerosis, Crohn's disease, colitis, dermatitis, diverticulitis, fibromyalgia, hepatitis, irritable bowel syndrome (IBS), inflammatory bowel disease (IBD), systemic lupus erythematous (SLE), nephritis, Parkinson's disease and ulcerative colitis. In certain embodiments, the compounds and compositions of the present disclosure are useful for treating an autoimmune disorder, such as rheumatoid arthritis, psoriasis, psoriatic arthritis, encephalitis, allograft rejection, autoimmune thyroid diseases (such as Graves' disease and Hashimoto's thyroiditis), autoimmune uveoretinitis, giant cell arteritis, inflammatory bowel diseases (including Crohn's disease, ulcerative colitis, regional enteritis, granulomatous enteritis, distal ileitis, regional ileitis, and terminal ileitis), insulin-dependent diabetes mellitus, multiple sclerosis, pernicious anemia, sarcoidosis, scleroderma, and systemic lupus erythematosus. In an embodiment, the receptor interacting protein kinase 1 inhibitors described herein are useful for treating autoimmune encephalitis.

In certain embodiments, the compounds and compositions are useful for treating rheumatoid arthritis (RA). In certain embodiments, the compounds and compositions are useful for treating ulcerative colitis. In certain embodiments, the compounds and compositions are useful for treating psoriasis.

In certain embodiments, the disorder is an inflammatory disease of the intestines such as Crohn's disease or ulcerative colitis (both generally known together as inflammatory bowel disease). In certain embodiments, the mammal is a primate, canine or feline subject. In certain embodiments, the mammal is a human subject. While not wishing to be bound by theory, it is believed that inhibition of receptor interacting protein kinase 1 by the presently disclosed compounds is responsible, at least in part, for their anti-inflammatory activity. Accordingly, embodiments of the disclosure also include methods for inhibiting receptor interacting protein kinase 1, either in vitro or in a subject in need thereof, the method comprises contacting a receptor interacting protein kinase 1 with a compound disclosed herein. In some of these embodiments, inhibiting receptor interacting protein kinase 1 is effective to block (partially or fully) the release of inflammatory mediators such as TNF and/or IL6.

Ocular Conditions

The receptor interacting protein kinase 1 inhibitors described herein can also be used to treat ocular conditions, for example to reduce or prevent the loss of photoreceptor and/or retinal pigment epithelial cell viability.

In one aspect, the disclosure provides a method of preserving the visual function of an eye of a subject with an ocular condition, wherein a symptom of the ocular condition is the loss of photoreceptor cell viability in the retina of the eye with the condition. The method comprises administering to the eye of the subject an effective amount of a compound or composition described herein, thereby preserving the viability of the photoreceptor cells disposed within the retina of the eye. After administration, the visual function (e.g., visual acuity) of the eye may be preserved or improved relative to the visual function of the eye prior to administration.

The ocular condition may be a condition selected from the group consisting of age-related macular degeneration (AMD), retinosis pigmentosa (RP), macular edema, diabetic retinopathy, central areolar choroidal dystrophy, BEST disease, adult vitelliform disease, pattern dystrophy, myopic degeneration, central serous retinopathy, Stargardt's disease, Cone-Rod dystrophy, North Carolina dystrophy, infectious retinitis, inflammatory retinitis, uveitis, toxic retinitis and light-induced toxicity. AMD may be the neovascular or the dry form of AMD. Retinal detachment may be a rhegmatogenous, a serous or a tractional retinal detachment.

In another aspect, the disclosure provides a method of preserving the viability of retinal pigment epithelial (RPE) cells within the retina of a subject with an ocular condition, wherein a symptom of the ocular condition is the loss of retinal pigment epithelial cells in the retina of the eye with the condition. The method comprises administering to the eye of the subject an effective amount of a compound or composition described herein, thereby preserving the viability of the retinal pigment epithelial cells. The ocular condition may be selected from the group consisting of AMD, BEST disease, myopic degeneration, Stargardt's disease, uveitis, adult foveomacular dystrophy, fundus falvimaculatus, multiple evanescent white dot syndrome, serpiginous choroidopathy, acute multifocal posterior placoid epitheliopathy (AMPPE) and other uveitis disorders.

The ocular condition may be a condition selected from the group consisting of age-related macular degeneration (AMD), retinosis pigmentosa (RP), macular edema, diabetic retinopathy, central areolar choroidal dystrophy, BEST disease, adult vitelliform disease, pattern dystrophy, myopic degeneration, central serous retinopathy, Stargardt's disease, Cone-Rod dystrophy, North Carolina dystrophy, infectious retinitis, inflammatory retinitis, uveitis, toxic retinitis and light-induced toxicity. Therefore, in certain embodiments, the method comprises administering to the eye an effective amount of a compound or composition described herein, thereby preserving the viability of the photoreceptor cells disposed within the retina of the subject with a condition.

In another aspect, the disclosure provides a method of preserving the viability of photoreceptor cells disposed within a retina of a mammalian eye following retinal detachment. The method comprises administering a compound or composition described herein to the eye in which a region of the retina has been detached in amounts sufficient to preserve the viability of photoreceptor cells disposed within the region of the detached retina.

In certain embodiments, the retinal detachment may be a rhegmatogenous retinal detachment, tractional retinal detachment or serous retinal detachment. In certain embodiments, the retinal detachment may occur as a result of a retinal tear, retinoblastoma, melanoma or other cancers, diabetic retinopathy, uveitis, choroidal neovascularization, retinal ischemia, pathologic myopia or trauma.

In another aspect, the disclosure provides a method of preserving visual function of an eye of a subject with an ocular condition selected from the group consisting of AMD, RP, macular edema, central areolar choroidal dystrophy, retinal detachment, diabetic retinopathy, BEST disease, adult vitelliform disease, pattern dystrophy, myopic degeneration, central serous retinopathy, Stargardt's disease, Cone-Rod dystrophy, North Carolina dystrophy, infectious retinitis, inflammatory retinitis, uveitis, toxic retinitis and light-induced toxicity, wherein a symptom of the ocular condition is the loss of photoreceptor cells viability in the retina of the eye, wherein the method comprises treating the subject with a compound or composition described herein to the subject.

In another aspect, the disclosure provides a method of preserving the visual function of an eye of a subject with an ocular condition, wherein a symptom of the ocular condition is the loss of photoreceptor cell viability and/or RPE viability in the retina of the eye wherein the method comprises treating the subject with a compound or composition described herein to the subject.

In certain embodiments is provided a method of preserving the visual function of an eye of a subject with ocular conditions, wherein a symptom of the ocular condition is the loss of retinal ganglion cell viability in the retina of the eye with the conditions. The method comprises administering to the eye of the subject an effective amount of a compound or composition, thereby preserving the viability of the retinal ganglion cells disposed within the retina of the eye. After administration of the compound or composition, the visual function of the eye may be preserved or improved relative to the visual function of the eye prior to administration. Further, after the administration, the preserved retinal ganglion cell is capable of supporting axonal regeneration.

In each of the foregoing methods, the ocular condition, wherein a symptom of the condition is the loss of retinal ganglion cell viability in the retina of the eye, includes but is not limited to glaucoma, optic nerve injury, optic neuritis, optic neuropathies, diabetic retinopathy, central retinal artery occlusion and central retinal vein occlusion. It is contemplated that the forgoing methods may be used for the treatment of optic neuropathies such as ischemic optic neuropathy (e.g., arteritic or non-arteritic anterior ischemic neuropathy and posterior ischemic optic neuropathy), compressive optic neuropathy, infiltrative optic neuropathy, traumatic optic neuropathy, mitochondrial optic neuropathy (e.g., Leber's optic neuropathy), nutritional optic neuropathy, toxic optic neuropathy and hereditary optic neuropathy (e.g., Leber's optic neuropathy, Dominant Optic Atrophy, Behr's syndrome).

Also disclosed is a method of preserving the visual function of an eye of a subject with an ocular condition selected from the group consisting of glaucoma, optic nerve injury, optic neuropathies, diabetic retinopathy, central retinal artery occlusion and central retinal vein occlusion. The method comprises administering to the eye of the subject an effective amount of a compound or composition described herein, thereby preserving the viability of the retinal ganglion cells disposed within the retina of the eye and the visual function of the eye.

In another aspect, disclosed herein is a method of preserving the viability of retinal ganglion cells disposed within a retina of a mammalian eye affected by, for example, glaucoma, optic nerve injury, optic neuritis, optic neuropathies, diabetic retinopathy, central retinal artery occlusion and central retinal vein occlusion. The method comprises administering a compound or composition described herein to the eye in which a region of the retina has been affected in amounts sufficient to preserve the viability of retinal ganglion cells disposed within the region of the affected retina. The preserved retinal ganglion cell is capable of supporting axonal regeneration.

Also disclosed is a method for promoting axon regeneration in an eye of a subject with an ocular condition, wherein a symptom of the ocular condition is the loss of retinal ganglion cell viability in the retina of the eye with the condition. The method comprises administering to the eye of the subject an effective amount of a compound or composition described herein, thereby promoting axon regeneration of the retinal ganglion cell within the retina of the eye.

In each of the foregoing embodiments, it is understood that the methods and compositions described herein can be used to preserve the viability and/or promote axon regeneration of retinal ganglion cells during treatment of the underlying conditions including, but not limited to, glaucoma, optic nerve injury, optic neuritis, optic neuropathies, diabetic retinopathy, central retinal artery occlusion and central retinal vein occlusion.

Neurodegenerative and CNS Diseases

The receptor interacting protein kinase 1 inhibitors described herein may also be used to treat neurodegenerative diseases. Neurodegenerative diseases can affect many of the body's activities, such as balance, movement, talking, breathing and heart function. Neurodegenerative diseases can be genetic or caused by medical conditions such as alcoholism, tumors, strokes, toxins, chemicals and viruses.

Non-limiting examples of neurodegenerative diseases and CNS diseases include Niemann-Pick disease, type C1 (NPC1), Alzheimer's disease, amyotrophic lateral sclerosis (ALS), Friedreich's ataxia, Huntington's disease, Lewy body disease, Parkinson's disease and spinal muscular atrophy.

In an embodiment, the receptor interacting protein kinase 1 inhibitors described herein may be used to treat NPC1 via inhibiting necroptosis that causes neuronal loss. In certain embodiments, the compounds and compositions of the present disclosure are useful for treating Alzheimer's disease. In certain embodiments, the compounds and compositions of the present disclosure are useful for treating Parkinson's disease. In certain embodiments, the compounds and compositions of the present disclosure are useful for treating amyotrophic lateral sclerosis (ALS).

More generally, the receptor interacting protein kinase 1 inhibitors described herein can be used to preserve neuron viability and promote axon growth and nerve functions within the central nervous system (CNS). Accordingly, the compounds may be used to reduce or even reverse the loss of cognitive, motor and sensory functions associated with a CNS disease or disorder, by preserving neuron viability and/or promoting axon regeneration and/or nerve functions.

The receptor interacting protein kinase 1 inhibitors described herein can be used in a method for promoting axon regeneration in a CNS neuron, such as a CNS sensory neuron, a motor neuron, a cortical neuron, a cerebellar neuron, a hippocampal neuron and a midbrain neuron. The receptor interacting protein kinase 1 inhibitors described herein can be used in a method for promoting nerve function or preserving the viability following injury to a CNS neuron. In certain embodiments, these compounds can be used to promote regeneration of an axon in a CNS neuron that is degenerated in the CNS disease or disorder. The receptor interacting protein kinase 1 inhibitors may be administered by any conventional means, such as locally to the neuron or applied ex vivo before re-implantation.

Accordingly, in one aspect, the disclosure provides a method of treating a CNS disorder in a subject in need thereof, wherein a symptom of the CNS disorder is axon degeneration or injury within a CNS neuron. The method comprises administering to the subject an effective amount of a compound or composition disclosed herein thereby to promote regeneration of an axon in a CNS neuron affected by the CNS disorder. Following administration, neural functions may be measured, for example, as an indication of axon regeneration. It is also contemplated that, following administration of the compound or composition, the neuron function of the CNS neuron is preserved or improved relative to the neuron function prior to administration.

The CNS disorder includes, but is not limited to, brain injury, spinal cord injury, dementia, stroke, Alzheimer's disease, amyotrophic lateral sclerosis (ALS/Lou Gehrig's Disease), Parkinson's disease, Huntington's disease, multiple sclerosis, diabetic neuropathy, polyglutamine (polyQ) diseases, stroke, Fahr disease, Menke's disease, Wilson's disease, cerebral ischemia and a prion disorder. In exemplary embodiments, the CNS disorder is brain injury or spinal cord injury.

Also provided herein are methods for promoting neuron survival and axon regeneration in the CNS. CNS disorders characterized by impaired or failing axon growth or axon degeneration may arise from CNS neuron injury (e.g., trauma, surgery, nerve compression, nerve contusion, nerve transection, neurotoxicity or other physical injury to the brain or spinal cord) or neurodegenerative CNS disease, wherein a symptom of the disorder is axon degeneration (e.g., Alzheimer's disease, amyotrophic lateral sclerosis (ALS/Lou Gehrig's Disease), Parkinson's disease, multiple sclerosis, diabetic neuropathy, polyglutamine (polyQ) diseases, stroke, Fahr disease, Menke's disease, Wilson's disease, cerebral ischemia, prion disorder (e.g., Creutzfeldt-Jakob disease). In certain embodiments, the CNS disorder is brain injury (e.g., traumatic brain injury) or spinal cord injury (e.g., chronic, acute or traumatic spinal cord injury). In certain embodiments, the CNS disorder affects a subject's basic vital life functions such as breathing, heart beat and blood pressure, e.g., an injury to or aneurysm in the brain stem.

In certain embodiments, the CNS disorder affects a subject's cognitive ability, such as, brain injury to the cerebral cortex or a neurodegenerative CNS disorder, such as, Alzheimer's disease, frontotemporal dementia, dementia with Lewy bodies, corticobasal degeneration, progressive supranuclear palsy and prion disorders.

In certain embodiments, the CNS disorder affects a subject's movement and/or strength, such as injury to the brain or spinal cord or a neurodegenerative CNS disorder such as Parkinson's disease, frontotemporal dementia, dementia with Lewy bodies, corticobasal degeneration, progress supranuclear palsy, Huntington's disease, multiple system atrophy, amyotrophic lateral sclerosis and hereditary spastic paresis.

In certain embodiments, the CNS disorder affects a subject's coordination, such as brain injury to the cerebellum or a neurodegenerative CNS disorder such as spinocerebellar atrophies, Friedreich's ataxia and prion disorders.

In each of the foregoing methods, the CNS disorder includes, but is not limited to, brain injury, spinal cord injury, Alzheimer's disease, amyotrophic lateral sclerosis (ALS/Lou Gehrig's Disease), Parkinson's disease, multiple sclerosis, diabetic neuropathy, polyglutamine (polyQ) diseases, stroke, Fahr disease, Menke's disease, Wilson's disease, cerebral ischemia, a prion disorder (e.g., Creutzfeldt-Jakob disease), dementia (e.g., frontotemporal dementia, dementia with Lewy bodies), corticobasal degeneration, progressive supranuclear palsy, multiple system atrophy, hereditary spastic paraparesis and spinocerebellar atrophies.

Tissue Injuries or Damages

The ability of the compounds described herein to inhibit inflammation and cell death makes them suitable for ameliorating tissue injuries or damages. The tissue injuries or damages may be a result of any of the diseases or conditions described above. For example, the compounds may be used for amelioration of brain tissue injury or damage following ischemic brain injury or traumatic brain injury or for amelioration of heart tissue injury or damage following myocardial infarction or for amelioration of brain tissue injury or damage associated with Huntington's disease, Alzheimer's disease or Parkinson's disease or for amelioration of liver tissue injury or damage associated with non-alcohol steatohepatitis, alcohol steatohepatitis, autoimmune hepatitis, autoimmune hepatobiliary diseases or primary sclerosing cholangitis or for the amelioration of liver tissue injury or damage associated with overdose of acetaminophen or for amelioration of kidney tissue injury or damage following renal transplant or the administration of nephrotoxic drugs or substances.

Non-limiting examples of brain injury or damage include stroke (e.g., hemorrhagic and non-hemorrhagic), traumatic brain injury (TBI), cerebral hemorrhage, subarachnoid hemorrhage, intracranial hemorrhage secondary to cerebral arterial malformation, cerebral infarction, perinatal brain injury, non-traumatic brain injury, Alzheimer's disease, Parkinson's disease, Huntington's disease, multiple sclerosis, amyotrophic lateral sclerosis, brain hemorrhage, brain infections, brain tumor, subclinical brain injury, spinal cord injury, anoxic-ischemic brain injury, focal cerebral ischemia, global cerebral ischemia, and hypoxic hypoxia.

In an embodiment, the compounds and compositions of the present disclosure may be used to treat peritoneal tissue injury. Non-limiting examples of peritoneal tissue injury include peritoneal deterioration, peritoneal sclerosis, and peritoneal cancer. For example, the receptor interacting protein kinase 1 inhibitors described herein may be used to treat peritoneal damage caused by peritoneal dialysis fluid (PDF) and PD-related side effects.

Liver Injury and Diseases

In an embodiment, the compounds and compositions of the present disclosure may be used to treat liver injury and diseases. Non-limiting examples of liver injury or damage include not only degeneration or necrosis of liver parenchyma cells which results from injury caused by a certain factor, but also undesirable phenomena caused by biological reactions to the injury, such as mobilization, infiltration, activation of Kupffer cells, leukocytes and the like, fibrosis of the liver tissue, etc., which reactions occur alone or in combination. In an embodiment, the receptor interacting protein kinase 1 inhibitors described herein may be used to treat steatohepatitis and hepatocellular carcinoma via inhibiting receptor interacting protein kinase 1 activity-dependent apoptosis of hepatocytes and hepatocarcinogenesis. In an embodiment, the receptor interacting protein kinase 1 inhibitors described herein may be used to treat acute cholestasis and liver injury.

Kidney Injury and Diseases

In an embodiment, the compounds and compositions of the present disclosure may be used to treat kidney injury and diseases. Non-limiting examples of kidney diseases include chronic kidney disease (CKD) (e.g., glomerular diseases, tubulointerstitial diseases, obstruction, polycystic kidney disease), acute kidney injury (AKI), diabetic nephropathy, glomerulonephritis, focal glomerulosclerosis, immune complex nephropathy or lupus nephritis. Kidney disease may be caused by drug-induced renal injury or kidney graft rejection. Kidney disease may be characterized as nephrotic syndrome or renal insufficiency. In an embodiment, the receptor interacting protein kinase 1 inhibitors described herein may be used to treat kidney diseases (e.g., AKI) via inhibiting cell death pathway in kidney diseases. In an embodiment, the receptor interacting protein kinase 1 inhibitors described herein may be used to treat patient with kidney stones and to prevent crystal-induced cytotoxicity and acute kidney injury via inhibiting receptor interacting protein kinase 3-MLKL-mediated necroptosis.

Malignancies

In an embodiment, the compounds and compositions of the present disclosure are useful for treating malignancies/cancers such as carcinoma, sarcoma, melanoma, lymphoma or leukemia. Non-limiting examples of malignancies suitably treated by the receptor interacting protein kinase 1 inhibitors described herein include lung cancer (e.g. non-small cell lung cancer, small-cell lung cancer), hepatocellular cancer, melanoma, pancreatic cancer, urological cancer, bladder cancer, colorectal cancer, colon cancer, breast cancer, prostate cancer, renal cancer, thyroid cancer, gall bladder cancer, peritoneal cancer, ovarian cancer, cervical cancer, gastric cancer, endometrial cancer, esophageal cancer, head and neck cancer, neuroendocrine cancer, CNS cancer, brain tumors (e.g., glioma, anaplastic oligodendroglioma, adult glioblastoma multiforme, and adult anaplastic astrocytoma), bone cancer, soft tissue sarcoma, retinoblastomas, neuroblastomas, peritoneal effusions, malignant pleural effusions, mesotheliomas, Wilms tumors, trophoblastic neoplasms, hemangiopericytomas, Kaposi's sarcomas, myxoid carcinoma, round cell carcinoma, squamous cell carcinomas, esophageal squamous cell carcinomas, oral carcinomas, vulval cancer, cancers of the adrenal cortex, ACTH producing tumors, lymphoma, and leukemia.

Infectious Diseases

In an embodiment, the compounds and compositions of the present disclosure are useful for treating infectious diseases resulting from the presence of pathogenic agents, including pathogenic viruses, pathogenic bacteria, fungi, protozoa, multicellular parasites and aberrant proteins known as prions. Non-limiting examples of infectious diseases suitably treated by the receptor interacting protein kinase 1 inhibitors described herein include virus infectious diseases and bacterial infectious diseases. The virus infectious disease is not particularly limited and includes, for example, infectious diseases with respiratory infectious viruses (e.g., infectious diseases due to respiratory infectious viruses such as influenza virus, rhino virus, corona virus, parainfluenza virus, RS virus, adeno virus, reo virus and the like), herpes zoster caused by herpes virus, diarrhea caused by rotavirus, viral hepatitis, AIDS and the like. The bacterial infectious disease is not particularly limited and includes, for example, infectious diseases caused by *Bacillus cereus, Vibrio parahaemolyticus*, Enterohemorrhagic *Escherichia coli, Staphylococcus aureus*, MRSA, *Salmonella, Botulinus, Candida* and the like.

Bone Diseases

In an embodiment, the compounds and compositions of the present disclosure are useful for treating bone diseases that may result from a bone remodeling disorder whereby the balance between bone formation and bone resorption is shifted. Non-limiting examples of bone remodeling disorders include osteoporosis, Paget's disease, osteoarthritis, rheumatoid arthritis, achondroplasia, osteochodrytis, hyperparathyroidism, osteogenesis imperfecta, congenital hypophosphatasia, fribromatous lesions, fibrous dysplasia, multiple myeloma, abnormal bone turnover, osteolytic bone disease and periodontal disease. Additional examples of bone diseases suitably treated by the receptor interacting protein kinase 1 inhibitors described herein include bone fracture, bone trauma, or a bone deficit condition associated with post-traumatic bone surgery, post-prosthetic joint surgery, post-plastic bone surgery, post-dental surgery, bone chemotherapy treatment or bone radiotherapy treatment. Additional examples of diseases affecting bone or bone joints suitably treated by the receptor interacting protein kinase 1 inhibitors described herein include metastatic bone cancer, rheumatic diseases such as rheumatoid arthritis, osteoarthritis and other inflammatory arthropathies. In an embodiment, the receptor interacting protein kinase 1 inhibitors described herein may be used to treat postmenopausal osteoporosis via inhibiting osteocyte necroptosis and trabecular deterioration.

Cardiovascular Diseases

In an embodiment, the compounds and compositions of the present disclosure are useful for treating cardiovascular diseases that may be relate to the cardiovascular disorders of fragile plaque disorder, occlusive disorder and stenosis. Non-limiting cardiovascular diseases include coronary artery disorders and peripheral arterial disorders, including, among others, atherosclerosis, arterial occlusion, aneurysm formation, thrombosis, post-traumatic aneurysm formation, restenosis, and post-operative graft occlusion. It is believed that atherosclerosis results from maladaptive inflammation driven primarily by macrophages. Thus, the compounds and compositions of the present disclosure may be used to treat atherosclerosis via inhibiting macrophage necroptosis.

Transplantation

In an embodiment, the compounds and compositions of the present disclosure are useful for treating transplant patients. Non-limiting examples of transplant patient suitably treated by the receptor interacting protein kinase 1 inhibitors described herein include patients with solid and non-solid organ and tissue transplantations and transplants, such as liver, heart, kidney, and heterologous and autologous bone marrow transplantations/transplants. Typically, immunosuppressive therapy is used to avoid graft rejection in recipients of solid organ transplants. Recipients of bone marrow transplants are usually subjected to extensive irradiation and chemotherapy prior to transplantation. It is believed that receptor interacting protein kinase 1 and NF-κB signaling in dying cells determines cross-priming of CD8+ T cells. Thus, the receptor interacting protein kinase 1 inhibitors described herein may be used to treat transplant patient and avoid graft rejection by modulating cross-priming of CD8+ T cells.

Other Diseases and Conditions

Additional examples of diseases and disorders suitably treated by the receptor interacting protein kinase 1 inhibitors described herein include Gaucher disease, organ failure, pancreatitis (e.g., acute pancreatitis), atopic dermatitis, spondyloarthritis, gout, systemic onset juvenile idiopathic arthritis (SoJIA), systemic lupus erythematosus (SLE), Sjogren's syndrome, systemic scleroderma, anti-phospholipid syndrome (APS), vasculitis, primary sclerosing cholangitis (PSC), acetaminophen toxicity, kidney damage/injury (nephritis, renal transplant, surgery, administration of nephrotoxic drugs e.g. cisplatin, acute kidney injury (AKI)), Celiac disease, autoimmune idiopathic thrombocytopenic purpura (autoimmune ITP), cerebrovascular accident (CVA, stroke), myocardial infarction (MI), allergic diseases (including asthma), diabetes, Wegener's granulomatosis, pulmonary sarcoidosis, Behcet's disease, interleukin-1 converting enzyme (ICE/caspase-1) associated fever syndrome, chronic obstructive pulmonary disease (COPD), tumor necrosis factor receptor-associated periodic syndrome (TRAPS), peridontitis, NEMO-deficiency syndrome (F-kappa-B essential modulator gene (also known as IKK gamma or IKKG) deficiency syndrome), HOIL-1 deficiency ((also known as RBCK1) heme-oxidized IRP2 ubiquitin ligase-1 deficiency), linear ubiquitin chain assembly complex (LUBAC) deficiency syndrome, hematological and solid organ malignancies, bacterial infections (e.g., *Staphylococcus* infection and mycobacterium infection) and viral infections (e.g., tuberculosis and influenza) and lysosomal storage diseases.

Non-limiting examples of lysosomal storage diseases include Gaucher disease, GM2 Gangliosidosis, alpha-mannosidosis, aspartylglucosaminuria, cholesteryl ester storage disease, chronic hexosaminidase A deficiency, cystinosis, Danon disease, Fabry disease, Farber disease, fucosidosis, galactosialidosis, GM1 gangliosidosis, mucolipidosis, infantile free sialic acid storage disease, juvenile hexosaminidase A deficiency, Krabbe disease, lysosomal acid lipase deficiency, metachromatic leukodystrophy, mucopolysaccharidoses disorders, multiple sulfatase deficiency, Niemann-Pick disease, neuronal ceroid lipofuscinoses, Pompe disease, pycnodysostosis, Sandhoff disease, Schindler disease, sialic acid storage disease, Tay-Sachs and Wolman disease.

In certain embodiments, provided are compounds and compositions for use in medicine. In certain embodiments, the compounds and compositions are for use in the treatment of a receptor interacting protein kinase 1-mediated disease or disorder. Also provided is a method of treating a receptor interacting protein kinase 1-mediated disease or disorder comprising administering a therapeutically effective amount of a compound or pharmaceutical composition disclosed herein to a subject in need thereof.

5. Compositions

For the purposes of administration, the compounds of the present disclosure may be administered as a raw chemical or may be formulated as pharmaceutical compositions. Pharmaceutical compositions of the present disclosure comprise a compound of Formula I and a pharmaceutically acceptable carrier, diluent or excipient. Accordingly, different embodiments are directed to pharmaceutical compositions comprising any one or more of the foregoing compounds of Formula I or a pharmaceutically acceptable salt, prodrug, stereoisomer or a mixture of stereoisomers thereof and a pharmaceutically acceptable carrier, diluent or excipient are also provided in various embodiments.

The pharmaceutical compositions of the present disclosure may be specially formulated for administration in solid or liquid form, including those adapted for the following: oral administration, for example, drenches (aqueous or non-aqueous solutions or suspensions), tablets, e.g., those targeted for buccal, sublingual and systemic absorption, boluses, powders, granules, pastes for application to the tongue; parenteral administration, for example, by subcutaneous, intramuscular, intravenous or epidural injection as, for example, a sterile solution or suspension or sustained-release formulation; topical application, for example, as a cream, ointment or a controlled-release patch or spray applied to the skin; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient or solvent encapsulating material, involved in carrying or transporting the subject compound from one organ or portion of the body, to another organ or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose and its derivatives, such as sodium carboxymethyl cellulose, ethyl cellulose and cellulose acetate; surfactants, such as polysorbate 80 (i.e., Tween 80); powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Examples of such formulations include, but are not limited to DMSO, 10 mM DMSO, 8% hydroxypropyl-beta-cyclodextrin in PBS, propylene glycol, etc. For example, in a certain embodiment the compounds of the disclosure can be used as 4 mM solution in 8% hydroxypropyl-beta-cyclodextrin in PBS for parenteral administration. In another certain embodiments, the compounds of the disclosure can be used as a suspension in 0.5% aqueous CMC containing 0.1% TWEEN 80.

As set out herein, certain embodiments of the present compounds may contain a basic functional group, such as amino or methylamino ($NCH_3$) and are, thus, capable of forming pharmaceutically-acceptable salts with pharmaceutically-acceptable acids. The term "pharmaceutically-acceptable salts" in this respect refers to the relatively non-toxic, inorganic and organic acid addition salts of compounds of the present disclosure. These salts can be prepared in situ in the administration vehicle or the dosage form manufacturing process or by separately reacting a purified compound of the disclosure in its free base form with a suitable organic or inorganic acid and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate and laurylsulphonate salts and the like.

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic and the like.

In other cases, the compounds of the present disclosure may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present disclosure. These salts can likewise be prepared in situ in the administration vehicle or the dosage form manufacturing process or by separately reacting the purified compound in its free acid form with a suitable base, such as the hydroxide, carbonate or bicarbonate of a pharmaceutically-acceptable metal cation, with ammonia or with a pharmaceutically-acceptable organic primary, secondary or tertiary amine. Representative alkali or alkaline earth salts include the lithium, sodium, potassium, calcium, magnesium and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol and the like; and metal chelating agents, such as citric acid, ethylenediamine tetraacetic acid (EDTA), sorbitol, tartaric acid, phosphoric acid and the like.

Formulations of the present disclosure include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, this amount will range from about 1% to about 99% of active ingredient, preferably from about 5% to about 70%, most preferably from about 10% to about 30%.

In certain embodiments, a formulation of the present disclosure comprises an excipient selected from the group consisting of cyclodextrins, liposomes, micelle forming agents, e.g., bile acids and polymeric carriers, e.g., polyesters and polyanhydrides; and a compound of the present disclosure. In certain embodiments, an aforementioned formulation renders orally bioavailable a compound of the present disclosure.

Methods of preparing these formulations or compositions include the step of bringing into association a compound of the present disclosure with the carrier and, optionally, one or more accessory ingredients. In general, the formulations are prepared by uniformly and intimately bringing into association a compound of the present disclosure with liquid carriers or finely divided solid carriers or both and then, if necessary, shaping the product.

Formulations of the disclosure suitable for oral administration may be in the form of capsules, cachets, pills, tablets, lozenges (using a flavored basis, usually sucrose and acacia or tragacanth), powders, granules or as a solution or a suspension in an aqueous or non-aqueous liquid or as an oil-in-water or water-in-oil liquid emulsion or as an elixir or syrup or as pastilles (using an inert base, such as gelatin and glycerin or sucrose and acacia) and/or as mouth washes and the like, each containing a predetermined amount of a compound of the present disclosure as an active ingredient. A compound of the present disclosure may also be administered as a bolus, electuary or paste.

In solid dosage forms of the disclosure for oral administration (capsules, tablets, pills, dragees, powders, granules and the like), the active ingredient is mixed with one or more pharmaceutically-acceptable carriers, such as sodium citrate or dicalcium phosphate and/or any of the following: fillers or extenders, such as starches, lactose, sucrose, glucose, mannitol and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates and sodium carbonate; solution retarding agents, such as paraffin; absorption accelerators, such as quaternary ammonium compounds; wetting agents, such as, for example, cetyl alcohol, glycerol monostearate and non-ionic surfactants; absorbents, such as kaolin and bentonite clay; lubricants, such a talc, calcium stearate, magnesium stearate, solid polyethylene glycols, sodium lauryl sulfate and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

The tablets and other solid dosage forms of the pharmaceutical compositions of the present disclosure, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter or by incorporating sterilizing agents in the form of sterile solid compositions that can be dissolved in sterile water or some other sterile injectable medium immediately before use. These compositions may also optionally contain opacifying agents and may be of a composition that they release the active ingredient(s) only or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the disclosure include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth and mixtures thereof.

Formulations of the pharmaceutical compositions of the disclosure for rectal or vaginal administration may be presented as a suppository, which may be prepared by mixing one or more compounds of the disclosure with one or more suitable nonirritating excipients or carriers comprising, for example, cocoa butter, polyethylene glycol, a suppository wax or a salicylate and which is solid at room temperature, but liquid at body temperature and, therefore, will melt in the rectum or vaginal cavity and release the active compound.

Formulations of the present disclosure which are suitable for vaginal administration also include pessaries, tampons, creams, gels, pastes, foams or spray formulations containing such carriers as are known in the art to be appropriate.

Dosage forms for the topical or transdermal administration of a compound of this disclosure include powders, sprays, ointments, pastes, creams, lotions, gels, solutions, patches and inhalants. The active compound may be mixed under sterile conditions with a pharmaceutically-acceptable carrier and with any preservatives, buffers or propellants which may be required.

The ointments, pastes, creams and gels may contain, in addition to an active compound of this disclosure, excipients, such as animal and vegetable fats, oils, waxes, paraffins, starch, tragacanth, cellulose derivatives, polyethylene glycols, silicones, bentonites, silicic acid, talc and zinc oxide or mixtures thereof.

Powders and sprays can contain, in addition to a compound of this disclosure, excipients such as lactose, talc, silicic acid, aluminum hydroxide, calcium silicates and polyamide powder or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present disclosure to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Ophthalmic formulations, eye ointments, powders, solutions and the like, are also contemplated as being within the scope of this disclosure.

Pharmaceutical compositions of this disclosure suitable for parenteral administration comprise one or more compounds of the disclosure in combination with one or more pharmaceutically-acceptable sterile isotonic aqueous or non-aqueous solutions, dispersions, suspensions or emulsions or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the disclosure include water, ethanol, polyols (such as glycerol, propylene glycol, polyethylene glycol and the like) and suitable mixtures thereof, vegetable oils, such as olive oil and injectable organic esters, such as ethyl oleate. Proper fluidity can be maintained, for example, by the use of coating materials, such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenyl sorbic acid and the like. It may also be desirable to include isotonic agents, such as sugars, sodium chloride and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

6. Dosing

The phrases "parenteral administration" and "administered parenterally" as used herein means modes of administration other than enteral and topical administration, usually by injection and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present disclosure, which may be used in a suitable hydrated form and/or the pharmaceutical compositions of the present disclosure, are formulated into pharmaceutically-acceptable dosage forms by conventional methods known to those of skill in the art.

Actual dosage levels of the active ingredients in the pharmaceutical compositions of this disclosure may be varied so as to obtain an amount of the active ingredient that is effective to achieve the desired therapeutic response for a particular patient, composition and mode of administration, without being toxic to the patient.

The selected dosage level will depend upon a variety of factors including the activity of the particular compound of the present disclosure employed or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated and like factors well known in the medical arts. A daily, weekly or monthly dosage (or other time interval) can be used.

A physician or veterinarian having ordinary skill in the art can readily determine and prescribe the effective amount of the pharmaceutical composition required. For example, the physician or veterinarian could start doses of the compounds of the disclosure employed in the pharmaceutical composition at levels lower than that required to achieve the desired therapeutic effect and then gradually increasing the dosage until the desired effect is achieved.

In general, a suitable daily dose of a compound of the disclosure will be that amount of the compound that is the lowest dose effective to produce a therapeutic effect (e.g., inhibit necrosis). Such an effective dose will generally depend upon the factors described above. Generally doses of the compounds of this disclosure for a patient, when used for the indicated effects, will range from about 0.0001 to about 100 mg per kg of body weight per day. Preferably the daily dosage will range from 0.001 to 50 mg of compound per kg of body weight and even more preferably from 0.01 to 10 mg of compound per kg of body weight.

If desired, the effective daily dose of the active compound may be administered as two, three, four, five, six or more sub-doses administered separately at appropriate intervals throughout the day, optionally, in unit dosage forms.

In certain embodiments, the present disclosure relates to compounds for inhibiting cell death, wherein the compounds are represented by structures (I). In certain embodiments, the compounds of the present disclosure are inhibitors of cell death. In any event, the compounds of the present disclosure preferably exert their effect on inhibiting cell death at a concentration less than about 50 micromolar, more preferably at a concentration less than about 10 micromolar and most preferably at a concentration less than 1 micromolar.

The compounds of the disclosure can be tested in standard animal models of stroke and standard protocols such as described by Hara, H., et al. Proc Natl Acad Sci USA, 1997. 94 (5): 2007-12.

When the compounds of the present disclosure are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

The compounds of the present application or the compositions thereof may be administered once, twice, three or four times daily, using any suitable mode described above. Also, administration or treatment with the compounds may be continued for a number of days; for example, commonly treatment would continue for at least 7 days, 14 days or 28 days, for one cycle of treatment. Treatment cycles are well known and are frequently alternated with resting periods of about 1 to 28 days, commonly about 7 days or about 14 days, between cycles. The treatment cycles, in certain embodiments, may also be continuous.

When administered orally, the total daily dosage for a human subject may be between 1 mg and 1,000 mg, between about 1,000-2,000 mg/day, between about 10-500 mg/day, between about 50-300 mg/day, between about 75-200 mg/day or between about 100-150 mg/day.

The daily dosage may also be described as a total amount of a compound described herein administered per dose or per day. Daily dosage of a compound may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day or between about 15 to 150 mg/day.

In certain embodiments, the method comprises administering to the subject an initial daily dose of about 1 to 800 mg of a compound described herein and increasing the dose by increments until clinical efficacy is achieved. Increments of about 5, 10, 25, 50 or 100 mg can be used to increase the dose. The dosage can be increased daily, every other day, twice per week or once per week.

In certain embodiments, a compound or pharmaceutical preparation is administered orally. In certain embodiments, the compound or pharmaceutical preparation is administered intravenously. Alternative routes of administration include sublingual, intramuscular and transdermal administrations.

The preparations of the present disclosure may be given orally, parenterally, topically or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. In certain embodiments, the administration is oral.

7. Combinations

In another aspect of the disclosure the compounds can be administered in combination with other agents, including (but not limited to) compounds that are apoptosis inhibitors; PARP poly(ADP-ribose) polymerase inhibitors; Src inhibitors; agents for the treatment of cardiovascular disorders; anti-inflammatory agents, anti-thrombotic agents; fibrinolytic agents; anti-platelet agents, lipid reducing agents, direct thrombin inhibitors; glycoprotein IIb/IIIc receptor inhibitors; calcium channel blockers; beta-adrenergic receptor blocking agents; cyclooxygenase (e.g., COX-1 and COX-2) inhibitors; angiotensin system inhibitor (e.g., angiotensin-converting enzyme (ACE) inhibitors); renin inhibitors; and/or agents that bind to cellular adhesion molecules and inhibit the ability of white blood cells to attach to such molecules (e.g., polypeptides, polyclonal and monoclonal antibodies).

Embodiments of the disclosure also provide combinations of two or more compounds that inhibit cellular necrosis (e.g., a compound as disclosed herein and an additional agent for inhibiting necrosis). The disclosure also provides combinations of one or more compounds that inhibit cellular necrosis combined with one or more additional agents or compounds (e.g., other therapeutic compounds for treating a disease, condition or infection such as an apoptosis inhibitor).

8. Kits

Provided herein are also kits that include a compound of the disclosure, combinations, or a pharmaceutically acceptable salt, prodrug, stereoisomer or a mixture of stereoisomers thereof and suitable packaging. In certain embodiments, a kit further includes instructions for use. In one aspect, a kit includes a compound of the disclosure or a pharmaceutically acceptable salt, prodrug, stereoisomer or a mixture of stereoisomers thereof and a label and/or instructions for use of the compounds in the treatment of the indications, including the diseases or conditions, described herein.

Provided herein are also articles of manufacture that include a compound described herein or a pharmaceutically acceptable salt, prodrug, stereoisomer or a mixture of stereoisomers thereof in a suitable container. The container may be a vial, jar, ampoule, preloaded syringe and intravenous bag.

The kit can also contain instructions for using the compounds according to the disclosure. The kit can be compartmentalized to receive the containers in close confinement. As used herein, a kit such as a compartmentalized kit includes any kit in which compounds or agents are contained in separate containers. Illustrative examples of such containers include, but are not limited to, small glass containers, plastic containers or strips of plastic or paper. Particularly preferred types of containers allow the skilled worker to efficiently transfer reagents from one compartment to another compartment such that the samples and reagents are not cross-contaminated and the agents or solutions of each container can be added in a quantitative fashion from one compartment to another. Such containers include, but are not limited to, a container that will accept a compound or combination of compounds and/or other agents of the disclosure. One or more compounds or agents can be provided as a powder (e.g. lyophilized powder) or precipitate. Such compound(s) can be resuspended prior to administration in a solution that may be provided as part of the kit or separately available. A kit can contain compounds or agents in other forms such as liquids, gels, solids, as described herein. Different compounds and/or agents may be provided in different forms in a single kit.

EXAMPLES

The examples and preparations provided below further illustrate and exemplify the compounds of the present disclosure and methods for testing such compounds. It is to be understood that the scope of the present disclosure is not limited in any way by the scope of the following examples. In the following examples and throughout the specification and claims, molecules with a chiral center, unless otherwise noted, exist as a mixture of stereoisomers. Single enantiomers may be obtained by methods known to those skilled in the art and described herein. Compounds were named by using either ChemBioDraw Ultra 13.0 or ChemAxon.

General Procedures

All solvents used were commercially available and were used without further purification. Reactions were typically run using anhydrous solvents under an inert atmosphere of nitrogen.

Analytical Methods $^1$H Nuclear magnetic resonance (NMR) spectroscopy was carried out using one of the following instruments: a Bruker Avance 400 instrument equipped with probe DUAL 400 MHz S1, a Bruker Avance 400 instrument equipped with probe 6 S1 400 MHz 5 mm $^1$H-$^{13}$C ID, a Bruker Avance III 400 instrument with nanobay equipped with probe Broadband BBFO 5 mm direct, a Broker Mercury Plus 400 NMR spectrometer equipped with a Bruker 400 BBO probe with all operating at 400 MHz. All deuterated solvents contained typically 0.03% to 0.05% v/v tetramethylsilane, which was used as the reference signal (set at δ 0.00 for both $^1$H and $^{13}$C). In certain cases, $^1$H Nuclear magnetic resonance (NMR) spectroscopy was carried out using a Bruker Advance 400 instrument operating at 400 MHz using the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; br, broad.

Where thin layer chromatography (TLC) has been used it refers to silica gel TLC using silica gel F254 (Merck) plates, Rf is the distance travelled by the compound divided by the distance travelled by the solvent on a TLC plate. Column chromatography was performed using an automatic flash chromatography system over silica gel cartridges or in the case of reverse phase chromatography over C18 cartridges. Alternatively, thin layer chromatography (TLC) was performed on Alugram® (Silica gel 60 F254) from Mancherey-Nagel and UV was typically used to visualize the spots. Additional visualization methods were also employed in some cases. In these cases the TLC plate was developed with iodine (generated by adding approximately 1 g of $I_2$ to 10 g silica gel and thoroughly mixing), ninhydrin (available commercially from Aldrich), or Magic Stain (generated by thoroughly mixing 25 g $(NH_4)_6Mo_7O_{24}.4H_2O$, 5 g $(NH_4)_2Ce(IV)(NO_3)_6$ in 450 mL water and 50 mL concentrated $H_2SO_4$) to visualize the compound.

Liquid Chromatography-Mass Spectrometry Method A: Total ion current (TIC) and DAD UV chromatographic traces together with MS and UV spectra associated with the peaks were taken on a UPLC/MS Acquity™ system equipped with PDA detector and coupled to a Waters single quadrupole mass spectrometer operating in alternated positive and negative electrospray ionization mode. [LC/MS-ES (+/−): analyses performed using an Acquity UPLC™ CSH, C18 column (50×2.1 mm, 1.7 μm particle size), column temperature 40° C., mobile phase: A—water+0.1% HCOOH/B—CH3CN+0.1% HCOOH, flow rate: 1.0 mL/min, runtime=2.0 min, gradient: t=0 min 3% B, t=1.5 min 99.9% B, t=1.9 min 99.9% B, t=2.0 min 3% B, stop time 2.0 min. Positive ES 100-1000, Negative ES 100-1000, UV detection DAD 210-350 nm.

Liquid Chromatography-Mass Spectrometry Method B: Total ion current (TIC) and DAD UV chromatographic traces together with MS and UV spectra associated with the peaks were taken on a UPLC/MS Acquity™ system equipped with PDA detector and coupled to a Waters single quadrupole mass spectrometer operating in alternated positive and negative electrospray ionization mode. The column used was a Cortecs UPLC C18, 1.6 μm, 2.1×50 mm. A linear gradient was applied, starting at 95% A (A: 0.1% formic acid in water) and ending at 95% B (B: 0.1% formic acid in MeCN) over 2.0 min with a total run time of 2.5 min. The column temperature was at 40° C. with the flow rate of 0.8 mL/min.

Liquid Chromatography-Mass Spectrometry Method C: Total ion current (TIC) and DAD UV chromatographic traces together with MS and UV spectra associated with the peaks were taken on a UPLC/MS Acquity™ system equipped with PDA detector and coupled to a Waters single quadrupole mass spectrometer operating in alternated positive and negative electrospray ionization mode. [LC/MS-ES (+/−): analyses performed using an Acquity UPLC™ BEH, C18 column (50×2.1 mm, 1.7 μm particle size), column temperature 40° C., mobile phase: A—0.1% v/v aqueous ammonia solution pH 10/B—CH3CN, flow rate: 1.0 mL/min, runtime=2.0 min, gradient: t=0 min 3% B, t=1.5 min 99.9% B, t=1.9 min 99.9% B, t=2.0 min 3% B, stop time 2.0 min. Positive ES 100-1000, Negative ES 100-1000, UV detection DAD 210-350 nm.

Preparative HPLC Method D: Preparative liquid chromatography were performed on a WATERS AUTOPREP HPLC. The Diode Array Detector was scanned from 190-400 nm. The mass spectrometer was equipped with an electrospray ion source (ESI) operated in a positive or negative mode. The mass spectrometer was scanned between m/z 90-900 with a scan time from 0.5 to 1.0 s. The column used was a Luna C18, 5 μm, 100×3000 mm. The column was eluted with 95% A (A: 0.1% NH$_4$HCO$_3$ in water) and 5% B (B: 0.1% NH$_4$HCO$_3$ in MeCN) for 1 min. A linear gradient was then applied, starting at 70% A and ending at 70% B over 15 min. The column temperature was at rt with a flow rate of 25 mL/min.

Liquid Chromatography-Mass Spectrometry Method E: The column used for chromatography was an Xtimate C18 2.1×30 mm, (3 μm particles). Detection methods are diode array (DAD). MS mode was positive electrospray ionization. MS range was 100-1000. Mobile phase A was 0.037% trifluoroacetic acid in water, and mobile phase B was 0.018% trifluoroacetic acid in HPLC grade acetonitrile. The gradient was 5-95% B (0.00-1.00 min) 95-100% B (1.00-1.80 min) 100-5% B (1.80-1.81 min) with a hold at 5% B for 0.19 min. The flow rate was 1.0 mL/min.

Intermediate 1

5-chloro-2,2-dimethyl-pentanoyl chloride

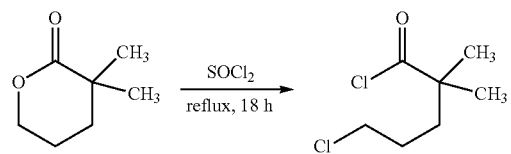

3,3-Dimethyltetrahydropyran-2-one (2.0 g, 15.6 mmol) was dissolved in thionyl chloride (30 g, 252 mmol). The reaction mixture was heated at reflux for 18 h, cooled to rt and concentrated in vacuo to yield the title compound. The crude product was used in the next step without purification. LCMS (Method B): m/z=183.1, 185.1 [M+H]$^+$.

Intermediate 2

O1-tert-butyl O3-methyl 2-(3-chloropropyl)-2-methyl-propanedioate

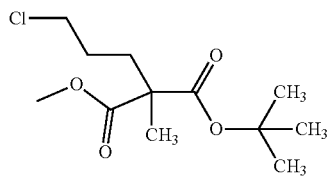 [SMILES: COC(=O)C(C)(CCCCl)C(=O)OC(C)(C)C]

O1-tert-Butyl O3-methyl 2-methylpropanedioate (11.6 g, 61.6 mmol) was added to a suspension of sodium hydride (3.2 g, 60%, 80.1 mmol) in DMF (100 mL) at 0° C. The reaction mixture was stirred at rt for 30 min before 1-bromo-3-chloro-propane (12.5 g, 79.1 mmol) was added in one portion. The mixture was stirred overnight at rt. The reaction mixture was diluted with water (200 mL) and ethyl acetate (200 mL). The organic layer was separated and washed with water (100 mL×2) and brine (150 mL) before concentrating under reduced pressure. The crude product was purified by flash chromatography (0-20% ethyl acetate in hexanes) to yield the title compound. LCMS (Method B): m/z=265.2, 267.3 [M+H]$^+$.

The following intermediate was prepared using methods analogous to the one described above.

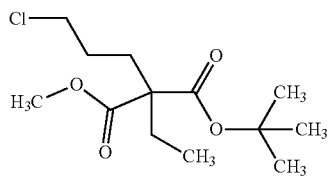 [SMILES: CCC(CCCCl)(C(=O)OC)C(=O)OC(C)(C)C]

Intermediate 3 tert-butyl 5-chloro-2-formyl-2-methyl-pentanoate

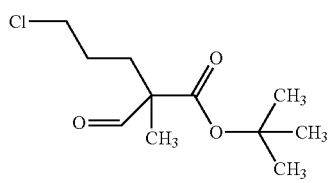

DIBAL (93.1 mL, 1.0 M, 93.1 mmol) was added via additional funnel to a solution of O1-tert-butyl O3-methyl 2-(3-chloropropyl)-2-methyl-propanedioate (11.2 g, 42.3 mmol) in DCM (100 mL) at −78° C. under argon. The reaction mixture was stirred at −78° C. for 1 h and then quenched by adding sat. NH$_4$Cl solution (50 mL) at −78° C. The mixture was warmed to rt then extracted with ethyl acetate (100 mL×2). The organic layers were collected then washed with water (100 mL) and brine (100 mL) before concentrating under reduced pressure. The residue was purified by flash chromatography to yield the title compound as a colorless oil (6.1 g, 61%). LCMS (Method B): m/z=235.2, 237.3 [M+H]$^+$.

The following intermediate was prepared using methods analogous to the one described above.

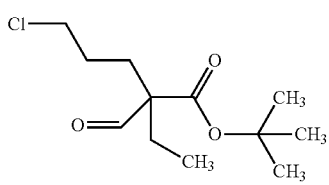 [SMILES: CCC(C=O)(CCCCl)C(=O)OC(C)(C)C]

Intermediate 4 tert-butyl 5-chloro-2-(difluoromethyl)-2-methyl-pentanoate

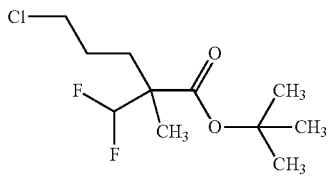 [SMILES: CC(C)(C)OC(=O)C(C)(CCCCl)C(F)F]

Bis(2-methoxyethyl)aminosulfur trifluoride (2.52 mL, 2.7 M, 6.82 mmol) was added to a solution of tert-butyl 5-chloro-2-formyl-2-methyl-pentanoate (0.80 g, 3.41 mmol) in DCE (5 mL). The reaction mixture was stirred at rt for 18 h. The reaction mixture was diluted with ethyl acetate (30 mL) then washed with sat. NaHCO$_3$ solution (20 mL), water (20 mL) and brine (30 mL) before concentrating under reduced pressure. The residue was purified by flash chromatography (0-25% ethyl acetate in hexanes) to yield the title compound as a colorless oil (0.51 g, 58%). LCMS (Method B): m/z=257.2, 259.3 [M+H]$^+$.

The following intermediate was prepared using methods analogous to the one described above.

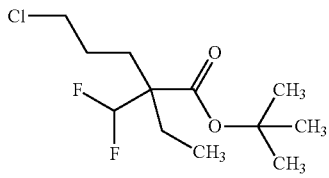 [SMILES: CCC(CCCCl)(C(=O)OC(C)(C)C)C(F)F]

Intermediate 5

5-chloro-2-(difluoromethyl)-2-methyl-pentanoic acid

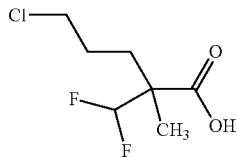

TFA (2 mL) was added to a solution of tert-butyl 5-chloro-2-(difluoromethyl)-2-methyl-pentanoate (233 mg, 0.91 mmol) in DCM (2 mL). The mixture was stirred at rt for 1 h. The reaction mixture was concentrated under reduced pressure to yield the title compound. LCMS (Method B): m/z=201.2, 203.2 [M+H]$^+$.

The following intermediate was prepared using methods analogous to the one described above.

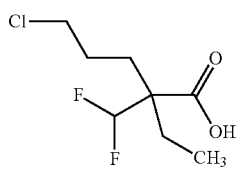

Intermediate 6

5-chloro-2-(difluoromethyl)-2-methyl-pentanoyl chloride

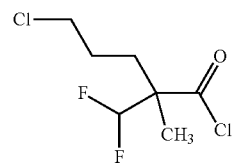

5-Chloro-2-(difluoromethyl)-2-methyl-pentanoic acid (150 mg) was dissolved in thionyl chloride (10 ml). The mixture was stirred at 68° C. for 2 h. The reaction mixture was concentrated to yield the title compound. $^1$H-NMR (400 MHz, CDCl$_3$): δ 6.11 (t, J=55.6 Hz, 1H), 3.60-3.56 (m, 2H), 2.07 (m, 1H), 1.94-1.82 (m, 3H), 1.43 (t, J=1.1 Hz, 3H).

The following intermediate was prepared using methods analogous to the one described above.

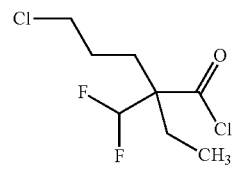

Intermediate 7 tert-butyl 1-(3-chloropropyl)cyclopropanecarboxylate

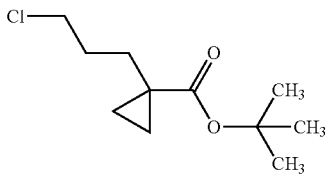

To a solution of tert-butyl cyclopropanecarboxylate (5 g, 35.16 mmol) in dry THF (30 mL) was added LDA (2 M, 21.10 mL) dropwise at −70° C. under N$_2$. The reaction mixture was stirred for 2 h at −35° C. before adding a solution of 1-bromo-3-chloro-propane (8.30 g, 52.74 mmol, 5.19 mL) in THF (10 mL). The resulting mixture was stirred at 25° C. for 12 h. The reaction was quenched with sat. NH$_4$Cl solution (50 mL) at 25° C. and extracted with EtOAc (3×20 mL). The combined organic layers were washed with brine (40 mL), dried over Na$_2$SO$_4$, filtered and concentrated under reduced pressure to provide the title compound.

Intermediate 8

1-(3-chloropropyl)cyclopropanecarbonyl chloride

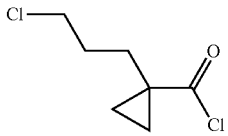

To a solution of tert-butyl 1-(3-chloropropyl)cyclopropanecarboxylate (5 g, 22.86 mmol) in DCM (40 mL) was added TFA (15.40 g, 135.06 mmol, 10 mL) at 0° C. under N$_2$. The reaction solution was stirred at 25° C. for 12 h before quenching with sat. NaHCO$_3$ solution (30 mL) at 25° C. The mixture was extracted with DCM (3×20 mL) and the combined organic layers were washed with brine (50 mL), dried over Na$_2$SO$_4$, filtered and concentrated under reduced pressure to provide the carboxylic acid (2.4 g, 65%) as a brown oil. To a solution of the acid (300 mg, 1.84 mmol) and DMF (26.97 mg, 0.37 mmol) in DCM (6 mL) was added (COCl)$_2$ (280.99 mg, 2.21 mmol) at 0° C. over a period of 10 min under N$_2$. The reaction mixture was warmed to 25° C. over a period of 20 min and stirred at 25° C. for 1 hr. The reaction mixture was concentrated under reduced pressure to provide the title compound.

Preparation 1

(E)-3-(5-fluoro-3-pyridyl)prop-2-enal

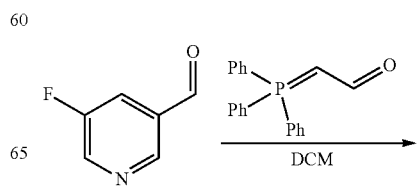

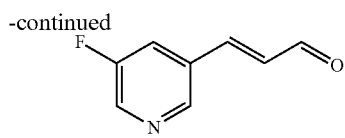

A solution of 5-fluoropyridine-3-carbaldehyde (10 g, 79.94 mmol) and (triphenylphosphoranylidene)acetaldehyde (24.33 g, 79.94 mmol) in DCM (200 mL) was stirred at rt overnight. The reaction mixture was treated with silica, evaporated under reduced pressure and purified by column chromatography eluting with a gradient of ethyl acetate (0 to 100%) in hexanes to provide the title compound. $^1$H-NMR (400 MHz, CDCl$_3$): δ 9.78 (d, J=7.4 Hz, 1H), 8.64 (t, J=1.6 Hz, 1H), 8.56 (d, J=2.7 Hz, 1H), 7.62 (dddd, J=8.9, 2.7, 1.8, 0.5 Hz, 1H), 7.54-7.49 (m, 1H), 6.79 (dd, J=16.1, 7.4 Hz, 1H).

The following intermediates were prepared using methods analogous to the one described above.

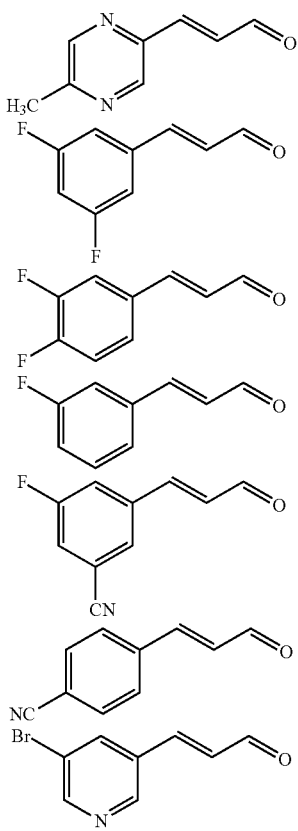

Preparation 2

2-(4,5-dihydro-1H-pyrazol-5-yl)-5-methyl-pyrazine

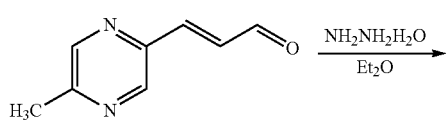

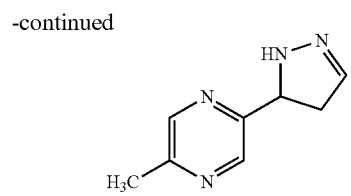

Hydrazine hydrate (1.94 mL, 39.62 mmol) was added to 25 mL of diethyl ether in a 100 mL round bottomed flask. To the vigorously stirred suspension (stir rate 1200 rpm) was added a solution of (E)-3-(5-methylpyrazin-2-yl)prop-2-enal (0.59 g, 3.96 mmol) in diethyl ether (25 mL) over 30 min at rt. The reaction mixture was stirred at rt for another 10 min after the completion of the addition followed by the addition of 200 mL of 5% aqueous sodium bicarbonate solution. The mixture was extracted with ethyl acetate (3×150 mL). The combined organic layers were washed with brine (200 mL) dried over MgSO$_4$ and then concentrated to yield the title compound, which was used in the next step without purification. LCMS (Method B): m/z=163.04 [M+H]$^+$.

The following intermediates were prepared using methods analogous to the one described above.

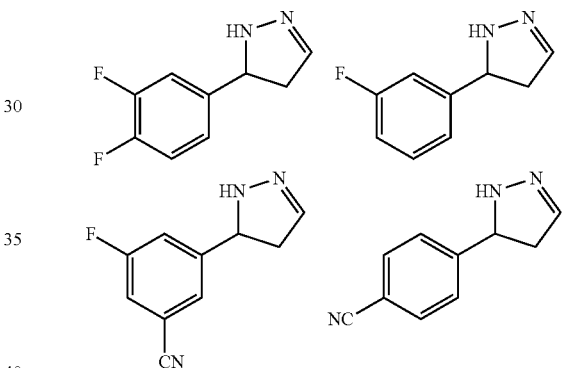

Preparation 3 di-tert-butyl 3-(5-fluoro-3-pyridyl)-5-hydroxy-pyrazolidine-1,2-dicarboxylate

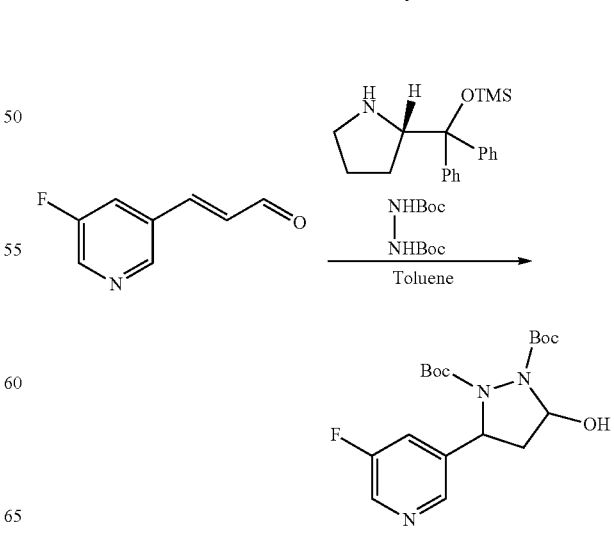

To a solution of (E)-3-(5-fluoro-3-pyridyl)prop-2-enal (5.9 g, 39.04 mmol) in toluene (50 mL) was added (S)-(−)-α,α-Diphenyl-2-pyrrolidinemethanol trimethylsilyl ether (2.92 g, 8.98 mmol) followed by tert-butyl N-(tert-butoxycarbonylamino)carbamate (13.6 g, 58.56 mmol). Toluene (23 mL) was used to wash the reactants off the reaction flask wall and added to the reaction mixture. The reaction vessel was sealed and stirred at rt overnight. The reaction mixture was loaded directly onto silica gel and purified by flash chromatography (0-100% ethyl acetate in hexanes) to yield the title compound. LCMS (Method B): m/z=384.3 [M+H]$^+$.

The following intermediates were prepared using methods analogous to the one described above.

Preparation 4

3-(4,5-dihydro-1H-pyrazol-5-yl)-5-fluoro-pyridine

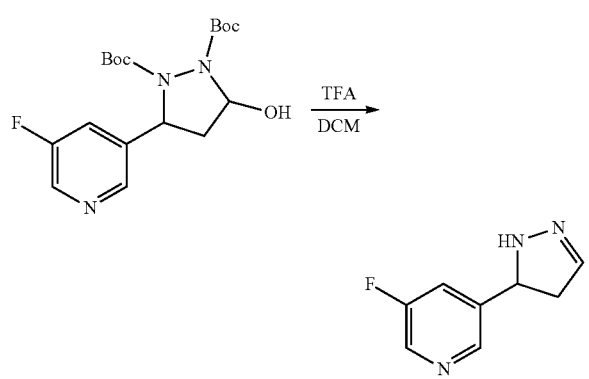

To a solution of di-tert-butyl 3-(5-fluoro-3-pyridyl)-5-hydroxy-pyrazolidine-1,2-dicarboxylate (2.0 g, 5.22 mmol) in DCM (20 mL) was added 2,2,2-trifluoroacetic acid (20 mL). The reaction mixture was stirred at rt for 1 h and was then concentrated under reduced pressure. The resulting residue was dissolved in ethyl acetate (50 mL) and washed with 5% NaHCO$_3$ (20 mL), water (20 mL) and brine (20 mL). The organic layer was collected and dried over MgSO$_4$ before concentrating under reduced pressure to yield the title compound, which was used in the next step without purification. LCMS (Method B): m/z=166.1 [M+H]$^+$.

The following intermediates were prepared using methods analogous to the one described above.

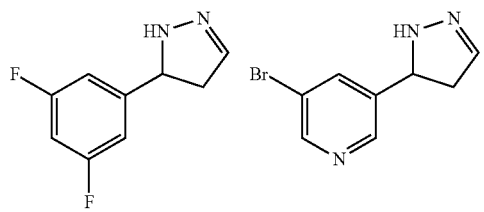

Preparation 5

5-chloro-2,2-dimethyl-1-[3-(5-methylpyrazin-2-yl)-3,4-dihydropyrazol-2-yl]pentan-1-one

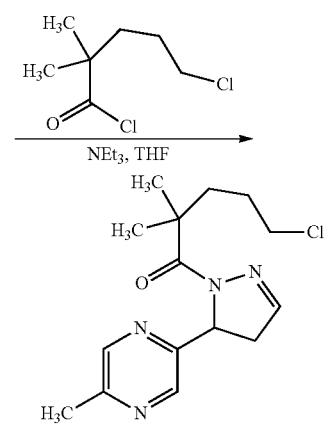

A solution of 5-chloro-2,2-dimethyl-pentanoyl chloride (364 mg, 1.99 mmol) in THF (10 mL) was added to 2-(4,5-dihydro-1H-pyrazol-5-yl)-5-methyl-pyrazine (0.22 g, 1.33 mmol) and triethylamine (0.55 mL, 3.98 mmol). The reaction mixture was stirred at rt for 16 h before diluting with sat aq. sodium bicarbonate (30 mL) and EtOAc (30 mL). The organic phase was washed with water and saturated brine solution (30 mL). The organics were dried (MgSO$_4$) before concentration to dryness. The crude was then purified by flash column chromatography eluting with a gradient of EtOAc (0% to 100%) in hexanes to provide the title compound. LCMS (Method B): m/z=309.15, 311.04 [M+H]$^+$.

The following intermediates were prepared using methods analogous to the one described above.

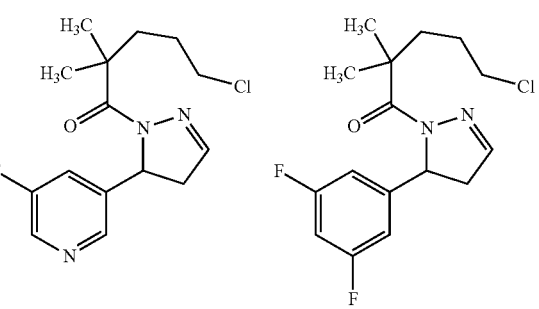

-continued

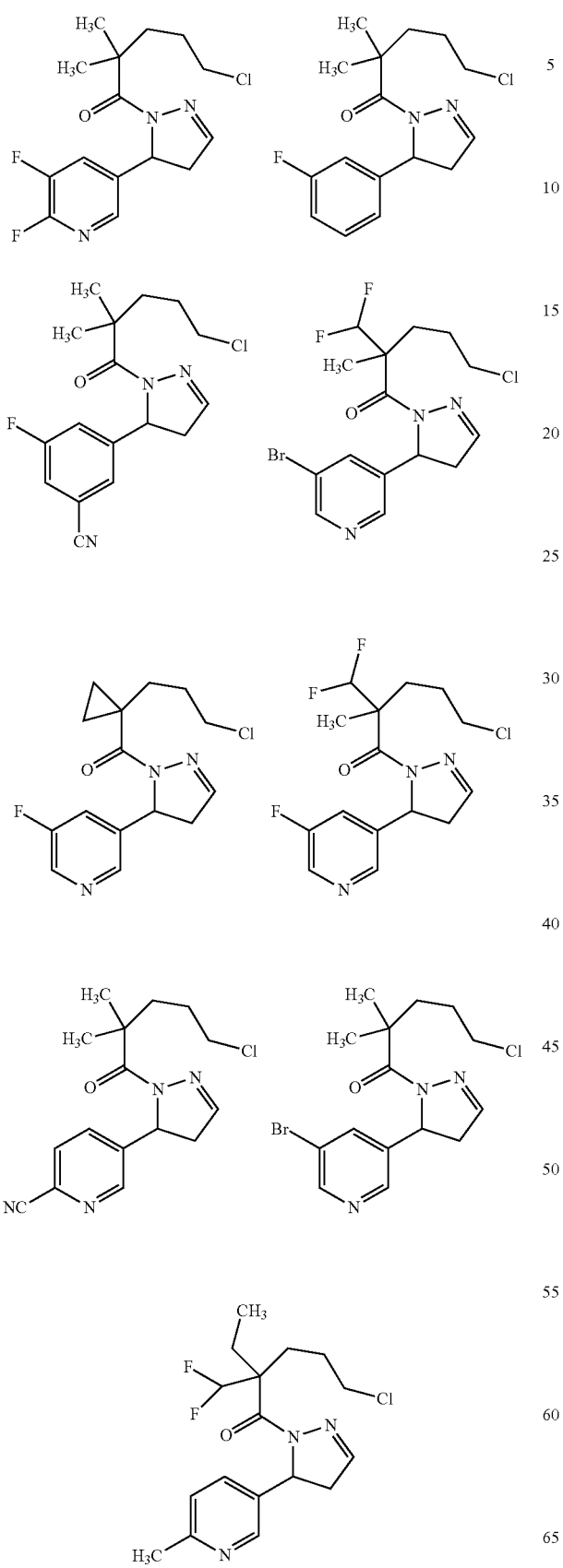

Preparation 6

3-(5-fluoro-3-pyridyl)-6,6-dimethyl-3,7,8,9-tetrahydropyrazolo[1,2-a]diazepin-5-one

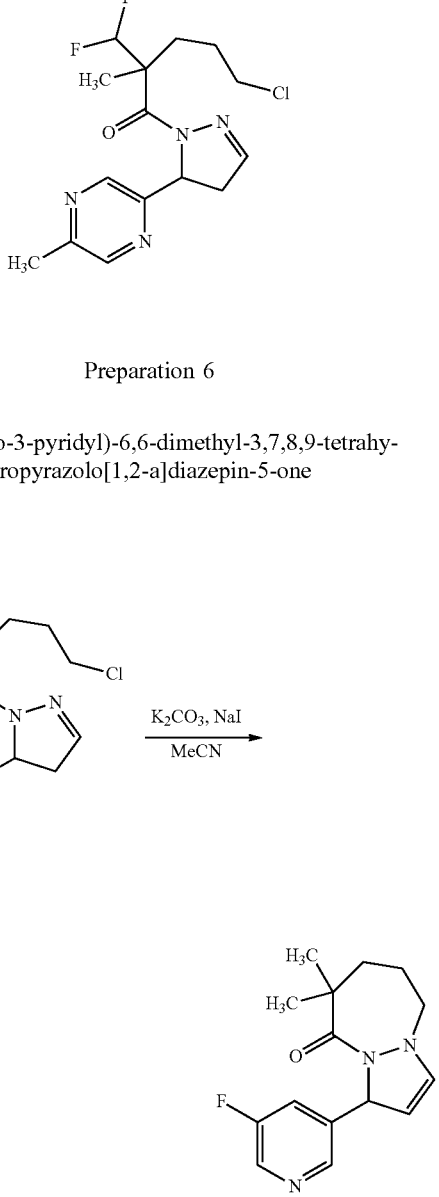

To a microwave vial loaded with sodium iodide (67.8 mg, 0.45 mmol) and potassium carbonate (93.0 mg, 0.67 mmol) was added a solution of 5-chloro-1-[3-(5-fluoro-3-pyridyl)-3,4-dihydropyrazol-2-yl]-2,2-dimethyl-pentan-1-one (70 mg, 0.22 mmol) in MeCN (10 mL). The vial was sealed and heated at 120° C. for 20 min in a microwave reactor. The starting material shows conversion to the corresponding iodo intermediate (LCMS (Method B): m/z=404.59 [M+H]$^+$). The reaction mixture was then heated at 150° C. for 110 min in the microwave reactor. The reaction mixture was cooled to rt, diluted with 50 mL of ethyl acetate and washed with water (50 mL) and brine (50 mL). The organic phase was dried over MgSO$_4$ and concentrated to yield the title compound, which was used in the next step without purification. LCMS (Method B): m/z=276.53 [M+H]$^+$.

The following intermediates were prepared using methods analogous to the one described above.

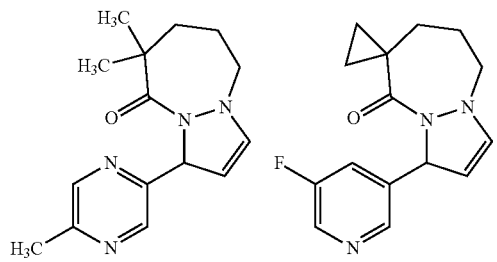

Preparation 7

5-chloro-1-[5-(3,5-difluorophenyl)pyrazolidin-1-yl]
2,2-dimethyl-pentan-1-one

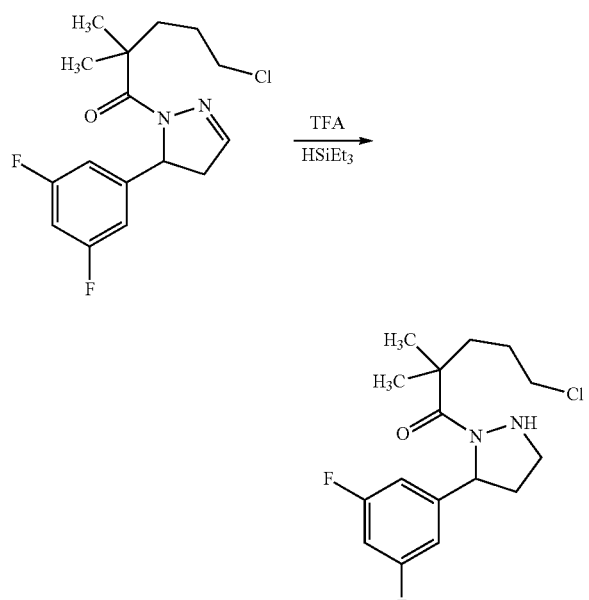

To a solution of 5-chloro-1-[3-(3,5-difluorophenyl)-3,4-dihydropyrazol-2-yl]2,2-dimethyl-pentan-1-one (100 mg, 0.30 mmol) in 2,2,2-trifluoroacetic acid (5.0 mL, 30.4 mmol) was added triethylsilane (0.24 mL, 1.52 mmol) and the resulting reaction mixture was stirred overnight at rt. The reaction mixture was concentrated to dryness and the resulting residue was dissolved in EtOAc (30 mL), washed with 5% NaOH solution (20 mL), water (20 mL) and brine (20 mL). The organic layer was dried over anhydrous MgSO₄, filtered and concentrated under reduced pressure to provide the crude product, which was purified by silica gel column chromatography (0-10% MeOH/DCM) to yield the title compound.

The following intermediates were prepared using methods analogous to the one described above.

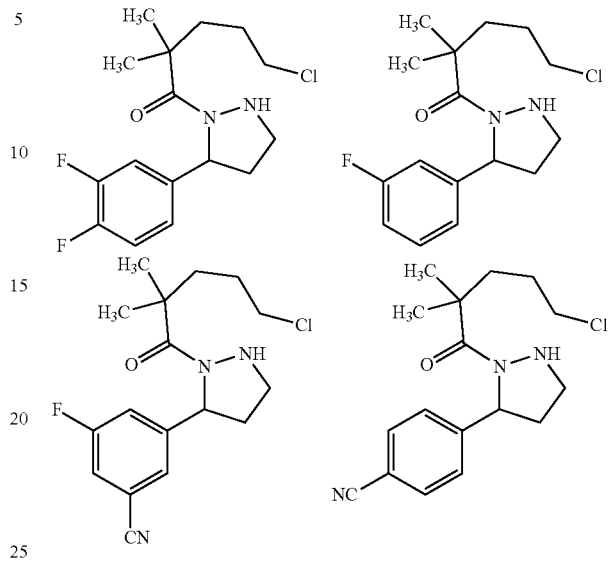

Preparation 8

1-(5-(5-bromo-3-pyridyl)pyrazolidin-1-yl-5-chloro-2,2-dimethyl-pentan-1-one

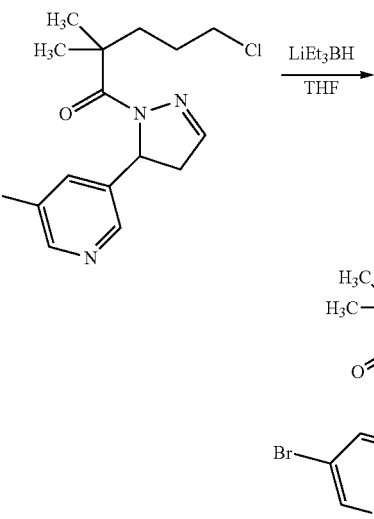

To a solution of 1-(3-(5-bromo-3-pyridyl)-3,4-dihydropyrazol-2-yl-5-chloro-2,2-dimethyl-pentan-1-one (150 mg, 0.40 mmol) in THF (5.0 mL) was added lithium triethylborohydride (0.50 mL, 1.7 M, 0.85 mmol) and the resulting reaction mixture was stirred for 5 min at −78° C. The reaction mixture was quenched by adding saturated sodium bicarbonate solution (5 mL) at −78° C. and the mixture was concentrated to dryness. The resulting residue was dissolved in EtOAc (30 mL), washed with 5% NaOH solution (20 mL), water (20 mL) and brine (20 mL). The organic layer was dried over anhydrous MgSO₄, filtered and concentrated under reduced pressure to provide the crude product which was purified by silica gel column chromatography (0-10% MeOH/DCM) to yield the title compound.

The following intermediate was prepared using methods analogous to the one described above.

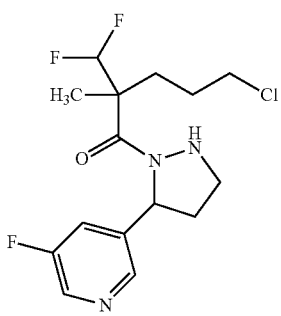

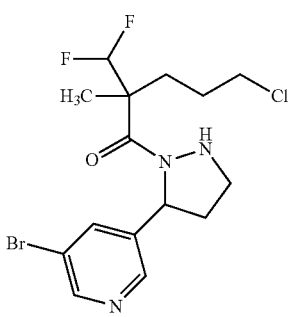

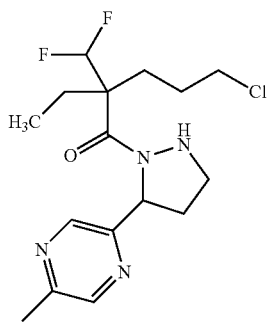

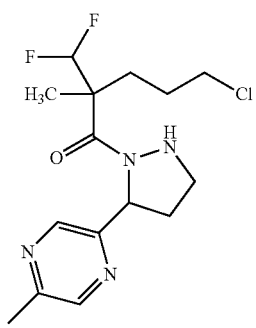

Preparation 9 tert-Butyl (3S)-3-(4-fluorophenyl)-5-hydroxypyrazolidine-1-carboxylate

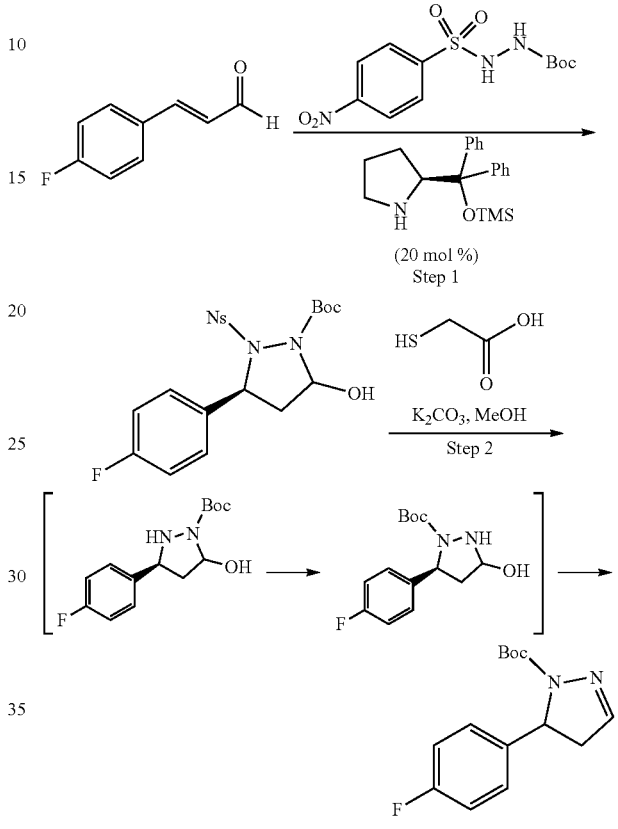

Step 1: To a solution of 4-fluorocinnamaldehyde (5 g, 0.03 mol, 1 equiv) in toluene (35 mL, 7 vol) was added tert-butyl 2-((4-fluorophenyl)sulfonyl)hydrazine-1-carboxylate (12.6 g, 0.039 mol, 1.2 equiv) and (S)-(−)-α,α-diphenyl-2-pyrrolidinemethanol trimethylsilyl ether (2.16 g, 0.006 mol, 0.2 equiv) at 0° C. The reaction mixture was stirred at room temperature for 5 days. Reaction progress was monitored by TLC. After the completion of the reaction, toluene was removed under vacuum. The crude product was purified by column chromatography (230-400 size mesh) eluting with 15 to 18% EtOAc in pet ether to afford tert-butyl (3S)-3-(4-fluorophenyl)-5-hydroxy-2-((4-nitrophenyl)sulfonyl)pyrazolidine-1-carboxylate.

Step 2: To a solution of tert-butyl-(3S)-3-(4-fluorophenyl)-5-hydroxy-2-((4-nitrophenyl)sulfonyl)pyrazolidine-1-carboxylate (4.5 g, 0.009 mol, 1 equiv) in methanol (135 mL, 30 vol) was added $K_2CO_3$ (6.62 g, 0.039 mol, 5 equiv) and thioglycolic acid (1.67 mL, 0.02 mol, 2.5 equiv) at 0° C. under inert atmosphere. The reaction mixture was stirred at room temperature over a period of 20 h. The progress of the reaction progress was monitored by TLC. After the completion of the reaction, methanol was removed under vacuum. The residue was suspended in water (100 mL) and then extracted with EtOAc (3×70 mL). The combined organic layer was washed with saturated brine solution and dried over Na₂SO₄. The solvent was concentrated under vacuum. The crude product was purified by column chromatography (230-400 size mesh) eluting with 16 to 20% EtOAc in pet ether to afford tert-butyl 5-(4-fluorophenyl)-4,5-dihydro-1H-pyrazole-1-carboxylate. Note: The compound was epimerized during nosyl deprotection. ¹H NMR (DMSO, 400 MHz: 7.18 (m, 4H), 7.06 (s, 1H), 5.14 (dd, J 12, 5.6 Hz, 1H), 3.44 (dd, J 18.8, 12.0 Hz, 1H), 2.68 (m, 1H), 1.25 (s, 9H).

Example 1

Procedure A 3-(5-fluoro-3-pyridyl)-6,6-dimethyl-1,2,3,7,8,9-hexahydropyrazolo[1,2-a]diazepin-5-one

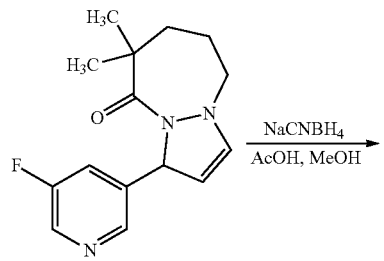

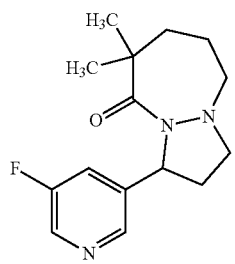

3-(5-Fluoro-3-pyridyl)-6,6-dimethyl-3,7,8,9-tetrahydropyrazolo[1,2-a]diazepin-5-one (50 mg, 0.18 mmol) was dissolved in methanol (4 mL) at rt. Sodium cyanoborohydride (114 mg, 1.82 mmol) and acetic acid (0.1 mL, 1.82 mmol) were then added. The reaction mixture was stirred overnight at 50° C. The solvent was evaporated and the reaction mixture was diluted with DCM. The organic phase was washed with sat. aq. NaHCO₃. The organic phase was separated, dried over sodium sulfate, filtered and evaporated under reduced pressure. The crude material was purified by preparative HPLC to provide the title compound as a mixture of enantiomers. ¹H-NMR (400 MHz, CDCl₃): δ 8.40-8.37 (m, 2H), 7.34-7.32 (m, 1H), 5.27-5.24 (m, 1H), 3.31-3.25 (m, 2H), 2.96-2.92 (m, 2H), 2.61-2.56 (m, 1H), 2.02-1.97 (m, 1H), 1.97-1.79 (m, 2H), 1.67-1.63 (m, 2H), 1.37-1.25 (m, 6H). LCMS (Method B): m/z=278.38 [M+H]⁺.

Example 2

6,6-dimethyl-3-(5-methylpyrazin-2-yl)-1,2,3,7,8,9-hexahydropyrazolo[1,2-a]diazepin-5-one

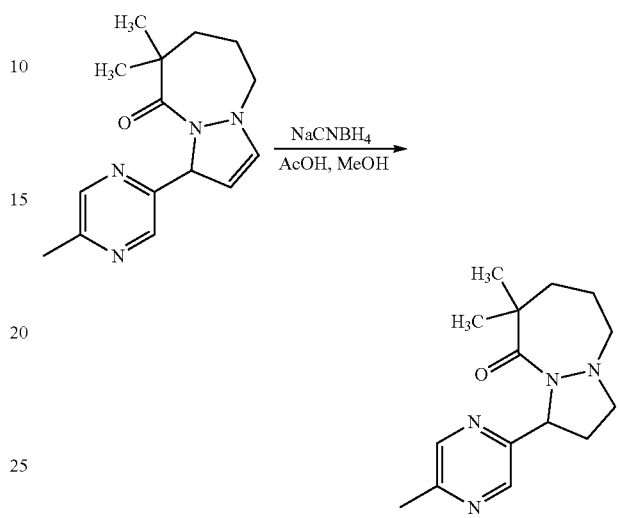

The title compound was prepared according to Procedure A and purified by preparative HPLC to provide the desired product as a mixture of enantiomers isolated as an off-white sticky solid. Further purification by SFC with the following conditions: Column: Chiralpak AD-H 250×30 mm i.d. 5 µm; mobile phase A: CO₂, mobile phase B: MeOH (0.1% NH₃H₂O); gradient: B %=25%; flow rate: 60 g/min; wavelength: 220 nm; column temperature: 40° C.; system back pressure: 100 bar to provide the title compound as the second eluting enantiomer. ¹H NMR (400 MHz, CDCl₃) δ 8.49 (br s, 1H), 8.35 (s, 1H), 5.21 (br t, J=6.8 Hz, 1H), 3.38-3.02 (m, 3H), 2.90-2.79 (m, 1H), 2.53 (s, 3H), 2.49-2.21 (m, 2H), 1.98-1.83 (m, 1H), 1.74-1.63 (m, 1H), 1.60-1.53 (m, 2H), 1.40-1.14 (m, 6H). LCMS (Method E): m/z=275.4 [M+H]⁺, 1.419 min.

Example 3

Procedure B 3-(3,5-difluorophenyl)-6,6-dimethyl-1,2,3,7,8,9-hexahydropyrazolo[1,2-a]diazepin-5-one

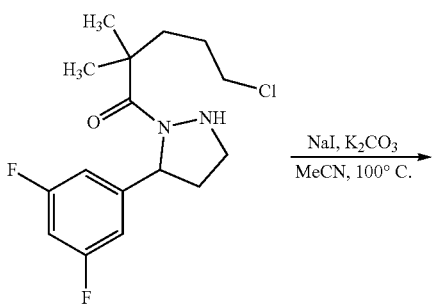

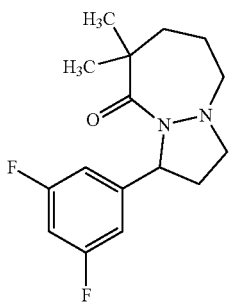

5-Chloro-1-[5-(3,5-difluorophenyl)pyrazolidin-1-yl]-2,2-dimethyl-pentan-1-one (50.8 mg, 0.15 mmol) was dissolved in MeCN (5.0 mL) and NaI (46.3 mg, 0.31 mmol) and K₂CO₃ (63.5 mg, 0.46 mmol) were added and the mixture was sealed and heated at 100° C. for 2 h in a microwave. The reaction mixture was cooled to rt, diluted with 50 mL of EtOAc, washed with water (3×50 mL), brine (50 mL), dried over MgSO₄ and concentrated in vacuo. The crude reaction mixture was purified employing silica gel flash chromatography (0-80% EtOAc/hexanes) to provide the racemate as a clear oil. The enantiomers were resolved by chiral HPLC on a Chiralpak IA (25×2.0 cm), 5 μm column using a mobile phase of n-hexane/ethanol 90/10% v/v and a flow rate of 17 mL/min to afford the title compound as the second eluting enantiomer. ¹H NMR (400 MHz, Acetone-d₆) δ 6.95-6.79 (m, 3H), 5.18 (dd, J=8.0, 5.0 Hz, 1H), 3.38-3.18 (m, 2H), 2.98 (t, J=5.8 Hz, 2H), 2.66-2.51 (m, 1H), 2.07-1.80 (m, 3H), 1.71-1.56 (m, 2H), 1.34-1.21 (m, 6H). LCMS (Method A): m/z=295.5 [M+H]⁺. E.e.=98.6% as determined on a Chiralpak IA (25×0.46 cm), 5 μm column using a mobile phase of n-hexane/ethanol 90/10% v/v, flow rate: 1.0 mL/min, retention time: 7.5 min.

Example 4

3-(3,4-difluorophenyl)-6,6-dimethyl-1,2,3,7,8,9-hexahydropyrazolo[1,2-a]diazepin-5-one

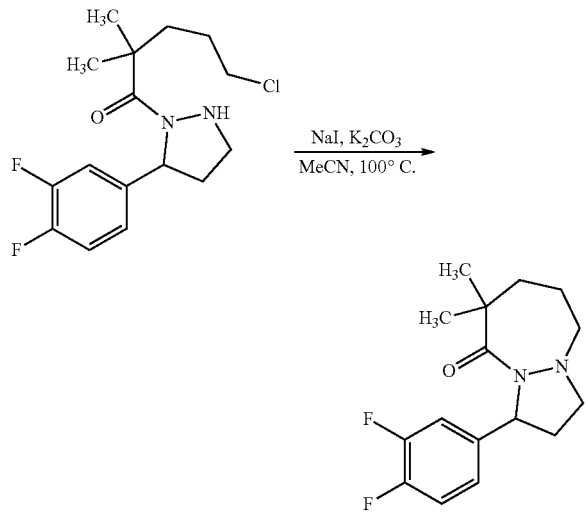

The title compound was prepared according to Procedure B and purified by column chromatography (0-80% ethyl acetate in hexanes) to yield racemic 3-(3,4-difluorophenyl)-6,6-dimethyl-1,2,3,7,8,9-hexahydropyrazolo[1,2-a]diazepin-5-one. The racemate was resolved by chiral HPLC on a Chiralpak IA (25×2.0 cm), 5 μm column using a mobile phase of n-hexane/ethanol 90/10% v/v and a flow rate of 17 mL/min to afford the title compound as the second eluting enantiomer. ¹H NMR (400 MHz, CDCl₃) δ 7.19-6.92 (m, 3H), 5.18 (dd, J=8.2, 4.4 Hz, 1H), 3.23 (br. S., 2H), 3.01-2.84 (m, 2H), 2.57-2.41 (m, 1H), 2.10-1.80 (m, 3H), 1.71-1.59 (m, 2H), 1.41-1.27 (m, 6H). LCMS (Method C): m/z=295.2 [M+H]⁺. E.e.=99.6% as determined on a Chiralpak IA (25×0.46 cm), 5 μm column using a mobile phase of n-hexane/ethanol 90/10% v/v, flow rate: 1.0 mL/min, retention time: 8.6 min.

Example 5

3-(3-fluorophenyl)-6,6-dimethyl-1,2,3,7,8,9-hexahydropyrazolo[1,2-a]diazepin-5-one

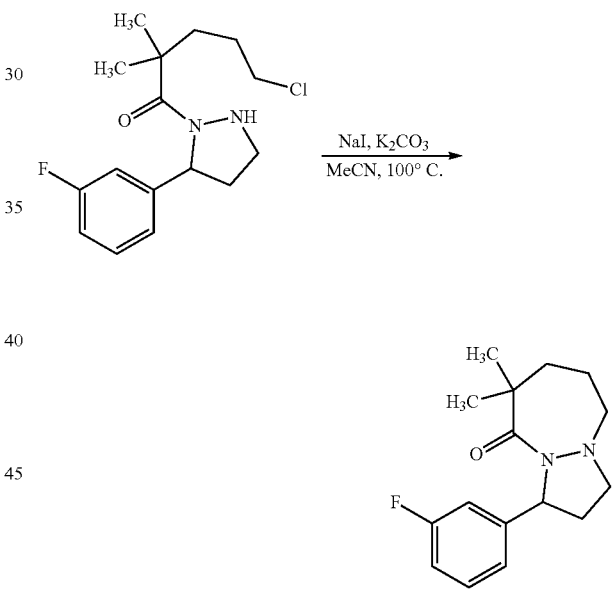

The title compound was prepared according to Procedure B and purified by flash chromatography (0-80% ethyl acetate in hexanes) to yield the racemate. The racemic mixture was resolved by chiral HPLC on a Chiralpak AD-H (25×2.0 cm), 5 μm column using a mobile phase of n-hexane/2-propanol 90/10% v/v and a flow rate of 17 mL/min to afford the title compound as the second eluting enantiomer. ¹H NMR (400 MHz, CDCl₃) δ 7.34-7.23 (m, 1H), 7.04 (d, J=7.8 Hz, 1H), 6.98-6.85 (m, 2H), 5.24 (dd, J=8.2, 4.4 Hz, 1H), 3.23 (br. s., 2H), 2.93 (t, J=5.9 Hz, 2H), 2.58-2.42 (m, 1H), 2.05-1.80 (m, 3H), 1.74-1.59 (m, 2H), 1.46-1.25 (m, 6H). LCMS (Method A): m/z=277.3 [M+H]⁺. E.e.>99% as determined on a Chiralpak IA (25×0.46 cm), 5 μm column using a mobile phase of n-hexane/2-propanol 90/10% v/v, flow rate: 1.0 mL/min, retention time: 8.4 min.

Example 6

3-(6,6-dimethyl-5-oxo-1,2,3,7,8,9-hexahydropyrazolo[1,2-a]diazepin-3-yl)-5-fluoro-benzonitrile

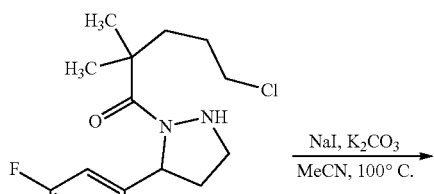

The title compound was prepared according to Procedure B and purified by flash chromatography (0-80% ethyl acetate in hexanes) to yield the title compound. ¹H-NMR (400 MHz, CDCl₃): δ 7.40-7.30 (m, 1H), 7.16-7.10 (m, 2H), 5.30-5.20 (m, 1H), 3.35-3.20 (m, 2H), 3.00-2.90 (m, 2H), 2.62-2.50 (m, 1H), 2.00-1.85 (m, 3H), 1.70-1.64 (m, 2H), 1.40-1.28 (m, 6H). LCMS (Method B): m/z=302.1 [M+H]⁺.

Example 7

4-(6,6-dimethyl-5-oxo-1,2,3,7,8,9-hexahydropyrazolo[1,2-a]diazepin-3-yl)benzonitrile The title compound was prepared according to Procedure B and purified by flash chromatography (0-80% ethyl acetate in hexanes) to yield the title compound. ¹H-NMR (400 MHz, CDCl₃): δ 7.67-7.60 (m, 2H), 7.35 (d, J=8.0 Hz, 2H), 5.30-5.20 (m, 1H), 3.35-3.20 (m, 2H), 3.00-2.90 (m, 2H), 2.62-2.50 (m, 1H), 2.00-1.85 (m, 3H), 1.70-1.64 (m, 2H), 1.40-1.28 (m, 6H). LCMS (Method B): m/z=284.1 [M+H]⁺.

Example 8

(7S,9aR)-4-ethyl-7-(3-fluorophenyl)-4-methyl-1,3,7,8,9,9a-hexahydropyrrolo[2,1-c][1,4]oxazepin-5-one

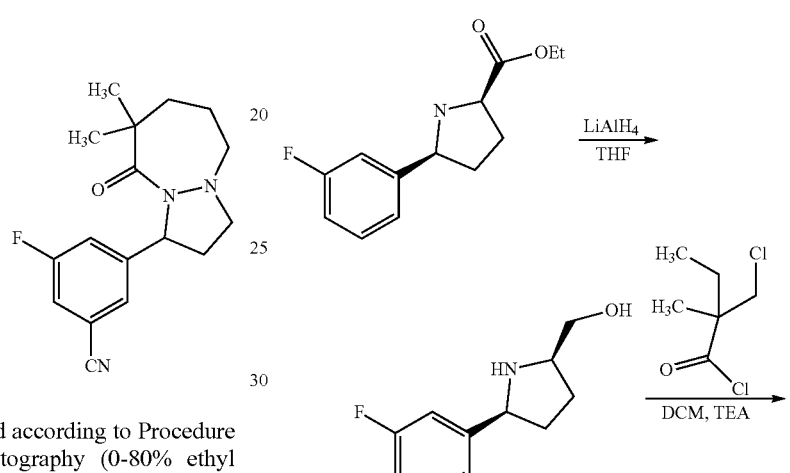

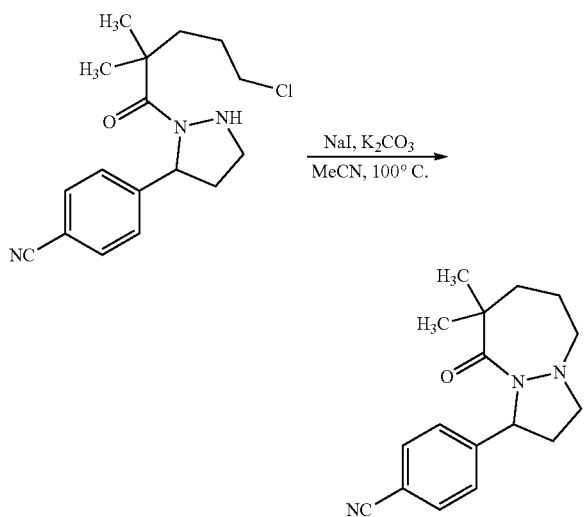

Methyl 2-(chloromethyl)-2-methylbutanoate was prepared following the conditions described by Zhang-Jie Shi et al (Org. Lett., 2016, 18 (9), pp 2040-2043). To a stirred solution of diisopropylamine (1.68 mL, 12 mmol) in THF (15 mL) was added n-butyllithium (2.5 M solution in hexanes, 4.8 mL, 12 mmol) dropwise at −78° C. The mixture was stirred at 0° C. for 30 min, then cooled again to −78° C. A solution of methyl 2-methylbutyrate (1.32 mL, 10 mmol) in THF (5 mL) was added dropwise at −78° C. and the mixture was stirred at this temperature for 1 h. A solution of chloroiodomethane (0.73 mL, 10 mmol) in THF (10 mL) was added dropwise at −78° C. The resulting mixture was stirred overnight allowing the temperature to reach room temperature. The mixture was quenched with water at 0° C. and extracted with Et$_2$O (3×25 mL). The combined organic layers were washed with brine, dried over Na$_2$SO$_4$, and evaporated under reduced pressure to afford the title compound. This material was used in the following step without further purification. $^1$H NMR (400 MHz, CDCl$_3$) δ 3.78-3.73 (m, 4H), 3.57 (d, J=10.8 Hz, 1H), 1.82-1.55 (m, 3H), 1.29 (s, 3H), 0.88 (t, J=7.5 Hz, 3H).

2-(Chloromethyl)-2-methylbutanoic acid was prepared following the conditions described by Zhang-Jie Shi et al (Org. Lett., 2016, 18 (9), pp 2040-2043). Concentrated HCl (15 mL) was carefully added at 0° C. to methyl 2-(chloromethyl)-2-methylbutanoate (1.15 g, 7.0 mmol). The resulting mixture was stirred at 80° C. for 7 h, then left overnight at room temperature. At this point an NMR of a reaction aliquot quenched with water and extracted with CH$_2$Cl$_2$ indicated that a significant amount of starting material remained. The mixture was then heated to 100° C. A check by NMR after 5 h showed almost complete conversion to the title compound. Water was added to the hot mixture and this was extracted twice with CH$_2$Cl$_2$. The combined organic phases were washed twice with water, dried over Na$_2$SO$_4$, filtered and evaporated under reduced pressure to afford a 1.75:1 mixture of the title compound and methyl 2-(chloromethyl)-2-methylbutanoate. This mixture was used in the following step without further purification. $^1$H NMR (400 MHz, CDCl$_3$) only signals from title compound reported δ 3.76 (d, J=11.0 Hz, 1H), 3.60 (d, J=11.0 Hz, 1H), 1.86-1.57 (m, 2H), 1.32 (s, 3H), 0.95 (t, J=7.5 Hz, 3H). LCMS (Method A): m/z=149.0 [M−H]$^−$, 0.81 min.

(2R,5S)-5-(3-fluorophenyl)pyrrolidin-2-yl]methanol: A solution of ethyl (2R,5S)-5-(3-fluorophenyl)pyrrolidine-2-carboxylate (1.36 g, 5.72 mmol) in THF (25 mL) was added dropwise to a suspension of lithium aluminum hydride (260.35 mg, 6.86 mmol) in THF at 0° C. The reaction mixture was stirred at 0° C. for 1 h and left to warm up to rt for 2 h. The reaction mixture was carefully quenched with aq. 1 M NaOH at 0° C. The reaction mixture was diluted with ethyl acetate (50 mL) and the organic phase was separated and dried (MgSO$_4$) before concentration to dryness to provide the title compound. $^1$H-NMR (400 MHz, CDCl$_3$): δ 7.31-7.26 (m, 1H), 7.18-7.13 (m, 2H), 6.96-6.91 (m, 1H), 4.31 (dd, J=9.1, 6.7 Hz, 1H), 3.66 (dd, J=10.3, 3.8 Hz, 1H), 3.56-3.50 (m, 1H), 3.45 (t, J=5.2 Hz, 1H), 2.24-2.10 (m, 1H), 2.03-1.93 (m, 1H), 1.81-1.73 (m, 1H), 1.66 (dq, J=12.1, 9.0 Hz, 1H).

2-(Chloromethyl)-1-[(2S,5R)-2-(3-fluorophenyl)-5-(hydroxymethyl)pyrrolidin-1-yl]-2-methyl-butan-1-one: 2-(chloromethyl)-2-methyl-butanoyl chloride (123.82 mg, 0.73 mmol) was added to a solution of [(2R,5S)-5-(3-fluorophenyl)pyrrolidin-2-yl]methanol (171.59 mg, 0.88 mmol) and triethylamine (0.31 mL, 2.2 mmol) in DCM (5 mL) at 0° C. The reaction mixture was left to warm up to rt overnight. The reaction mixture was then treated with aq. sat sodium bicarbonate and diluted with DCM. The organic phase was separated, dried over MgSO$_4$, filtered and evaporated under reduced pressure to provide the title compound. LCMS (Method B): m/z=328.14, 329.99 [M+H]$^+$.

(7S,9aR)-4-ethyl-7-(3-fluorophenyl)-4-methyl-1,3,7,8,9,9a-hexahydropyrrolo[2,1-c][1,4]oxazepin-5-one: A solution of 2-(chloromethyl)-1-[(2S,5R)-2-(3-fluorophenyl)-5-(hydroxymethyl)pyrrolidin-1-yl]-2-methyl-butan-1-one (210 mg, 0.64 mmol) in DMF (5 mL) was added to sodium hydride (128.11 mg, 3.2 mmol) at 0° C. The reaction mixture was warmed to rt overnight. The reaction mixture was then treated with water (10 mL) and diluted with EtOAc (10 mL). The organics were separated and dried (MgSO$_4$) before concentration to dryness. The crude material was purified by preparative HPLC using method D to provide the title compound as the second eluting isomer (retention time 11.24 min). $^1$H-NMR (400 MHz, CDCl$_3$): δ 7.31-7.25 (m, 1H), 7.02-6.99 (m, 1H), 6.94-6.89 (m, 2H), 5.41 (d, J=8.8 Hz, 1H), 4.21-4.14 (m, 2H), 3.81-3.73 (m, 2H), 3.48 (dd, J=12.8, 10.1 Hz, 1H), 2.24 (dddd, J=13.3, 12.6, 8.9, 6.5 Hz, 1H), 2.01-1.91 (m, 2H), 1.88-1.83 (m, 1H), 1.67-1.57 (m, 1H), 1.40 (dq, J=14.1, 7.2 Hz, 1H), 1.32-1.25 (m, 3H), 0.87-0.80 (m, 3H). LCMS (Method B): m/z=292.29 [M+H]$^+$.

(7S,9aS)-4-ethyl-7-(3-fluorophenyl)-4-methyl-1,3,7,8,9,9a-hexahydropyrrolo[2,1-c][1,4]oxazepin-5-one could be prepared employing similar procedures using (2S,5S)-5-(3-fluorophenyl)pyrrolidine-2-carboxylate, which can be prepared by epimerization of (2R,5S)-5-(3-fluorophenyl)pyrrolidine-2-carboxylate.

Example 9

5-(6,6-dimethyl-5-oxo-1,2,3,7,8,9-hexahydropyrazolo[1,2-a]diazepin-3-yl)pyridine-3-carbonitrile

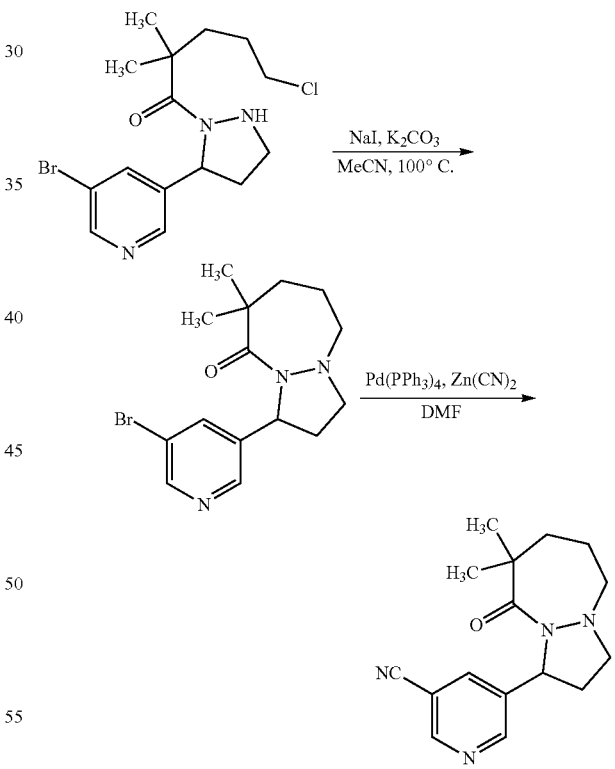

3-(5-Bromo-3-pyridyl)-6,6-dimethyl-1,2,3,7,8,9-hexahydropyrazolo[1,2-a]diazepin-5-one: The title compound was prepared according to Procedure B and purified by column chromatography (0-80% ethyl acetate in hexanes) to provide the desired product. LCMS (Method B): m/z=338.3, 340.3 [M+H]$^+$.

5-(6,6-Dimethyl-5-oxo-1,2,3,7,8,9-hexahydropyrazolo[1,2-a]diazepin-3-yl)pyridine-3-carbonitrile: To a solution of 3-(5-bromo-3-pyridyl)-6,6-dimethyl-1,2,3,7,8,9-hexahydropyrazolo[1,2-a]diazepin-5-one (40 mg, 0.12 mmol) in DMF (2.0 mL) was added tetrakis(triphenylphosphine)palladium (0) (0.41 mg, 0.036 mmol) and zinc cyanide (13.9 mg, 0.12 mmol). The resulting reaction mixture was stirred for 2 h at 100° C. The reaction mixture was quenched by adding saturated sodium bicarbonate solution (5 mL) at −78° C. The mixture was diluted with EtOAc (30 mL), washed with 5% NaOH solution (20 mL), DI water (20 mL) and brine (20 mL). The organic layer was dried over anhydrous MgSO$_4$, filtered and concentrated under reduced pressure to provide the crude product, which was purified by silica gel column chromatography (0-80% ethyl acetate/hexanes) to yield the title compound as a mixture of enantiomers. $^1$H-NMR (400 MHz, CDCl$_3$): δ 8.77 (d, J=1.9 Hz, 1H), 8.75 (d, J=2.2 Hz, 1H), 7.81-7.79 (m, 1H), 5.25-5.21 (m, 1H), 3.37-3.25 (m, 2H), 2.99-2.91 (m, 2H), 2.65-2.58 (m, 1H), 2.01-1.87 (m, 4H), 1.67-1.64 (m, 1H), 1.40-1.28 (m, 6H). LCMS (Method B): m/z=285.3 [M+H]$^+$.

Examples 10 and 11

6-(difluoromethyl)-3-(5-fluoro-3-pyridyl)-6-methyl-1,2,3,7,8,9-hexahydropyrazolo[1,2-a]diazepin-5-one

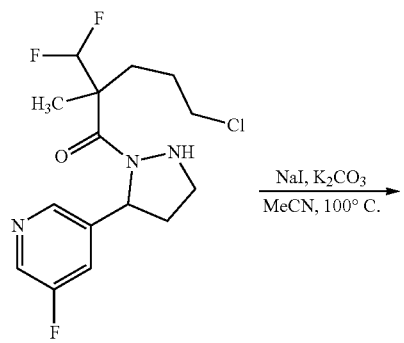

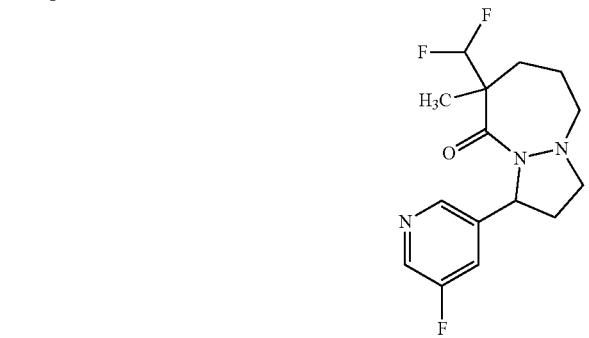

The title compounds were prepared according to Procedure B and purified by flash chromatography (0-80% ethyl acetate in hexanes) to yield the diastereomeric mixture of enantiomers. 6-(difluoromethyl)-3-(5-fluoro-3-pyridyl)-6-methyl-1,2,3,7,8,9-hexahydropyrazolo[1,2-a]diazepin-5-one as the first eluting mixture of enantiomers (Example 10). LCMS (Method B): m/z=314.3 [M+H]$^+$.

6-(difluoromethyl)-3-(5-fluoro-3-pyridyl)-6-methyl-1,2,3,7,8,9-hexahydropyrazolo[1,2-a]diazepin-5-one as the second eluting mixture of enantiomers (Example 11). LCMS (Method B): m/z=314.3 [M+H]$^+$.

Examples 12 and 13

6-(difluoromethyl)-6-methyl-3-(5-methylpyrazin-2-yl)-1,2,3,7,8,9-hexahydropyrazolo[1,2-a]diazepin-5-one

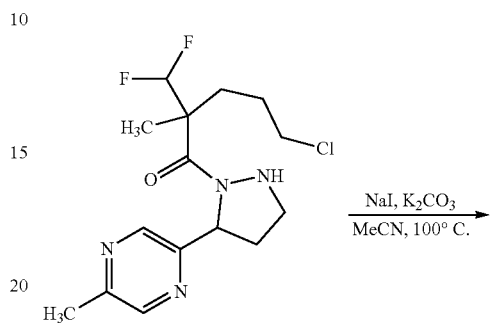

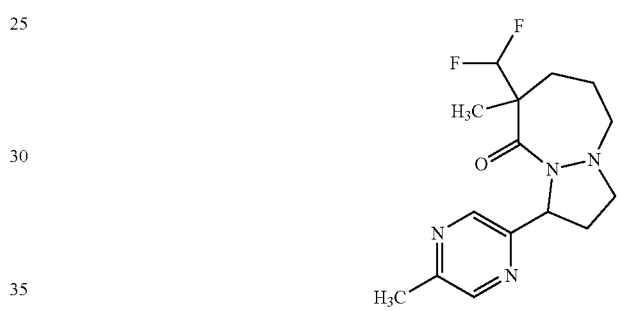

The title compounds were prepared according to Procedure B and purified by flash chromatography (0-80% ethyl acetate in hexanes) to yield the diastereomeric mixture of enantiomers. The first eluting mixture of enantiomers was further purified by SFC with the following conditions: Column: Chiralpak AD-H 250×30 mm i.d. 5 μm; mobile phase A: CO$_2$, mobile phase B: MeOH (0.1% NH$_3$H$_2$O); gradient: B %=28%; flow rate: 60 g/min; wavelength: 220 nm; column temperature: 40° C.; system back pressure: 100 bar to provide the title compound as the second eluting enantiomer (Example 12). $^1$H NMR (400 MHz, CDCl$_3$) δ 8.59-8.44 (m, 1H), 8.36 (s, 1H), 6.98-6.34 (m, 1H), 5.17 (m, 1H), 3.55-3.17 (m, 3H), 2.84 (br s, 1H), 2.62-2.40 (m, 5H), 2.03-1.82 (m, 1H), 1.73-1.49 (m, 4H), 1.42-1.14 (m, 2H). LCMS (Method E): m/z=311.4 [M+H]$^+$, 1.483 min.

The second eluting mixture of enantiomers was purified by SFC with the following conditions: Column: Chiralpak AD-H 250×30 mm i.d. 5 μm; mobile phase A: CO$_2$, mobile phase B: MeOH (0.1% NH$_3$H$_2$O); gradient: B %=28%; flow rate: 60 g/min; wavelength: 220 nm; column temperature: 40° C.; system back pressure: 100 bar to provide the title compound as the second eluting enantiomer (Example 13). $^1$H NMR (400 MHz, CDCl$_3$) δ 8.50 (br s, 1H), 8.36 (s, 1H), 6.56-5.90 (m, 1H), 5.16 (br s, 1H), 3.45-3.08 (m, 3H), 2.88-2.67 (m, 1H), 2.54 (s, 3H), 2.47 (br s, 1H), 2.06-1.52 (m, 5H), 1.46-1.29 (m, 3H). LCMS (Method E): m/z=311.4 [M+H]$^+$, 1.501 min.

Examples 14 and 15

5-[6-(difluoromethyl)-6-methyl-5-oxo-1,2,3,7,8,9-hexahydropyrazolo[1,2-a]diazepin-3-yl]pyridine-3-carbonitrile

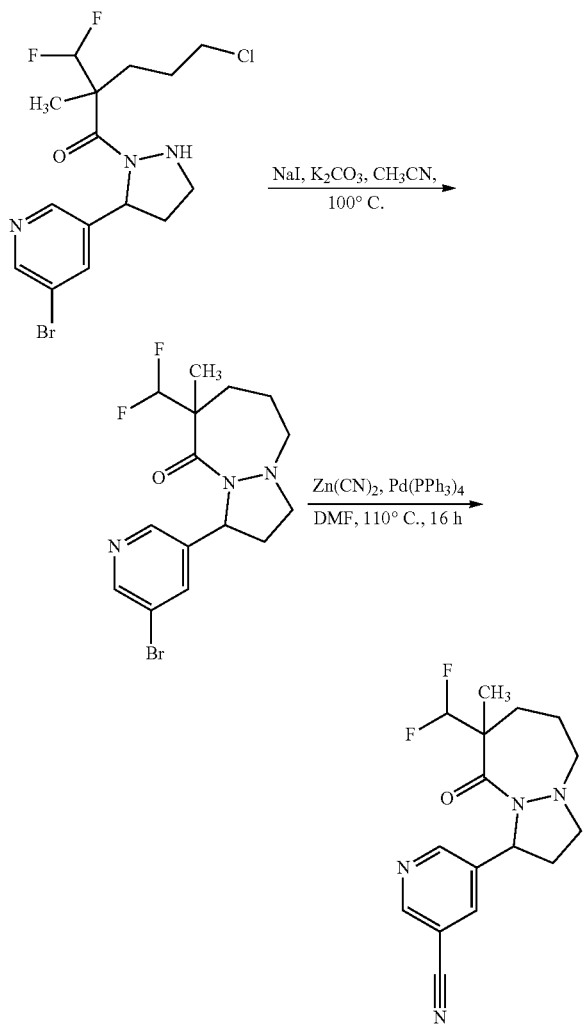

3-(5-bromo-3-pyridyl)-6-(difluoromethyl)-6-methyl-1,2,3,7,8,9-hexahydropyrazolo[1,2-a]diazepin-5-one: The title compound was prepared according to Procedure B and purified by prep-TLC (SiO$_2$, PE:EtOAc=1:1) to afford the first eluting mixture of enantiomers and the second eluting mixture of enantiomers.

5-(6-(difluoromethyl)-6-methyl-5-oxo-1,2,3,7,8,9-hexahydropyrazolo[1,2-a]diazepin-3-yl)pyridine-3-carbonitrile (Example 14): To a mixture of 3-(5-bromo-3-pyridyl)-6-(difluoromethyl)-6-methyl-1,2,3,7,8,9-hexahydropyrazolo[1,2-a]diazepin-5-one (0.05 g, 0.13 mmol) (the first eluting mixture of enantiomers) and Zn(CN)$_2$ (16 mg, 0.13 mmol) in DMF (3 mL) was added Pd(PPh$_3$)$_4$ (46 mg, 40.08 μmol) in one portion at 25° C. under N$_2$. The reaction mixture was heated at 110° C. for 16 h, cooled to 25° C. and poured into saturated aqueous NaHCO$_3$ (20 mL). The aqueous phase was extracted with EtOAc (3×15 mL). The combined organic phase was washed with brine (10 mL), dried over anhydrous Na$_2$SO$_4$, filtered and concentrated under reduced pressure. The resulting residue was purified by Prep-HPLC with the following conditions: column: Xtimate C18 150×25 mm×5 μm; mobile phase A: water (10 mM NH$_4$HCO$_3$), mobile phase B: ACN; B %: 30%-45% over 10.5 min to provide a mixture of enantiomers as a colorless oil. Further purification by SFC with the following conditions: column: AD (250 mm×30 mm, 5 μm); mobile phase: [0.1% NH$_3$H$_2$O—MeOH]; B %: 30%-30% over 10 min provided the title compound as the second eluting enantiomer (Example 14). $^1$H NMR (400 MHz, CDCl$_3$) δ 8.78 (d, J=1.88 Hz, 1H), 8.72 (s, 1H), 7.77 (br s, 1H), 6.32 (s, 1H), 5.20 (br s, 1H), 3.32 (br s, 2H), 2.85-3.05 (m, 2H), 2.69 (br s, 1H), 1.89-2.11 (m, 4H), 1.68 (br d, J=12.42 Hz, 1H), 1.40 (br s, 3H); LC-MS (Method E): m/z=321.3 [M+H]$^+$, 1.471 mM.

5-(6-(difluoromethyl)-6-methyl-5-oxo-1,2,3,7,8,9-hexahydropyrazolo[1,2-a]diazepin-3-yl)pyridine-3-carbonitrile (Example 15): To a mixture of 3-(5-bromo-3-pyridyl)-6-(difluoromethyl)-6-methyl-1,2,3,7,8,9-hexahydropyrazolo[1,2-a]diazepin-5-one (0.2 g, 0.53 mmol) (the second eluting mixture of enantiomers) and Zn(CN)$_2$ (63 mg, 0.53 mmol) in DMF (3 mL) was added Pd(PPh$_3$)$_4$ (185 mg, 0.16 mmol) in one portion at 25° C. under N$_2$. The mixture was heated at 110° C. for 16 h, cooled to 25° C. and poured into saturated aqueous NaHCO$_3$ (50 mL). The aqueous phase was extracted with EtOAc (3×15 mL). The combined organic phase was washed with brine (10 mL), dried over anhydrous Na$_2$SO$_4$, filtered and concentrated under reduced pressure. The resulting residue was purified by Prep-HPLC with the following conditions: column: Xtimate C18 150×25 mm×5 μm; mobile phase A: water (10 mM NH$_4$HCO$_3$), mobile phase B: ACN; B %: 30%-45% over 10.5 mM to provide a mixture of enantiomers. Further separation by SFC with the following conditions: column: AD (250 mm×30 mm, 5 μm); mobile phase: [0.1% NH$_3$H$_2$O MeOH]; B %: 30%-30% over 10 mM provided the title compound as the second eluting enantiomer (Example 15). $^1$H NMR (400 MHz, CDCl$_3$) δ 8.77 (d, J=1.88 Hz, 1H), 8.72 (d, J=1.88 Hz, 1H), 7.76 (br s, 1H), 5.92-6.93 (m, 1H), 5.17 (br s, 1H), 3.11-3.45 (m, 2H), 2.88-3.04 (m, 2H), 2.65 (br s, 1H), 2.04-1.94 (m, 4H), 1.49-1.71 (m, 1H), 1.34 (br s, 3H). LC-MS (Method E): m/z=321.3 [M+H]$^+$, 1.469 min.

Example 16

3-(5-fluoro-3-pyridyl)spiro[1,2,3,7,8,9-hexahydropyrazolo[1,2-a]diazepine-6,1'-cyclopropane]-5-one

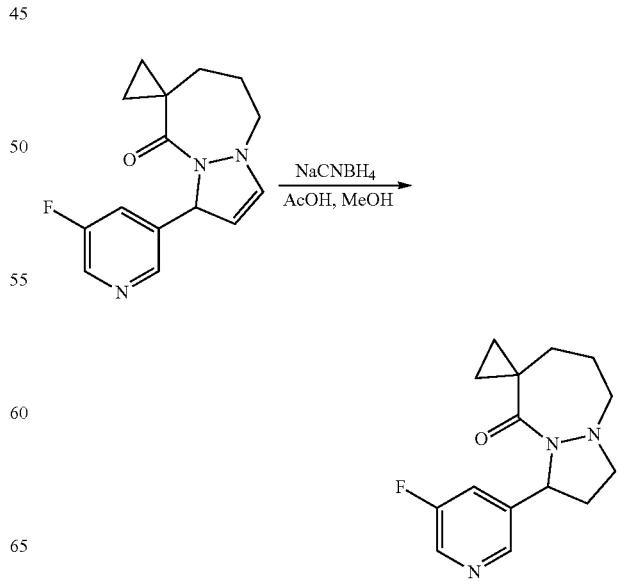

The title compound was prepared according to Procedure A and purified by prep-HPLC with the following conditions (column: Luna C18 100×30 mm 5 µm; mobile phase A: water (0.1% TFA), mobile phase B: ACN; B %: 10%-35% over 10 min) to provide the desired product as a mixture of enantiomers. LCMS (Method E): m/z=276.3 [M+H]$^+$, 1.190 min. $^1$H NMR (400 MHz, CDCl$_3$) δ 8.57-8.26 (m, 2H), 7.30 (td, J=2.4, 9.2 Hz, 1H), 5.19 (t, J=7.2 Hz, 1H), 3.41 (ddd, J=6.4, 8.4, 11.2 Hz, 1H), 3.17 (td, J=6.0, 11.6 Hz, 1H), 3.11-2.94 (m, 2H), 2.60-2.45 (m, 1H), 2.14 (qd, J=6.4, 14.4 Hz, 1H), 2.04-1.84 (m, 2H), 1.83-1.70 (m, 1H), 1.63 (dt, J=3.2, 7.2 Hz, 1H), 1.34 (ddd, J=4.0, 6.4, 10.0 Hz, 1H), 0.98 (ddd, J=4.4, 6.0, 10.0 Hz, 1H), 0.73 (ddd, J=4.4, 6.8, 9.2 Hz, 1H), 0.50 (ddd, J=4.0, 6.4, 9.2 Hz, 1H).

Examples 17 and 18

6-(difluoromethyl)-6-ethyl-3-(5-methylpyrazin-2-yl)-1,2,3,7,8,9-hexahydropyrazolo[1,2-a]diazepin-5-one

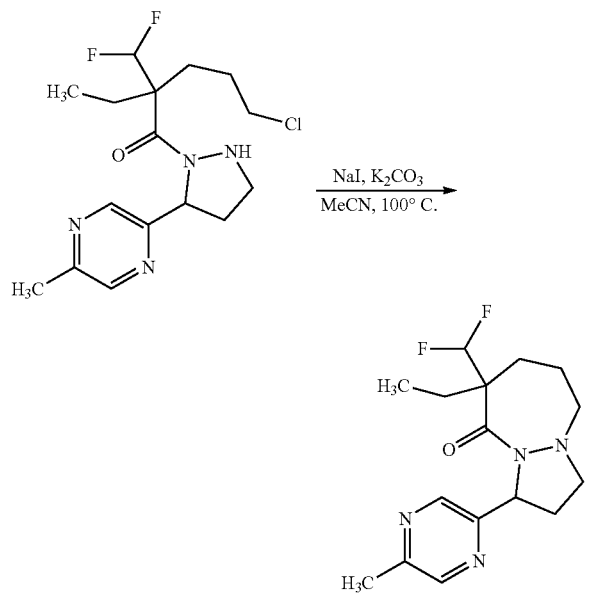

The title compounds were prepared according to Procedure B and purified by flash chromatography (0-80% EtOAc in hexanes) to provide the first eluting mixture of enantiomers, which was further purified by SFC with the following conditions (column: IC-H (250×30 mm, 5 µm); mobile phase: [0.1% NH$_3$H$_2$O MeOH]; B %: 25%-25% over 10 min) to provide the second eluting enantiomer (Example 17). $^1$H NMR (400 MHz, CDCl$_3$) δ 8.49 (br s, 1H), 8.34 (s, 1H), 6.63-5.99 (m, 1H), 5.22 (br d, J=8.8 Hz, 1H), 3.74 (br s, 1H), 3.15 (br s, 1H), 2.91 (br s, 1H), 2.64 (br s, 1H), 2.57-2.50 (m, 2H), 2.50-2.23 (m, 1H), 2.20-1.86 (m, 1H), 2.22-1.86 (m, 2H), 1.86-1.45 (m, 4H), 0.79 (t, J=7.6 Hz, 3H); LC-MS (Method E): m/z=325.4 [M+H]$^+$, 1.565 min and the second eluting mixture of enantiomer (Example 18). LC-MS: m/z=325.3 [M+H]$^+$.

IN VITRO ASSAY 1

Receptor Interacting Protein Kinase 1 Inhibition by Compounds of Formula I

Fluorescent Polarization Binding (FP Binding) assay (Berger S. B. et al. (2015) *Cell Death Discovery*, 1: 15009; Maki J. L. et al. (2012) *Anal Biochem.*, 427 (2): 164-174) was performed in polystyrene low volume 384-well black plate, at Room Temperature (RT) in a final volume of 10.1 µL/well using 10 nM of GST-hRIPK1 (8-327) enzyme and 5 nM of fluorescent-labeled ligand (14-(2-{[3-({2-{[4-(cyanomethyl)phenyl]amino}-6-[(5-cyclopropyl-1H-pyrazol-3-yl)amino]-4-pyrimidinyl}amino) propyl]amino}-2-oxoethyl)-16,16,18,18-tetramethyl-6,7,7a,8a,9,10,16,18-octahydrobenzo [2",3"]indolizino[8",7":5',6']pyrano [3',2':3,4]pyrido[1,2-a]indol-5-ium-2-sulfonate.

Test compounds were serially diluted in DMSO at 100 fold final concentrations in the assay (1% DMSO final). In each well of a 384-well Plate were dispensed 0.1 µL of compound solution (or DMSO for controls) followed by 5 µL of GST-hRIPK1 (8-327) at twice the final concentrations in assay buffer (50 mM HEPES pH 7.5, 10 mM NaCl, 50 mM MgCl$_2$, 0.02% CHAPS, 0.5 mM DTT and 0.01% Pluronic F127). For negative control the enzyme addition was replaced by assay buffer only.

After addition of 5 µL of fluorescent-labeled ligand at twice the final concentrations in assay buffer, the plate was incubated at RT for 30 mM. At the end, the binding was measured as FP value with the Envision (PerkinElmer) plate reader using filter for an excitation λ=531 nm FP and an emission λ=595 nm FP (S & P-pol).

Test compound inhibition was expressed as percent inhibition of internal assay controls. For concentration response curves, normalized data is fit and IC$_{50}$ determined using XL-fit (IDBS) for Excel. IC$_{50}$ were averaged to determine a mean value, for a minimum of two independent experiments.

Receptor interacting protein kinase 1 activity of exemplary compounds was determined according to the above general procedures. Results are summarized in Table 3.

TABLE 3

| Example | RIPK1 IC$_{50}$ |
| --- | --- |
| 1 | +++ |
| 2 | +++ |
| 3 | +++ |
| 4 | +++ |
| 5 | +++ |
| 6 | +++ |
| 7 | +++ |
| 8 | ++ |
| 9 | +++ |
| 10 | +++ |
| 11 | +++ |
| 12 | +++ |
| 13 | +++ |
| 14 | +++ |
| 15 | +++ |
| 16 | ++ |
| 17 | +++ |
| 18 | +++ |

+++ indicates IC$_{50}$ < 1 µM
++ indicates 1 µM ≤ IC$_{50}$ < 30 µM
+ indicates IC$_{50}$ ≥ 30 µM Although various embodiments of the disclosure are disclosed herein, many adaptations and modifications may be made within the scope of the disclosure in accordance with the common general knowledge of those skilled in this art. Such modifications include the substitution of known equivalents for any aspect of the disclosure in order to achieve the same result in substantially the same way. Numeric ranges are inclusive of the numbers defining the range. The word "comprising" is used herein as an open-ended term, substantially equivalent to the phrase "including, but not limited to" and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present disclosure. Any priority document(s) and all publications, including but not limited to patents and patent applications, cited in this specification are incorporated herein by reference as if each individual publication were specifically and individually indicated to be incorporated by reference herein and as though fully set forth herein. The disclosure includes all embodiments and variations substantially as hereinbefore described and with reference to the examples and drawings.

The invention claimed is:
1. A compound of Formula I:

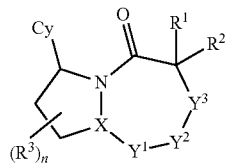

I or a pharmaceutically acceptable salt, deuterated analog, stereoisomer, mixture of stereoisomers, tautomer, or prodrug thereof, wherein:
X is N;
Cy is optionally substituted cycloalkyl, optionally substituted heterocyclyl, optionally substituted aryl, or optionally substituted heteroaryl;
$Y^1$, $Y^2$, and $Y^3$ are independently $CR^5R^6$;
$R^1$ is cyano, optionally substituted alkyl, optionally substituted alkenyl, optionally substituted alkynyl, optionally substituted alkoxy, $-SR^8$, $-SOR^8$, $-SO_2R^8$, optionally substituted cycloalkyl, optionally substituted heterocyclyl, optionally substituted aryl, or optionally substituted heteroaryl;
or $R^1$ and $Y^3$ together form an optionally substituted heterocyclyl;
$R^2$ is cyano, hydrogen, halo, optionally substituted alkyl, optionally substituted alkenyl, optionally substituted alkynyl, optionally substituted cycloalkyl, optionally substituted heterocyclyl, optionally substituted aryl, or optionally substituted heteroaryl; or $R^1$ and $R^2$ together form an optionally substituted cycloalkyl or optionally substituted heterocyclyl;
each $R^3$ is independently halo, cyano, or optionally substituted alkyl; or two $R^3$ together form an optionally substituted cycloalkyl or an optionally substituted heterocyclyl;
$R^5$ and $R^6$ are independently cyano, halo, hydrogen, hydroxyl, optionally substituted alkyl, optionally substituted alkenyl, optionally substituted alkynyl, optionally substituted alkoxy, $-SH$, $-SR^8$, $-SOR^8$, $-SO_2R^8$, optionally substituted cycloalkyl, optionally substituted heterocyclyl, optionally substituted aryl, or optionally substituted heteroaryl; or $R^5$ and $R^6$ together with the carbon atom to which they are both attached form an optionally substituted cycloalkyl, optionally substituted heterocyclyl, or oxo; or any two $R^5$ groups attached to adjacent carbon atoms together form an optionally substituted cycloalkyl or optionally substituted heterocyclyl;
$R^7$ is hydrogen or optionally substituted alkyl;
$R^8$ is optionally substituted alkyl; and
n is 0, 1, 2, 3, 4, or 5.
2. The compound of claim 1, wherein $Y^3$ are $CF_2$.
3. The compound of claim 1, wherein $Y^1$, $Y^2$, and $Y^3$ are $CH_2$.
4. The compound of claim 1, wherein Cy is optionally substituted aryl or optionally substituted heteroaryl.
5. The compound of claim 1, wherein Cy is optionally substituted phenyl, optionally substituted pyridyl, or optionally substituted pyrazine.
6. The compound of claim 1, wherein Cy is independently optionally substituted with one or more $R^{10}$, wherein
$R^{10}$ is independently cyano, halo, nitro, oxo, $-OR^{11}$, $-SR^{11}$, $-SF_5$, $-NR^{11}R^{12}$, $-C(=O)R^{13}$, $-C(=O)OR^{11}$, $-OC(=O)OR^{11}$, $-OC(=O)R^{13}$, $OC(=O)NR^{11}R^{12}$, $NR^{11}C(=O)NR^{11}R^{12}$, $-S(=O)_{1-2}R^{13}$, $-S(=O)_{1-2}NR^{11}R^{12}$, $-NR^{11}S(=O)_{1-2}R^{13}$, $-NR^{11}S(=O)_{1-2}NR^{11}R^{12}$, $-NR^{11}C(=O)R^{13}$, $-NR^{11}C(=O)OR^{12}$, $-C=NOR^{11}$, $C_{1-12}$ alkyl, $C_{2-12}$ alkenyl, $C_{2-12}$ alkynyl, $C_{3-10}$ cycloalkyl, heterocyclyl, aryl, or heteroaryl; wherein the $C_{1-12}$ alkyl, $C_{2-12}$ alkenyl and $C_{2-12}$ alkynyl are optionally substituted with one or more halo; the $C_{3-10}$ cycloalkyl, heterocyclyl, aryl, heteroaryl are independently optionally substituted with one or more cyano, halo, nitro, oxo, $-OR^{14}$, $-SR^{14}$, $-SF_5$, $-NR^{14}R^{15}$, $-S(=O)_{1-2}R^{16}$, $-S(=O)_{1-2}NR^{14}R^{15}$, $-NR^{14}S(=O)_{1-2}R^{16}$, or $R^{16}$;
$R^{11}$, $R^{12}$, $R^{14}$, and $R^{15}$ are independently H or $C_{1-12}$ alkyl optionally substituted with one or more halo, or two of $R^{11}$ and $R^{12}$ or two of $R^{14}$ and $R^{15}$ together with the atoms to which they are attached form a heterocyclyl optionally substituted with one or more halo or $C_{1-12}$ alkyl optionally substituted with one or more halo; and
$R^{13}$ and $R^{16}$ are independently $C_{1-12}$ alkyl optionally substituted with one or more halo.
7. The compound of claim 1, wherein Cy is 5-cyano-pyrid-3-yl, 5-fluoro-pyrid-3-yl, 3-fluorophenyl, 3-cyanophenyl, 3-cyano-5-fluorophenyl, 5-methylpyrazin-2-yl, 3,4-difluorophenyl, or 3,5-difluorophenyl.
8. The compound of claim 1, wherein n is 0.
9. The compound of claim 1, wherein $R^1$ and $R^2$ are optionally substituted alkyl.
10. The compound of claim 1, wherein $R^1$ and $R^2$ together form a cyclopropyl ring.
11. The compound of claim 1, wherein $R^1$ is difluoromethyl, cyanomethyl, methyl, or ethyl.
12. The compound of claim 1, wherein $R^2$ is methyl.
13. A compound that is:
3-(5-fluoro-3-pyridyl)-6,6-dimethyl-1,2,3,7,8,9-hexahydropyrazolo[1,2-a[diazepin-5-one;
4-(6,6-dimethyl-5-oxo-1,2,3,7,8,9-hexahydropyrazolo[1,2-a[diazepin-3-yl)benzonitrile;
3-(3-fluorophenyl)-6,6-dimethyl-1,2,3,7,8,9-hexahydropyrazolo[1,2-a[diazepin-5-one;
3-(6,6-dimethyl-5-oxo-1,2,3,7,8,9-hexahydropyrazolo[1,2-a]diazepin-3-yl)-5-fluoro-benzonitrile;
6,6-dimethyl-3-(5-methylpyrazin-2-yl)-1,2,3,7,8,9-hexahydropyrazolo[1,2-a]diazepin-5-one;
3-(3,4-difluorophenyl)-6,6-dimethyl-1,2,3,7,8,9-hexahydropyrazolo[1,2-a]diazepin-5-one;
3-(3,5-difluorophenyl)-6,6-dimethyl-1,2,3,7,8,9-hexahydropyrazolo[1,2-a]diazepin-5-one;

5-(6,6-dimethyl-5-oxo-1,2,3,7,8,9-hexahydropyrazolo[1,2-a]diazepin-3-yl)pyridine-3-carbonitrile;

6-(difluoromethyl)-6-methyl-3-(5-methylpyrazin-2-yl)-1,2,3,7,8,9-hexahydropyrazolo[1,2-a]diazepin-5-one;

3-(5-fluoro-3-pyridyl)spiro[1,2,3,7,8,9-hexahydropyrazolo[1,2-a]diazepine-6,1'-cyclopropane]-5-one;

6-(difluoromethyl)-3-(5-fluoro-3-pyridyl)-6-methyl-1,2,3,7,8,9-hexahydropyrazolo[1,2-a]diazepin-5-one;

2-[6-methyl-3-(5-methylpyrazin-2-yl)-5-oxo-1,2,3,7,8,9-hexahydropyrazolo[1,2-a]diazepin-6-yl]acetonitrile;

2-[3-(5-fluoro-3-pyridyl)-6-methyl-5-oxo-1,2,3,7,8,9-hexahydropyrazolo[1,2-a]diazepin-6-yl]acetonitrile;

5-[6-(difluoromethyl)-6-methyl-5-oxo-1,2,3,7,8,9-hexahydropyrazolo[1,2-a]diazepin-3-yl]pyridine-3-carbonitrile;

7,7-difluoro-3-(5-fluoro-3-pyridyl)-6,6-dimethyl-2,3,8,9-tetrahydro-1H-pyrazolo[1,2-a]diazepin-5-one; or 6-(difluoromethyl)-6-ethyl-3-(5-methylpyrazin-2-yl)-1,2,3,7,8,9-hexahydropyrazolo[1,2-a]diazepin-5-one;

or a pharmaceutically acceptable salt, deuterated analog, stereoisomer, mixture of stereoisomers, tautomer, or prodrug thereof.

14. A pharmaceutical composition comprising a compound of claim 1 or a pharmaceutically acceptable salt, stereoisomer, mixture of stereoisomers or prodrug thereof, and a pharmaceutically acceptable carrier.

15. A compound that is:

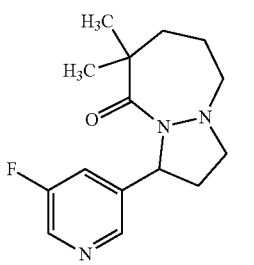
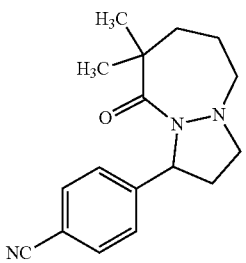
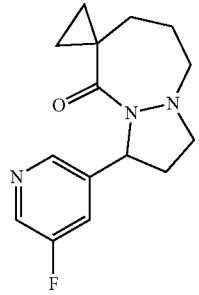
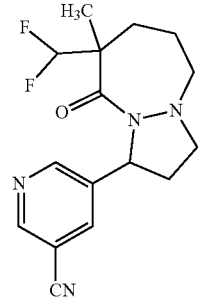
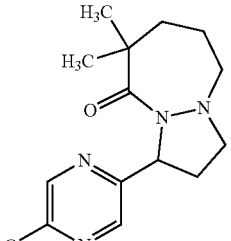
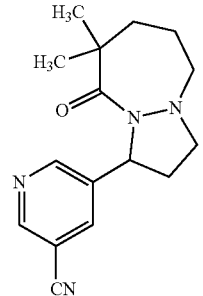

-continued

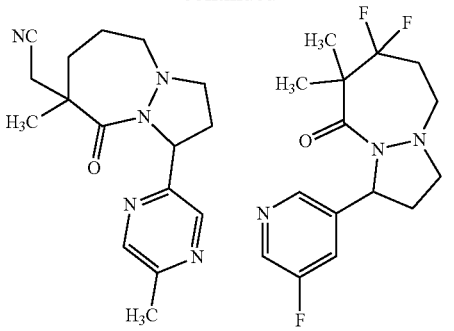
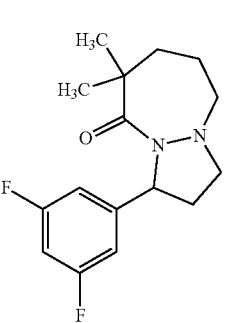
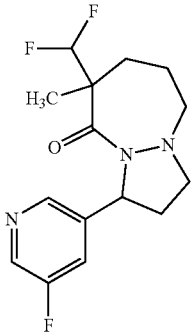
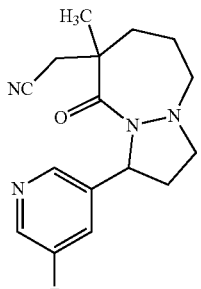
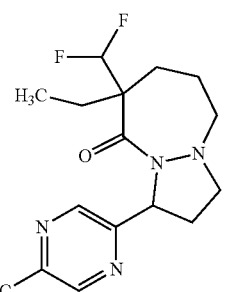
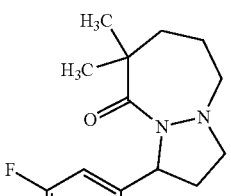
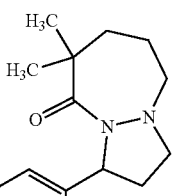
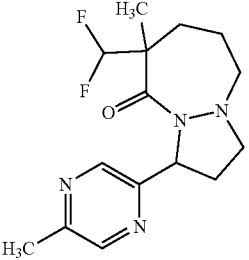
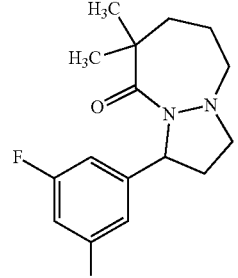

or a pharmaceutically acceptable salt, deuterated analog, stereoisomer, mixture of stereoisomers, tautomer, or prodrug thereof.

16. A compound that is:
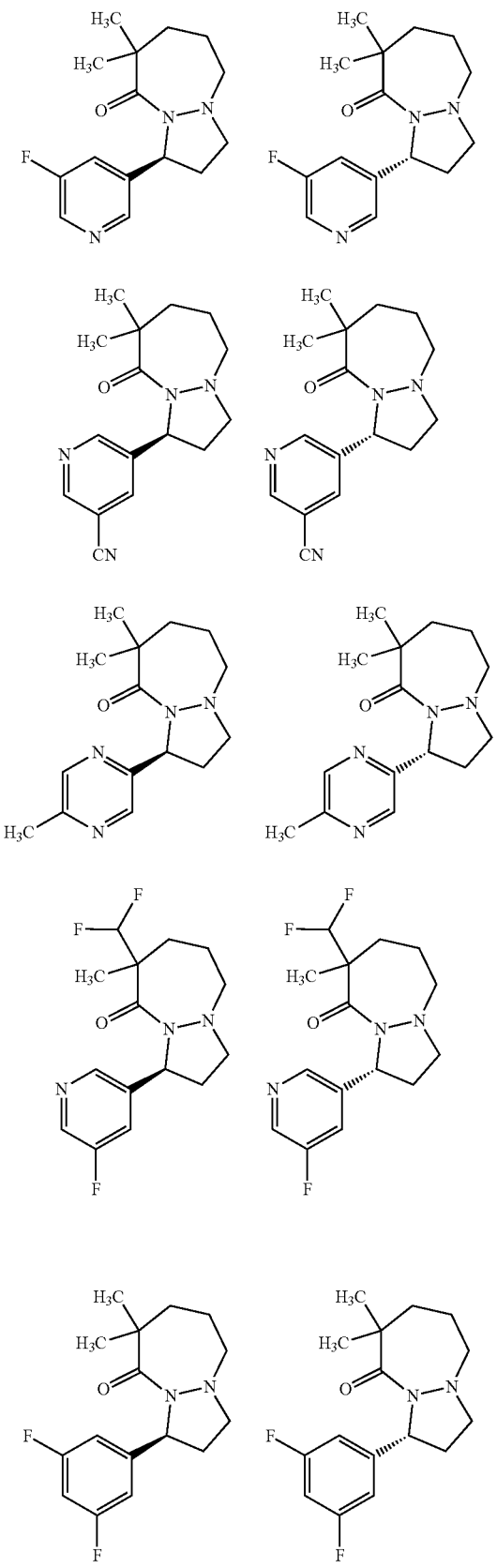
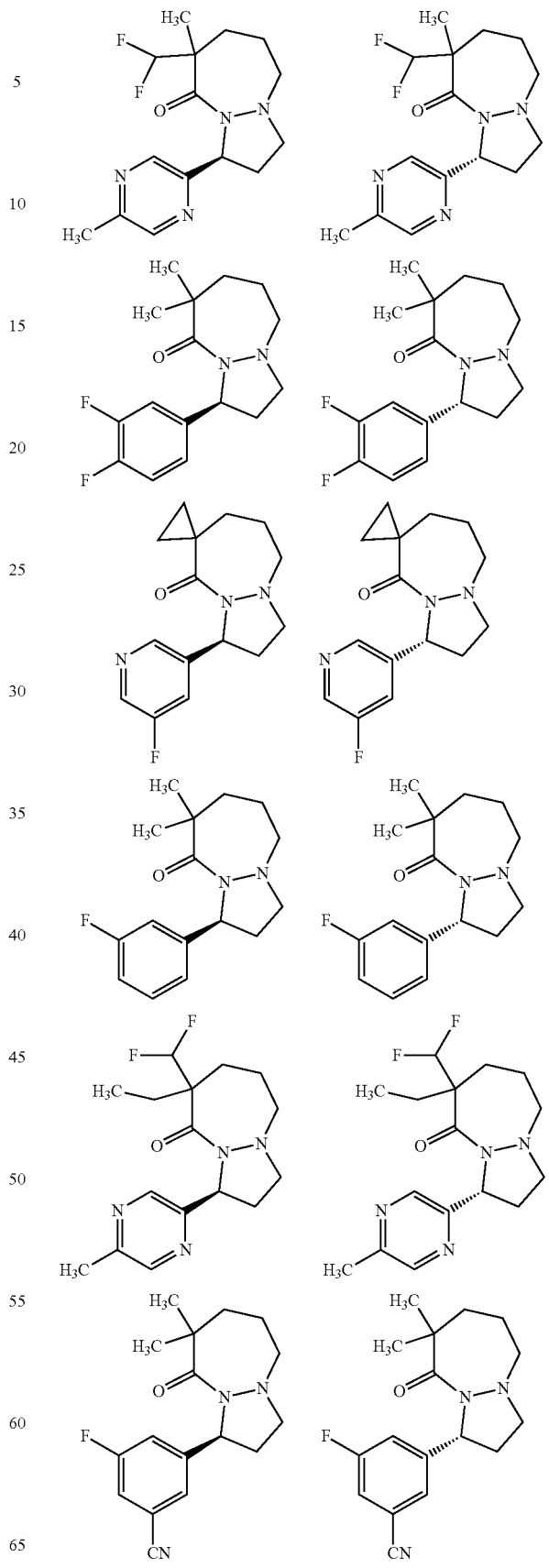
-continued

-continued
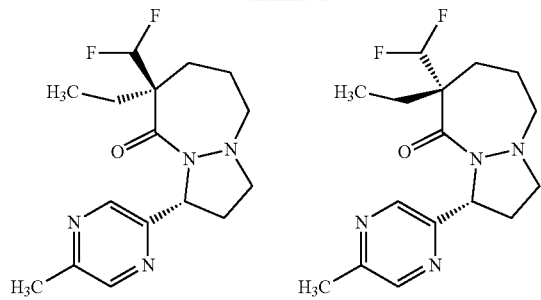
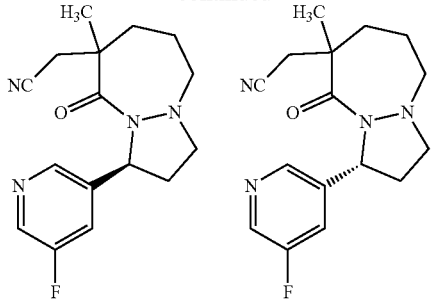
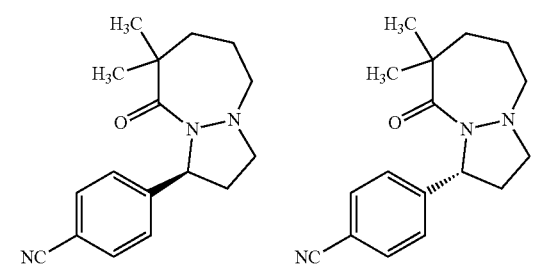
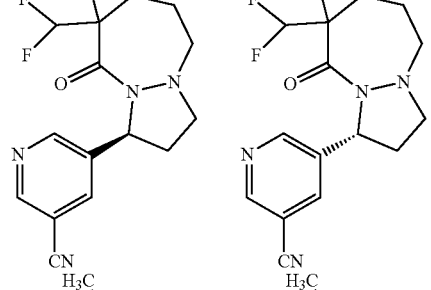
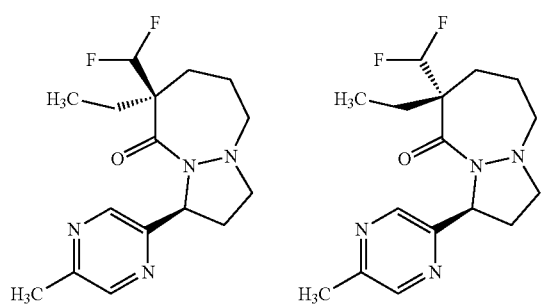
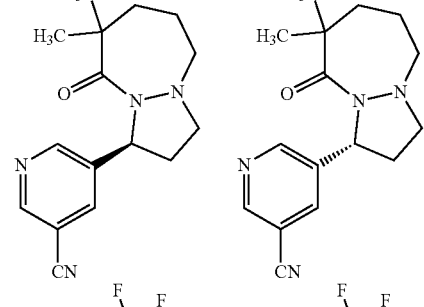
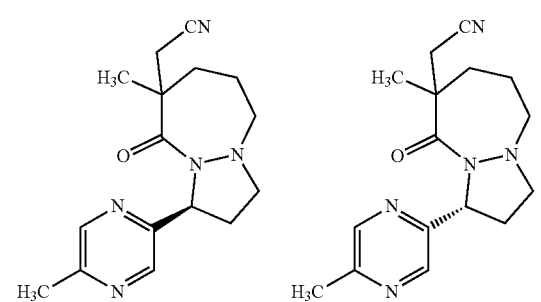
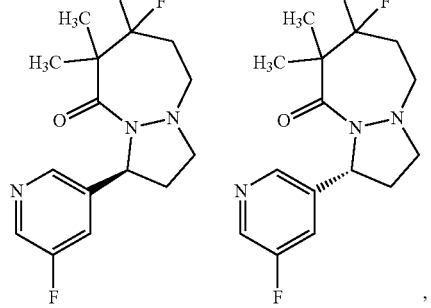
or a pharmaceutically acceptable salt, deuterated analog, stereoisomer, mixture of stereoisomers, tautomer, or prodrug thereof.
* * * * *

UNITED STATES PATENT AND TRADEMARK OFFICE
CERTIFICATE OF CORRECTION

PATENT NO. : 11,174,262 B2  
APPLICATION NO. : 16/683970  
DATED : November 16, 2021  
INVENTOR(S) : Giorgio Bonanomi et al.

Page 1 of 1

It is certified that error appears in the above-identified patent and that said Letters Patent is hereby corrected as shown below:

In the Claims

In Claim 6, Column 94, Lines 19-21:
"-SR11, -SF5, -NR11R12, -C(=O)R13, -C(=O)OR11, -OC(=O)OR11, -OC(=O)R13, OC(=O)NR11R12, NR11C(=O)NR11R12, -S(=O)1-2R13,"
Should read:
"-SR11, -SF5, -NR11R12, -C(=O)R13, -C(=O)OR11, -OC(=O)OR11, -OC(=O)R13, -C(=O)NR11R12, -OC(=O)NR11R12, -NR11C(=O)NR11R12, -S(=O)1-2R13,".

Signed and Sealed this  
Twenty-second Day of February, 2022

Drew Hirshfeld  
*Performing the Functions and Duties of the  
Under Secretary of Commerce for Intellectual Property and  
Director of the United States Patent and Trademark Office*